United States Patent
Zoellner et al.

(10) Patent No.: US 9,748,493 B2
(45) Date of Patent: Aug. 29, 2017

(54) AROMATIC AMINE-TERPHENYL COMPOUNDS AND USE THEREOF IN ORGANIC SEMICONDUCTING COMPONENTS

(71) Applicant: Novaled GmbH, Dresden (DE)

(72) Inventors: Mike Zoellner, Dresden (DE); Sascha Dorok, Dresden (DE); Jens Wutke, Dresden (DE); Sandra Heyne, Eberbach (DE)

(73) Assignee: Novaled GmbH, Dresden (DE)

( * ) Notice: Subject to any disclaimer, the term of this patent is extended or adjusted under 35 U.S.C. 154(b) by 0 days.

(21) Appl. No.: 14/384,886

(22) PCT Filed: Mar. 12, 2013

(86) PCT No.: PCT/DE2013/100092
§ 371 (c)(1),
(2) Date: Sep. 12, 2014

(87) PCT Pub. No.: WO2013/135237
PCT Pub. Date: Sep. 19, 2013

(65) Prior Publication Data
US 2015/0011795 A1 Jan. 8, 2015

(30) Foreign Application Priority Data

Mar. 15, 2012 (DE) .................. 10 2012 005 215
Apr. 20, 2012 (DE) .................. 10 2012 007 795

(51) Int. Cl.
| | |
|---|---|
| *C07C 211/54* | (2006.01) |
| *H01L 51/00* | (2006.01) |
| *C07C 211/59* | (2006.01) |
| *C07C 217/92* | (2006.01) |
| *H01L 51/42* | (2006.01) |
| *H01L 51/50* | (2006.01) |

(52) U.S. Cl.
CPC .......... *H01L 51/006* (2013.01); *C07C 211/54* (2013.01); *C07C 211/59* (2013.01); *C07C 217/92* (2013.01); *H01L 51/0059* (2013.01); *H01L 51/42* (2013.01); *H01L 51/50* (2013.01); *Y02E 10/549* (2013.01)

(58) Field of Classification Search
None
See application file for complete search history.

(56) References Cited

U.S. PATENT DOCUMENTS

| | | |
|---|---|---|
| 7,274,141 B2 | 9/2007 | Leo et al. |
| 7,675,057 B2 | 3/2010 | Drechsel et al. |
| 7,799,492 B2 | 9/2010 | Abe et al. |
| 8,502,200 B2 | 8/2013 | Schwartz et al. |
| 8,617,426 B2 | 12/2013 | Hartmann et al. |
| 8,673,792 B2 | 3/2014 | Nagai et al. |
| 2004/0185300 A1 | 9/2004 | Hatwar et al. |
| 2006/0027834 A1 | 2/2006 | Forrest et al. |
| 2006/0033115 A1 | 2/2006 | Blochwitz et al. |
| 2006/0040132 A1 | 2/2006 | Liao et al. |
| 2007/0296331 A1* | 12/2007 | Yabunouchi .......... C07C 211/58 313/504 |
| 2008/0153019 A1 | 6/2008 | Wang et al. |
| 2008/0265216 A1 | 10/2008 | Hartmann et al. |
| 2011/0220880 A1 | 9/2011 | Cheng et al. |
| 2014/0225100 A1 | 8/2014 | Yokoyama et al. |

FOREIGN PATENT DOCUMENTS

| | | |
|---|---|---|
| DE | 10 2012 005 215 B3 | 4/2013 |
| EP | 1 478 025 A2 | 11/2004 |
| EP | 1 752 441 A1 | 2/2007 |
| EP | 1 995 234 A1 | 11/2008 |
| EP | 2 042 481 A1 | 4/2009 |
| EP | 2180029 A1 | 4/2010 |
| WO | 2005/109542 A1 | 11/2005 |

OTHER PUBLICATIONS

PCT International Preliminary Report on Patentability for PCT Application No. PCT/DE2013/100092 mailed Sep. 25, 2014 (12 pages) (English translation).
Baillie et al., "Palladium-Catalysed Synthesis of Biaryl Phospines," Tetrahedron, 2004, 60:4159-4168.
Bard et al., "Introduction and Overview of Electrode Processes," Wiley, 2000, Chapter 1, pp. 1-28 and 239-247.
Benvenho et al., "Efficient Organic Light-Emitting Diodes with Fluorine-Doped Tin-Oxide Anode and Electrochemically Synthesized Sulfonated Polyaniline as Hole Transport Layer," Brazilian Journal of Physics, 2005, 35 (4A):1016-1019.
Bloom et al., "Tervalent Conducting Polymers with Tailor-Made Work Functions: Preparation, Characterization, and Application as Cathodes in Electroluminescent Devices," J. Am. Chem. Soc., 2001, 123:9436-9442.
Connelly et al., "Chemical Redox Agents for Organometallic Chemistry," Chem. Rev., 1996, 96:877-910.
D'Andrade et al., "Relationship Between the Ionization and Oxidation Potentials of Molecular Organic Semiconductors," Organic Electronics, 2005, 6:11-20.
Fu et al., "Quantum-Chemical Predictions of Absolute Standard Redox Potentials of Diverse Organic Molecules and Free Radicals in Acetonitrile," J. Am. Chem. Soc., 2005, 127:7227-7234.
Koepp et al., "Der Vergleich der Spannungareihen in Verschiedenen Solventien, II," Bd. 1960, 64(4):483-491.

(Continued)

*Primary Examiner* — Clinton Brooks
(74) *Attorney, Agent, or Firm* — Eversheds Sutherland (US) LLP

(57) ABSTRACT

The present invention relates to aromatic amine-terphenyl compounds and use thereof in organic semiconducting components. The organic semiconducting components may contain at least one layer that includes one or more of the aromatic amine-terphenyl compounds, and the layer may be a charge transporting layer or an emitter layer. The organic semiconducting components may be organic light-emitting diodes or photovoltaic components.

16 Claims, No Drawings

(56) References Cited

OTHER PUBLICATIONS

Pommerehne et al., "Efficient Two Layer LEDs on a Polymer Blend Basis," Adv. Mater., 1995, 7(6):551-554.
Sato et al., "Polarization Energies of Organic Solids Determined by Ultraviolet Photoelectron Spectroscopy," J. Chem. Soc., Farraday Trans., 1981, 2(77):1621-1633.
Trasatti, "The Absolute Electrode Potential: An Explanatory Note," Pure & Appl. Chem., 1986, 58(7):955-966.
PCT International Search Report for PCT Application No. PCT/DE2013/100092 mailed Jun. 19, 2013 (6 pages).
Chinese Office Action mailed Jul. 20, 2015 for CN Application No. 201380024155.2 (9 pages).
Taiwanese Office Action for TW Application No. 102108403 mailed Aug. 8, 2016 (6 pages) (English translation).
Chinese Office Action for CN Application No. 201380024155.2 mailed Apr. 13, 2016 (10 pages) (English translation).
Japanese Office Action for JP Application No. 2014-561286 mailed Oct. 25, 2016 (4 pages) (English translation).

\* cited by examiner

AROMATIC AMINE-TERPHENYL COMPOUNDS AND USE THEREOF IN ORGANIC SEMICONDUCTING COMPONENTS

CROSS-REFERENCE TO RELATED APPLICATIONS

This is a submission pursuant to 35 U.S.C. 154(d)(4) to enter the national stage under 35 U.S.C. 371 for PCT/DE2013/100092, filed 12 Mar. 2013. Priority is claimed under 35 U.S.C. 119(a) and 35 U.S.C. 365(b) to German Application No. 10 2012 005 215.4, filed 15 Mar. 2012 and German Application No. 10 2012 007 795.5, filed 20 Apr. 2012. The subject matters of PCT/DE2013/100092 and European Applications No. 10 2012 005 215.4 and 10 2012 007 795.5 are incorporated herein by reference.

FIELD OF THE INVENTION

The present invention relates to aromatic amine-terphenyl compounds and use thereof in organic semiconducting components.

BACKGROUND OF THE INVENTION

Components that contain at least one organic semiconducting layer are considered to be organic semiconducting components. Known organic semiconductor components include, for example, organic light-emitting diodes (OLEDs), field-effect transistors, photodetectors and organic solar cells (OPVs), in which organic semiconducting materials are used, for example as charge transport material or blocker material, preferably as hole conductors or electron blockers.

By way of example, organic light-emitting diodes utilise the property of materials to emit light when, by application of a voltage, suitable charge carriers are formed, which form excited states with recombination thereof and in turn transfer into the ground state with emission of light. To improve the efficiency of organic light-emitting diodes, these often have charge transport layers besides the actual emitting layer, which charge transport layers are responsible for the transport of negative and positive charge carriers in the emitting layer. These charge transport layers are divided into hole conductors and electron conductors depending on the type of transported charge carriers. A similar layer structure is also known for photovoltaic components, such as organic solar cells. Organic semiconducting components with a number of layers can be produced by known methods, such as vacuum evaporation or the deposition from a solution.

A desired property of organic semiconducting components is a high conductivity. This can be improved, for example, by doping individual layers of the organic semiconducting components. As a result of the doping, the conductivity of the layer increases and one problem concerning a low charge carrier movability is thus overcome.

It is known to change the electrical properties, in particular the electrical conductivity, of organic semiconductors by means of doping, as is also the case with inorganic semiconductors (silicon semiconductors).

Here, an increase of the initially rather low conductivity, and also a change in the Fermi level of the semiconductor depending on the type of dopant used, are achieved by generating charge carriers in the matrix material. Here, doping leads to an increase of the conductivity of charge transport layers, whereby ohmic losses are reduced and an improved transfer of the charge carriers between contact and organic layer is achieved. The doping is characterised by a charge transfer of dopant to a close matrix molecule (n-doping, electron conductivity increases) or by a transfer of an electron from a matrix molecule to a close dopant (p-doping, hole conductivity increases). The charge transfer can be incomplete or complete and can be determined for example by the interpretation of vibration bands from FTIR measurements.

The conductivity of a thin-film sample can be measured using what is known as the two-point method. Here, contacts made of a conductive material, for example gold or indium tin oxide, are applied to a substrate. The thin film to be examined is then applied to the substrate over a large area, such that the contacts are covered by the thin film. After applying a voltage to the contacts, the current then flowing is measured. From the geometry of the contacts and the layer thickness of the sample, the conductivity of the thin-film material is given from the resistance thus determined.

At the operating temperature of a component with doped layer, the conductivity of the doped layer is to exceed the conductivity of the undoped layer. To this end, the conductivity of the doped layers at room temperature is to be high, in particular greater than $1 \cdot 10^{-8}$ S/cm, but preferably in the range between $10^{-6}$ S/cm and $10^{-2}$ S/cm. Undoped layers have conductivities of less than $1 \cdot 10^{-8}$ S/cm, usually less than $1 \cdot 10^{-10}$ S/cm.

A further essential property of the materials used in a component is the thermal stability thereof. This is of particular importance when the component is produced by vacuum vapour deposition.

The temperature stability can be determined using the same method or using the same construction by heating the (undoped or doped) layer gradually and measuring the conductivity after a rest period. The maximum temperature that the layer can withstand without losing the desired semiconductor property is then the temperature immediately before the conductivity nosedives. For example, a doped layer on a substrate with two adjacent electrodes, as described above, can be heated in steps of 1° C., wherein a period of 10 seconds elapses after each step. The conductivity is then measured. The conductivity changes with temperature and nosedives abruptly from a certain temperature. The temperature stability thus indicates the temperature up to which the conductivity does not nosedive abruptly.

With these methods, it should be ensured that the matrix materials have a sufficiently high purity. Such purities can be achieved with conventional methods, preferably gradient sublimation.

The properties of the different materials involved can be described by the energy loads of the lowest unoccupied molecular orbital (LUMO for short; synonymous with: electron affinity) and of the highest occupied molecular orbital (HOMO for short; synonymous with: ionisation potential).

A method for determining ionisation potentials (IP) is ultra-violet photoelectron spectroscopy (UPS). Ionisation potentials for the solid body are generally determined, however it is also possible to measure possible ionisation potentials in the gas phase. Both variables differ by solid body effects, such as the polarisation energy of the holes that are produced in the photoionisation process (N. Sato et al., J. Chem. Soc. Faraday Trans. 2, 77, 1621 (1981)). A typical value for the polarisation energy is approximately 1 eV, however greater deviations may also occur.

Here, the ionisation potential relates to the start of the photoemission spectrum in the region of the high kinetic energies of the photoelectrons, that is to say the energy of the most weakly bonded photoelectrons.

An associated method (inverse photoelectron spectroscopy (IPES)) can be used to determine electron affinities (EA). However, this method is less widespread. Alternatively, solid body energy levels can be determined by electrochemical measurement of oxidation potentials (Eox) and/or reduction potentials (Ered) in solution. A suitable method is cyclic voltammetry (CV). Empirical methods for deriving the solid body ionisation potential from the electrochemical oxidation potential are described in the literature (for example B. W. Andrade et al., Org. Electron. 6, 11 (2005); J. Amer. Chem. Soc. 127, (2005), 7227.).

No empirical formulas are known for the conversion of reduction potentials into electron affinities. This lies in the difficulty of determining electron affinities. A simple rule is therefore often applied: IP=4.8 eV+e·Eox (vs. ferrocene/ferrocenium) or EA=4.8 eV+e·Ered (vs. ferrocene/ferrocenium), wherein e means the electron charge (see B. W. Andrade, Org. Electron. 6, 11 (2005) and Ref. 25-28 therein). For the case that other reference electrodes or redox pairs are used to reference the electrochemical potentials, methods for the conversion are known (see A. J. Bard, L. R. Faulkner, "Electrochemical Methods: Fundamentals and Applications", Wiley, 2nd edition 2000). Information concerning the influence of a solvent can be found in N. G. Connelly et al., Chem. Rev. 96, 877 (1996).

It is usual, although also not absolutely correct, to use the terms "energy of the HOMO" E(HOMO) and "energy of the LUMO" E(LUMO) synonymously with the terms ionisation energy and electron affinity respectively (Koopmans Theorem). Here, it should be noted that the ionisation potentials and electron affinities are given such that a higher value means a stronger binding of a liberated or accumulated electron. The energy scale of the molecular orbitals (HOMO, LUMO) is the opposite. The following is therefore true for a rough approximation: IP=−E(HOMO) and EA=−E(LUMO).

In order to record a cyclic voltammogram, the substance to be examined is provided in an electrochemical cell with working electrode, counter electrode and reference electrode together with a conductive salt (for example tetrabutylammonium hexafluorophosphate, TBAPF6) and a solvent (for example dichloromethane (DCM), tetrahydrofuran (THF)). A voltage cycle is then applied to the working electrode (for example 0.0 V→1.6 V→−2.0 V→0.0 V) and is run through at a feed rate (for example 100 mV/s). Oxidative and reductive processes are made noticeable by a rise of the current. Here, in the case of reversible processes, a corresponding reductive process also takes place with each oxidative process. The redox potential is calculated here from the mean value of the peak points. In the case of irreversible processes, the peak onset is used.

EP 2042481 A1 discloses aromatic amine terphenyl derivatives that can be used in organic electroluminescence components.

EP1995234A1 describes mixtures of p-terphenyl compounds and electrophotographic photoreceptors produced with use of these mixtures.

The matrix materials known in the prior art for use in organic semiconducting components can be improved further still in terms of their conductivity, their thermal stability and also in terms of their processability from a solution.

One object of the present invention is therefore to overcome the disadvantages from the prior art and to provide materials that lead to improved organic semiconducting components, which in particular demonstrate improved conductivity, are thermally stable and/or can be processed easily from a solution. In addition, materials that can be produced easily and cost-effectively in high purity are desirable.

A further object of the present invention is to provide corresponding organic semiconducting components.

BRIEF SUMMARY

The first object is achieved by a compound of formula (I)

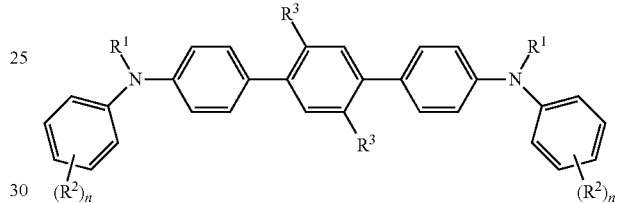

(I)

wherein
$R^1$ is selected from naphthyl or biphenylyl;
$R^2$ is selected from $C_1$-$C_{10}$ alkyl, $C_1$-$C_{10}$ alkoxy, $C_1$-$C_5$ haloalkyl and $C_6$-$C_{12}$ aryloxy;
$R^3$ is selected from H or $C_1$-$C_5$ alkyl;
n=1-3.

Preferred embodiments will emerge from the dependent claims.

DETAILED DESCRIPTION

Identically denoted substituents are preferably identical.
The substitution by R2 is particularly preferably in the ortho and/or para position of the phenyl ring.
It is also preferable if R2 is C1-C10 alkyl, C1-C10 alkoxy or C6-C12 aryloxy.
It is preferable if R1 is β-naphthyl or 1,1'-biphenyl-4-yl.
It is also preferable if R2 is C1-C5 alkyl, preferably methyl, isopropyl or tert-butyl, C1-C3 alkoxy or phenoxy. R2=phenoxy is preferable with thermal vacuum evaporation.
The compound is preferably selected from compounds of formula (II)

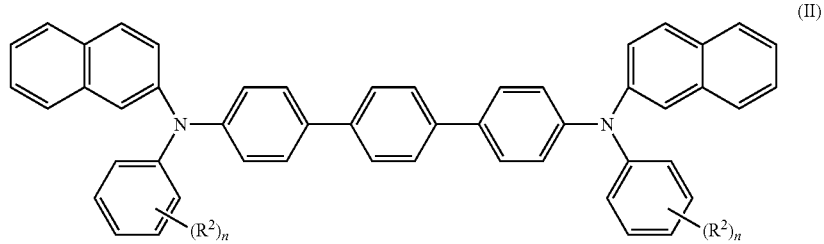

(II)

wherein $R^2$ is selected from $C_1$-$C_{10}$ alkyl, $C_1$-$C_{10}$ alkoxy, $C_1$-$C_5$ haloalkyl and $C_6$-$C_{12}$ aryloxy. It is then particularly preferred if $R^2$ is selected from $C_1$-$C_{10}$ alkyl, $C_1$-$C_{10}$ alkoxy and $C_6$-$C_{12}$ aryloxy and $R^2$ is merely in ortho and para positions or merely in para positions of the phenyl rings.

The compound is preferably also selected from compounds of formula (III)

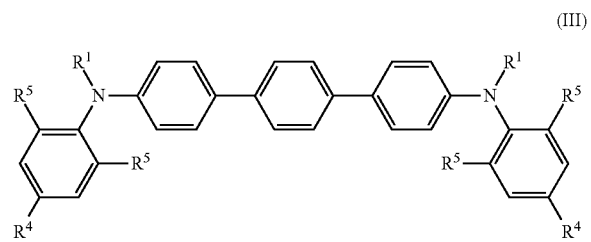

(III)

wherein $R^4$ and $R^5$ are selected independently from H and $R^2$, and wherein not all $R^4$ and $R^5$ are H at the same time.

The invention also relates to an organic semiconducting component comprising at least one layer, which contains a compound according to the present invention.

Here, the layer containing the compound is preferably doped.

It is also proposed in accordance with the invention for the layer containing the compound according to the invention to have at least one doped region and at least one region that is doped to a lesser extent than the doped region or is undoped.

An organic semiconducting component in which the layer containing the compound is a hole transport layer or emitter layer is particularly preferred.

The hole transport layer can be doped or undoped. An undoped hole transport layer containing the compound according to the invention can be arranged in a component between a light-emitting or light-absorbing layer (for example the emitter layer for an OLED) and a doped hole transport layer. This undoped hole transport layer then constitutes an electron blocker layer.

Lastly, the organic semiconducting component is preferably an organic light-emitting diode (OLED) or a photovoltaic component, preferably a solar cell.

It has surprisingly been found that the compounds proposed in accordance with the invention have a much improved conductivity and/or a much improved thermal stability compared with matrix materials that are already known. Whereas the improved conductivity is of key importance for the function/efficiency of the organic semiconducting component thus produced, the improved thermal stability means that the components, during production thereof, can be purified with high throughput by means of sublimation and the compounds according to the invention on the other hand, due to the stability thereof under sublimation, can be used easily in the production of organic semiconducting components according to the invention when layers thereof are applied by vacuum thermal evaporation.

In addition, it has surprisingly been found that the compounds according to the invention can be produced relatively easily with the need for relatively few method steps at low cost and with high purity.

The compounds according to the invention can also be used easily in the production of organic semiconductor components when corresponding layers are produced by deposition from a solution.

Lastly, it has been found that these compounds can be doped more easily than compounds from the prior art, which means that less dopant material is needed. Since a small quantity of dopant material is required, there are also lower light absorption losses.

In accordance with a preferred alternative of the invention, the following layer sequences are provided in the component: (i) anode/dopant/HTM; (ii) anode/dopant:HTM; (iii) anode/dopant/dopant:HTM. The following is more preferred: (iv) dopant/HTM/EML or (v) dopant/HTM/OAS; (vi) p-doped HTM/EML or (vii) dopant:HTM/OAS. The p-doped HTM is doped with the dopant according to the invention. HTM is the hole transport material. EML is the emitting layer of an OLED; OAS stands for "optical absorption layer of a solar cell" (typically a donor-acceptor (D-A) heterojunction). "I" means that the materials are present in separate layers in a layer stack, and ":" means that the materials are present in a layer in mixed form; the mixture may or may not be homogeneous.

The layer sequences (i)-(vii) are further preferably terminating layer sequences.

In another embodiment of the invention, a layer is formed that continuously has an HTM as matrix material and additionally has an electric dopant, which is not distributed homogeneously in the layer (in the direction of the layer thickness) and further preferably forms gradients.

Compounds that are particularly preferred in accordance with the invention are as follows:

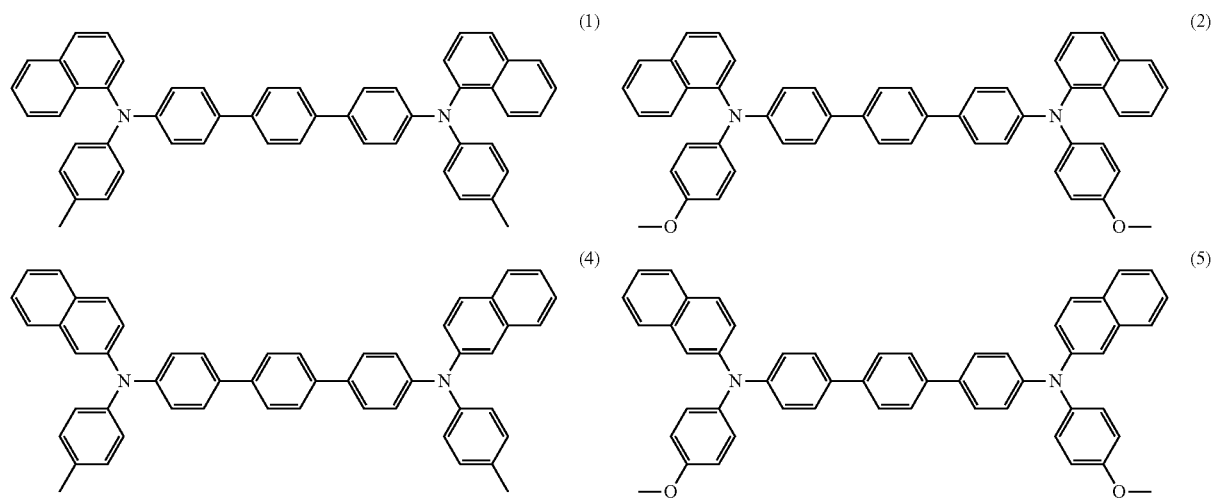

-continued
(6)
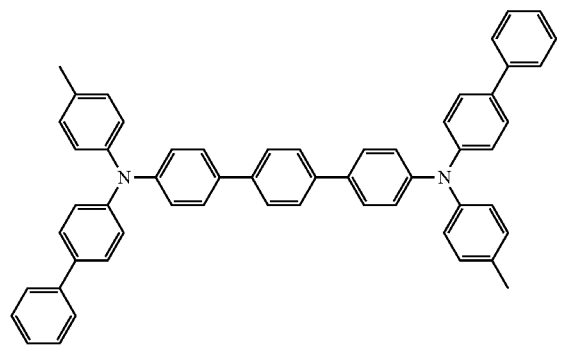
(7)
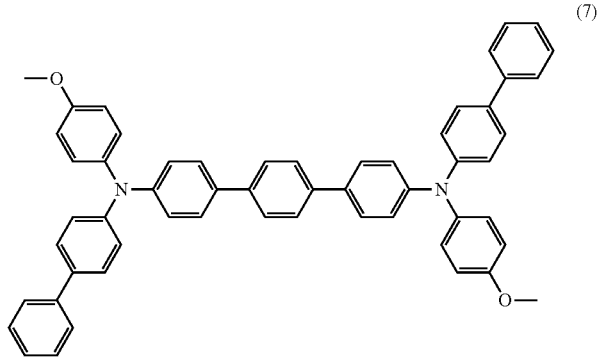
(10)
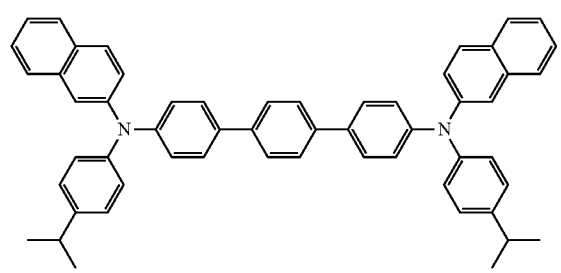
(11)
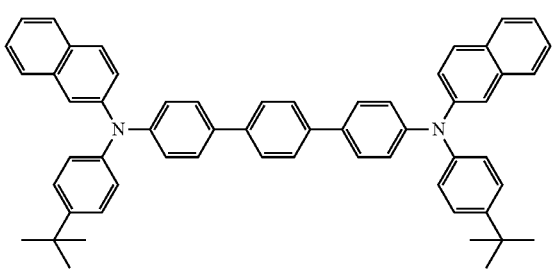
(12)
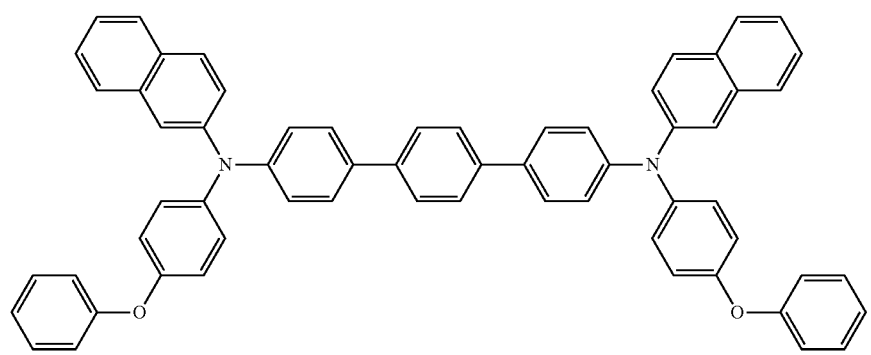
(13)
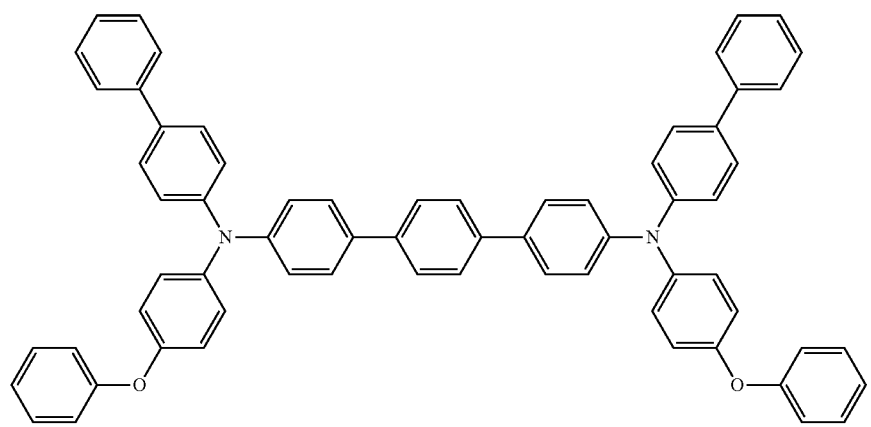

-continued
(14)
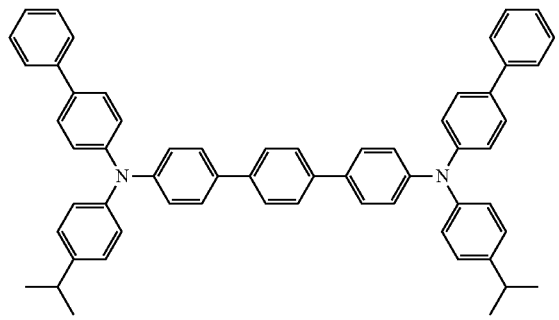
(15)
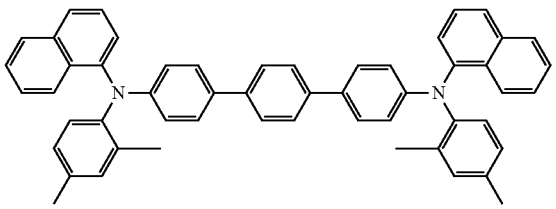
(16)
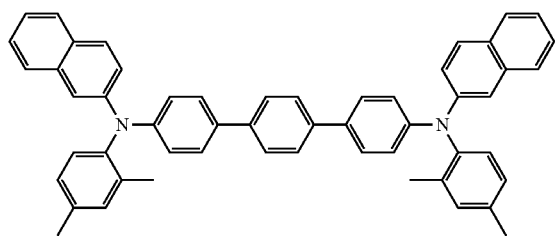
(17)
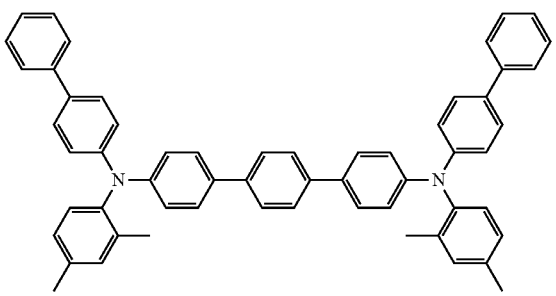
(18)
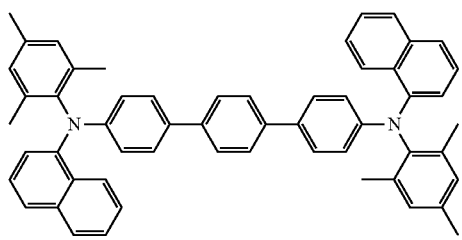
(19)
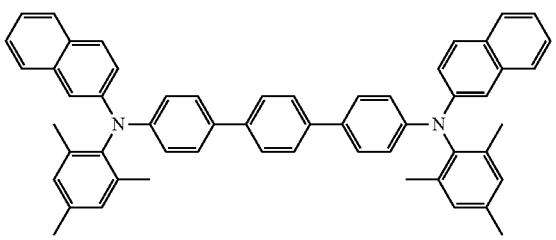
(20)
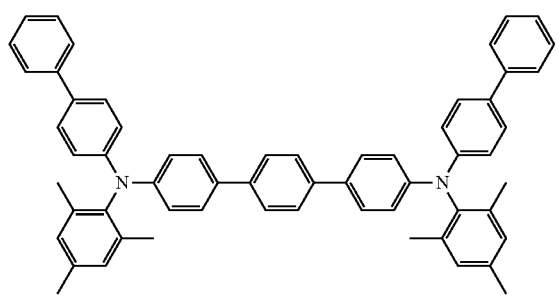
(25)
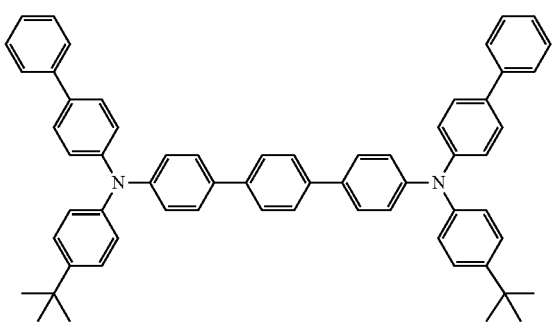
(27)
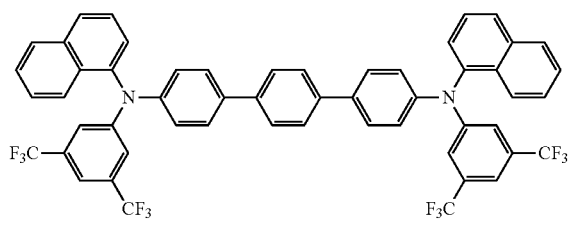
(28)
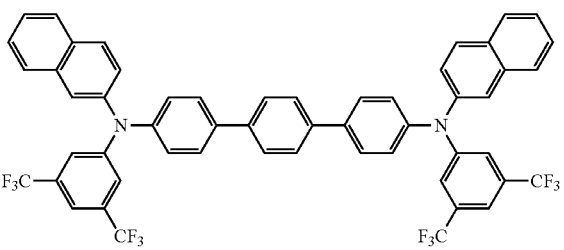

-continued
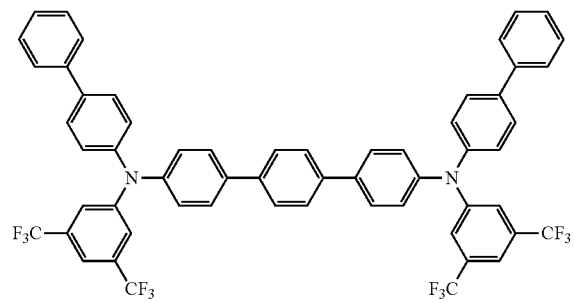
(29)
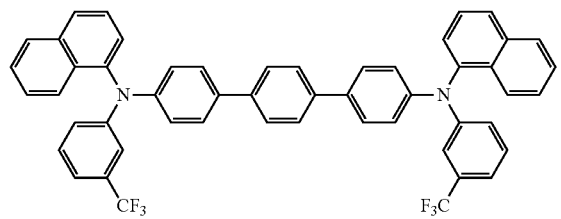
(30)
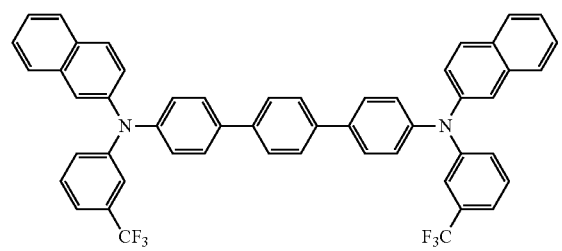
(31)
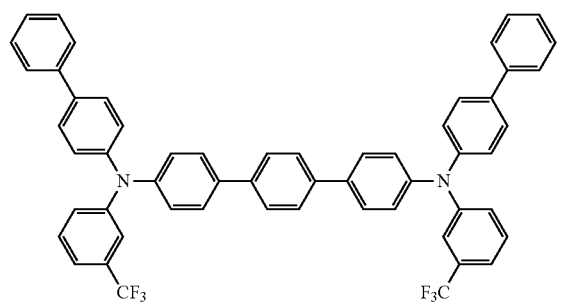
(32)
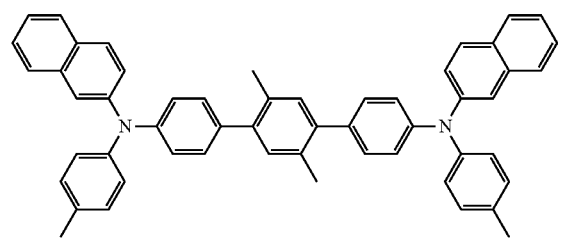
(34)
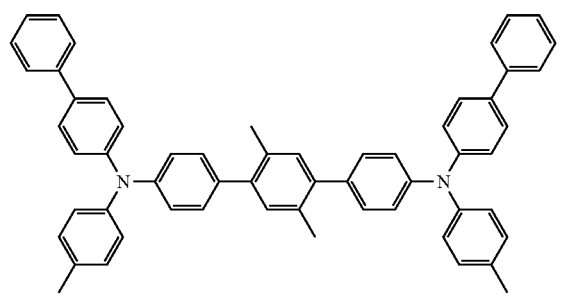
(35)
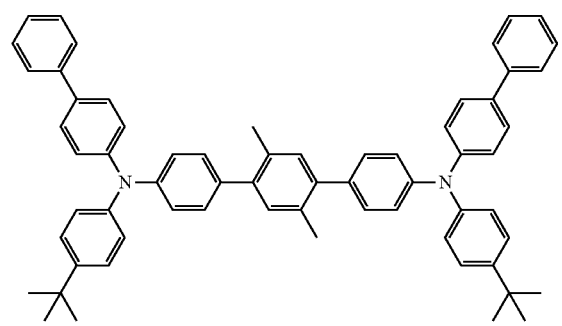
(36)
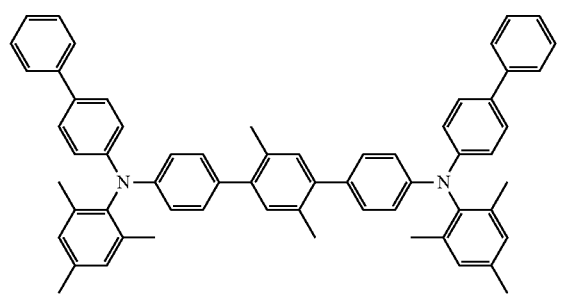
(37)
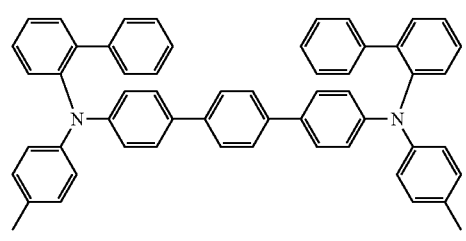
(38)
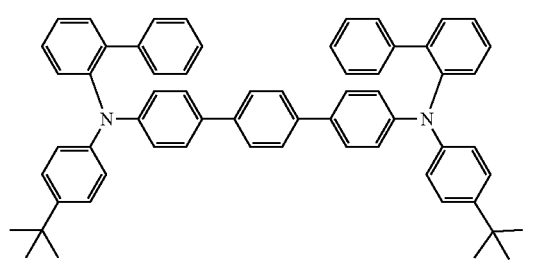
(39)

-continued
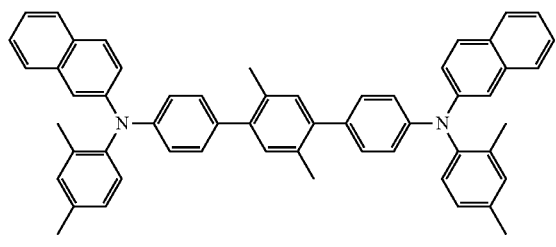
(42)
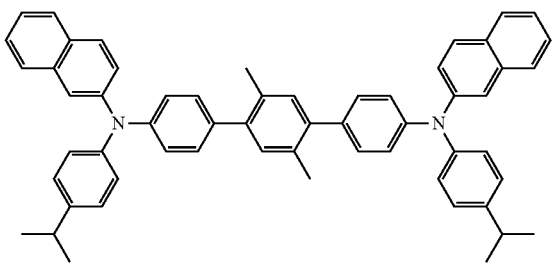
(43)
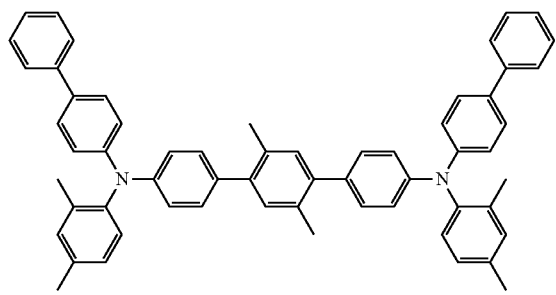
(44)
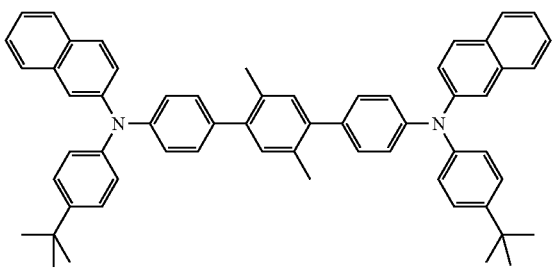
(45)
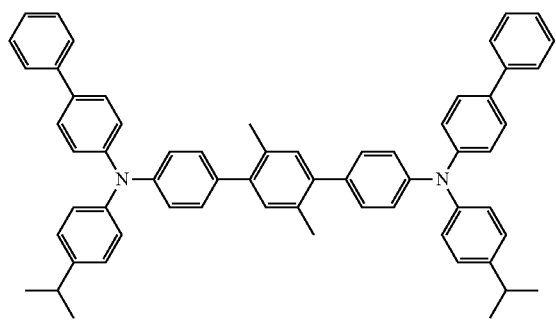
(46)
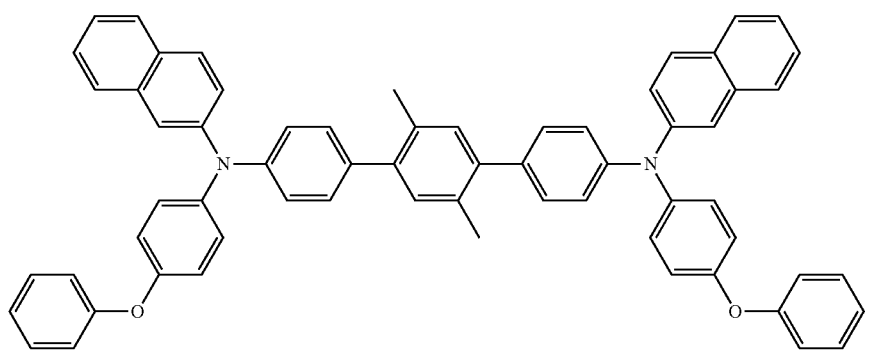
(47)

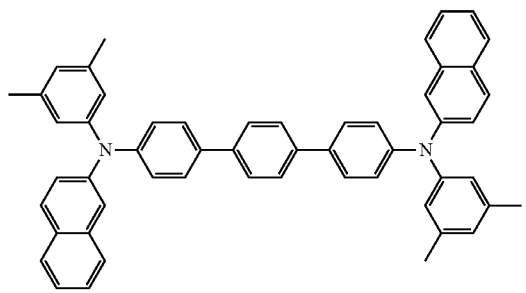
(48)

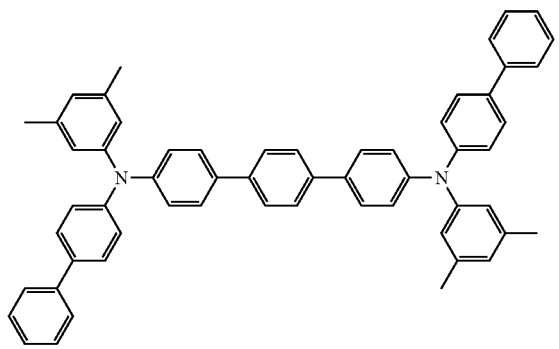
(49)

It has been found in particular that compounds with R2=alkyl demonstrate a much improved conductivity compared with known matrix materials, whereas compounds with R2=aryloxy were improved in respect of thermal stability.

Further features and advantages of the compounds and organic semiconducting components according to the invention will emerge from the following detailed description of preferred embodiments.

Selection of the Dopant

Preferred dopants are 3-radial compounds

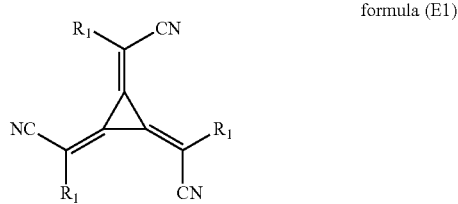
formula (E1)

wherein each $R_1$ in formula ($E_1$) is selected independently from aryl and heteroaryl, wherein aryl and heteroaryl are substituted at least in part, preferably completely, with electron-deficient groups (acceptor groups).

Aryl is preferably phenyl, biphenylyl, α-naphthyl, β-naphthyl, phenantryl or anthracyl.

Heteroaryl is preferably pyridyl, pyrimidyl, triazyl or quinoxalinyl.

Acceptor groups are electron-withdrawing groups, preferably selected from fluorine, chlorine, bromine, CN, trifluoromethyl or nitro.

The general synthesis is described in patent application EP1988587 under "Presentation of Oxocarbon, Pseudooxocarbon and Radial Structures".

Examples of acceptors that can be used as p-dopants include: 2,2,7,7-tetrafluoro-2,7-dihydro-1,3,6,8-dioxa-2,7-dibora-pentachloro-benzo[e]pyrene; 1,4,5,8-tetrahydro-1,4,5,8-tetrathia-2,3,6,7-tetracyanoanthraquinone; 1,3,4,5,7,8-hexafluoronaphtho-2,6-quinontetracyanomethane; 2,2'-(perfluoronaphthalen-2,6-diyliden)dimalononitrile (d3); 2,2'-(2,5-dibromo-3,6-difluorocyclo-hexa-2,5-dien-1,4-diyliden)dimalononitrile; 2,2',2"-(cyclopropan-1,2,3-triyliden)tris(2-(2,6-di-chloro-3,5-difluoro-4-(trifluoromethyl)phenyl)acetonitrile); 4,4',4"-cyclopropan-1,2,3-triyliden-tris(cyanomethan-1-yl-1-yliden)tris(2,3,5,6-tetrafluorobenzonitrile); 2,2',2"-(cyclopropane-1,2,3-triyliden)tris(2-(p-cyanotetrafluorophenyl)acetonitrile) (d1); 2,2',2"-(cyclopropane-1,2,3-triyliden)tris(2-(2,3,5,6-tetrafluoro-4-(trifluoromethyl)phenyl)-acetonitrile) (d2). Document DE 103 57 044 describes the use of quinoids and derivatives thereof as acceptors in organic semiconductor materials. Other dopants are described in US 2008/265216.

Doping Concentration

The dopant is present in a doping concentration of ≤1:1 to the matrix molecule, usually in a doping concentration of 1:2 or less, preferably of 1:5 or less, particularly preferably of 1:10 or less. The doping concentration may be limited in practice in the range from 1:1 to 1:10000.

Execution of the Doping

The doping of the respective matrix material with the p-dopants to be used in accordance with the invention can be produced by one of the following methods or a combination thereof:

a) mixed evaporation under vacuum with a source for the matrix material and a source for the dopant.

b) doping of a matrix layer by a solution of p-dopant with subsequent evaporation of the solvent, in particular by thermal treatment c) surface-doping of a matrix material layer by a layer of dopant applied to a surface d) production of a solution of matrix molecules and dopants and subsequent production of a layer from this solution by means of conventional methods, such as evaporation of the solvent or spin coating.

In this way, it is thus possible in accordance with the invention to produce p-doped layers of organic semiconductors, which can be used in a versatile manner. Mixed evaporation under vacuum (VTE) is preferred.

Overview of abbreviations occurring only in the examples

DSC—differential scanning calorimetry
HPLC—high performance liquid chromatography
MPLC medium pressure liquid chromatography
TLC—thin layer chromatography
GC—gas chromatography
NMR—nuclear magnetic resonance
MTBE—methyl-tert-butyl ether
SPS—solvent purification system
BINAP—2,2'-bis(diphenylphosphino)-1,1'-binaphthyl
UHV ultra-high vacuum
eq equivalent The purity specifications are given exclusively in "area %", that is to say is calculated in percentage of the area below the peak of the dominant substance in relation to the entire area of all peaks, integrated in the chromatogram.

Synthesis of the Compounds According to the Invention

1. Synthesis of the Secondary Amines, General Instructions

Scheme 1. General reaction scheme for the synthesis of secondary amines

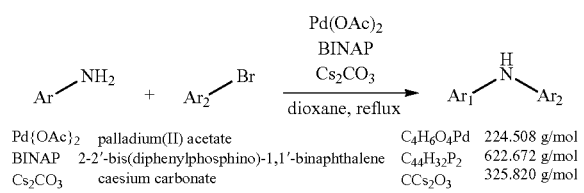

| | | |
|---|---|---|
| Pd{OAc}$_2$ | palladium(II) acetate | C$_4$H$_6$O$_4$Pd 224.508 g/mol |
| BINAP | 2-2'-bis(diphenylphosphino)-1,1'-binaphthalene | C$_{44}$H$_{32}$P$_2$ 622.672 g/mol |
| Cs$_2$CO$_3$ | caesium carbonate | CCs$_2$O$_3$ 325.820 g/mol |

1.1 General Synthesis Instructions

All procedures were performed in thoroughly heated glassware in an inert argon atmosphere. Commercially obtainable compounds were used in the acquired purities without additional preliminary purification steps, apart from the solvents, which were used in degassed and dried form.

A mixture of aryl bromide, aryl amine, palladium(II) acetate, BINAP and caesium carbonate in abs. dioxane (dried over sodium, degassed in argon stream over approximately 15 min) is stirred with reflux and maintaining an inert argon atmosphere until the TLC tracking indicates the practically complete reaction of the amine used in slight excess. The mixture is then cooled to room temperature, undissolved salts are removed via filtration where applicable, and the filtrate, following addition of methylene chloride (DCM, 100 mL), is then washed with water (to remove the base), 2 M HCl solution (to remove the starting material amine used in excess), saturated aqueous Na2CO3 solution (to regenerate the free amine from any hydrochloride formed) and again with water (for neutralisation). After drying the organic phase over MgSO4, this was concentrated under vacuum to dryness, and the residue was processed by means of gel filtration on silica gel or by means of flash chromatography on silica gel and was additionally purified where applicable by crystallisation from DCM/n-hexane and by washing processes (for example with boiling methanol).

1.1.1 Synthesis of N-(p-tolyl)-[1,1'-biphenyl]-4-amine (precursor to (6))

The synthesis was performed proceeding from the general instructions. 4-aminobiphenyl (20.78 g, 1.05 eq, 122.8 mmol), palladium(II) acetate (788 mg, 3.0 mol. %, 3.5 mmol), BINAP (3.28 g, 4.5 mol. %, 5.3 mmol), caesium carbonate (53.30 g, 1.4 eq, 163.7 mmol) and 4-bromotoluene (20.00 g, 1 eq, 116.9 mmol) were refluxed in dioxane (200 mL) at 130° C. over 3 days. Purification by column chromatography on silica gel (n-hexane/DCM=1:1) provided 11 g (36% yield, HPLC purity: 94%) of secondary amine. Prior to further reaction in the second stage, the product was combined by means of similarly pure fractions from other batches and was further purified via recrystallization from boiling methanol (end purity HPLC 99.7° M.

1.1.2 Synthesis of N-(p-tolyl)naphthalen-2-amine (precursor to (4))

The synthesis was performed proceeding from the general instructions. p-toluidine (10.87 g, 1.05 eq, 101.4 mmol), 2-bromonaphthalene (20.00 g, 96.6 mmol, 1 eq), palladium (II) acetate (651 mg, 2.9 mmol, 3.0 mol. %), BINAP (2.71 g, 4.4 mmol, 4.5 mol. %) and caesium carbonate (44.05 g, 135.2 mmol, 1.4 eq) were refluxed in dioxane (325 mL) at 130° C. over 3 days. Purification by column chromatography on silica gel (n-hexane/DCM=2:1) provided 17 g (75% yield, HPLC purity: >99.4%, GC purity: 100%) of secondary amine.

1.1.3 Synthesis of N-(4-methoxyphenyl)-[1,1'-biphenyl]-4-amine (precursor to (7))

The synthesis was performed proceeding from the general instructions. p-anisidine (11.64 g, 1.1 eq, 94.5 mmol), palladium(II) acetate (576 mg, 3.0 mol. %, 2.6 mmol), BINAP (2.4 g, 4.5 mol. %, 3.9 mmol), caesium carbonate (39.1 g, 1.4 eq, 120.0 mmol) and 4-bromobiphenyl (20.00 g, 1 eq, 85.8 mmol) were refluxed in dioxane (275 mL) at 125° C. over 4 days. Purification by column chromatography on silica gel (n-hexane/DCM=1:1) provided 17.0 g (72% yield, HPLC purity: >99.1%, GC purity: 100%) of secondary amine.

1.1.4 Synthesis of N-(p-tolyl)naphthalen-1-amine (precursor to (1))

The synthesis was performed proceeding from the general instructions. p-toluidine (10.10 g, 1.3 eq, 94.2 mmol), palladium(II) acetate (490 mg, 3.0 mol. %, 2.2 mmol), BINAP (2.03 g, 4.5 mol. %, 3.3 mmol), caesium carbonate (35.40 g, 1.5 eq, 108.7 mmol) and 1-naphthylbromide (15.00 g, 1.0 eq, 72.4 mmol) were refluxed in dioxane (210 mL) at 125° C. over 24 hours. Purification by column chromatography on silica gel (n-hexane/DCM=1:1) provided 12.7 g (76% yield, HPLC purity: 99.7%, GC purity: 100%) of secondary amine.

1.1.5 Synthesis of N-(4-methoxyphenyl)naphthalen-1-amine (precursor to (2))

The synthesis was performed proceeding from the general instructions. 1-bromonaphthalene (5.00 g, 24.1 mmol, 1 eq), palladium(II) acetate (160 mg, 0.73 mmol, 3.0 mol. %), caesium carbonate (11.80 g, 36.2 mmol, 1.5 eq), BINAP (0.88 g, 1.4 mmol, 4.5 mol. %) and p-anisidine (3.86 g, 31.4 mmol, 1.3 eq) were refluxed in dioxane (100 mL) at 125° C. over 24 hours. Purification by column chromatography on silica gel (n-hexane/DCM=1:1) provided 4.5 g (75% yield, HPLC purity 99.2%, GC purity: 100%) of secondary amine.

1.1.6 Synthesis of N-(4-methoxyphenyl)naphthalen-2-amine (precursor to (5))

The synthesis was performed proceeding from the general instructions. 2-bromonaphthalene (5.00 g, 1.2 eq, 24.2 mmol), palladium(II) acetate (136 mg, 3.0 mol. %, 0.60 mmol), caesium carbonate (9.18 g, 1.4 eq, 28.2 mmol), BINAP (564 mg, 4.5 mol. %, 0.91 mmol) and p-anisidine (2.48 g, 1.0 eq, 20.1 mmol) were refluxed in dioxane (100 mL) at 125° C. over 5 days. Purification by column chromatography on silica gel (n-hexane/DCM=1:1) following separation of insoluble salts via filtration without subsequent washing steps provided 3.3 g (66% yield, HPLC purity >97.9%, GC purity: 100%) of secondary amine.

1.1.7 Synthesis of N-(4-phenoxyphenyl)-[1,1'-biphenyl]-4-amine (precursor to (13))

The synthesis was performed proceeding from the general instructions. 4-bromobiphenyl (5.72 g, 1.0 eq, 24.5 mmol), 4-phenoxyaniline (5.00 g, 1.1 eq, 27.0 mmol), palladium(II) acetate (165 mg, 3.0 mol. %, 0.74 mmol), caesium carbonate (11.18 g, 1.4 eq, 34.3 mmol) and BINAP (686 mg, 4.5 mol. %, 1.1 mmol) were refluxed in dioxane (80 mL) at 125° C. over 5 days. Filtration for removal of insoluble constituents, washing and gel filtration over silica gel (n-hexane/DCM=1:2) provided 4.32 g (55% yield, HPLC purity >99.1%, GC purity 97.8%) of secondary amine.

1.1.8 Synthesis of N-([1,1'-biphenyl]-4-yl)naphthalen-1-amine (precursor to (8))

The synthesis was performed proceeding from the general instructions. 4-aminobiphenyl (12.83 g, 75.8 mmol, 1.3 eq), 1-naphthylbromide (12.07 g, 58.3 mmol, 1.0 eq), palladium (II) acetate (400 mg, 1.8 mmol, 3.0 mol. %), caesium carbonate (28.50 g, 87.5 mmol, 1.5 eq) and BINAP (1.65 g, 2.6 mmol, 4.5 mol. %) were refluxed in dioxane (210 mL) at 125° C. overnight. Purification by column chromatography on silica gel (n-hexane/DCM=1:1) provided 15.5 g (90% yield, HPLC purity >99.5%, GC purity 100%) of secondary amine.

1.1.9 Synthesis of N-([1,1'-biphenyl]-4-yl)naphthalen-2-amine (precursor to (9))

The synthesis was performed proceeding from the general instructions. 4-aminobiphenyl (15.95 g, 1.3 eq, 94.3 mmol), 2-naphthylbromide (15.00 g, 1.0 eq, 72.4 mmol), palladium (II) acetate (500 mg, 3.0 mol. %, 2.2 mmol), caesium carbonate (35.40 g, 1.5 eq, 108.6 mmol) and BINAP (2.05 g, 4.5 mol. %, 3.3 mmol) were refluxed in dioxane (210 mL) overnight (T=125° C.). After gel filtration on silica gel (DCM) and washing, there remained 24.23 g (113%) of raw product, which was purified by means of column chromatography on silica gel (n-hexane/DCM=1:1). 18.2 g (85% yield, HPLC purity >99.8%, GC purity 100%) of secondary amine were obtained.

1.1.10 Synthesis of N-(4-(tert-butyl)phenyl)naphthalen-2-amine (precursor to (11))

The synthesis was performed proceeding from the general instructions. 2-naphthylbromide (3.00 g, 14.5 mmol, 1.0 eq), palladium(II) acetate (98 mg, 0.44 mmol, 3.0 mol. %), caesium carbonate (7.09 g, 21.8 mmol, 1.5 eq), BINAP (0.41 g, 0.65 mmol, 4.5 mol. %) and 4-(tert-butyl)aniline (2.69 g, 18.8 mmol, 1.3 eq) were refluxed in dioxane (80 mL) overnight in the dark (T=125° C.). After washing, gel filtration over silica gel (then rinsed with DCM/n-hexane=1:1) and treatment of the residue obtained from the filtrate in vacuo with n-hexane in an ultrasonic bath, there remained 1.83 g (46% yield, HPLC purity 99.4%, GC purity 100%) of secondary amine as a white solid.

1.1.11 Synthesis of N-(4-phenoxyphenyl)naphthalen-2-amine (precursor to (12))

The synthesis was performed proceeding from the general instructions. 2-bromonaphthalene (3.00 g, 1.0 eq, 14.5 mmol), 4-phenoxyaniline (3.48 g, 1.3 eq, 18.8 mmol), palladium(II) acetate (98 mg, 3.0 mol. %, 0.44 mmol), caesium carbonate (7.09 g, 1.5 eq, 21.8 mmol) and BINAP (0.48 g, 4.5 mol. %, 0.65 mmol) were refluxed in dioxane (80 mL) overnight (T=125° C.). After filtration, washing and gel filtration over silica gel (DCM/n-hexane=1:1), 2.8 g of secondary amine (62% yield, HPLC purity: 99.4%, GC purity: 100%) were obtained.

1.1.12 Synthesis of N-(4-(tert-butyl)phenyl)-[1,1'-biphenyl]-4-amine (precursor to (25))

The synthesis was performed proceeding from the general instructions. 4-bromobiphenyl (5.00 g, 1.0 eq, 21.5 mmol), 4-(tert-butyl)aniline (3.84 g, 1.2 eq, 25.7 mmol), palladium (II) acetate (145 mg, 3.0 mol. %, 0.65 mmol), caesium carbonate (14.00 g, 2.0 eq, 43.0 mmol) and BINAP (0.60 g (4.5 mol. %, 0.96 mmol) were refluxed in dioxane (65 mL) over 6 days in the dark (T=125° C.). Gel filtration over silica gel (DCM), washing, extraction by stirring with n-hexane and subsequent purification by column chromatography on silica gel (DCM/n-hexane=1:2) provided 2.41 g diamine (37% yield, HPLC purity 100%, GC purity: 100%) as a white solid.

1.1.13 Synthesis of N-(p-tolyl)-[1,1'-biphenyl]-2-amine (precursor to (38))

The synthesis was performed proceeding from the general instructions. 2-bromobiphenyl (3.00 g, 1.0 eq, 12.9 mmol), p-toluidine (1.65 g, 1.2 eq, 15.4 mmol), palladium(II) acetate (140 mg, 4.8 mol. %, 0.62 mmol), caesium carbonate (6.30 g, 1.5 eq, 19.4 mmol) and BINAP (410 mg, 5.1 mol. %, 0.66 mmol) were refluxed in dioxane (65 mL) over 5 days (T=125° C.). Addition of water, extraction with DCM and removal of methanol-insoluble constituents from the residue remaining following removal of the solvent provided 4.16 g of raw product. Besides unreacted 2-bromobiphenyl (2.03 g, 68% of the used quantity, HPLC purity 98.7%), purification by column chromatography on silica gel (DCM/n-hexane=1:5) also provided the desired secondary amine (0.99 g, 30% yield, HPLC purity 99.7%, GC purity 100%) as yellow oil with honey-like consistency.

1.1.14 Synthesis of N-(2,4-dimethylphenyl)-[1,1'-biphenyl]-4-amine (precursor to (17))

The synthesis was performed proceeding from the general instructions. 4-bromobiphenyl (19.95 g, 1.0 eq, 85.6 mmol), 2,4-dimethylaniline (13.48 g, 1.3 eq, 111.3 mmol), palladium(II) acetate (0.59 g, 3.0 mol. %, 2.57 mmol), caesium carbonate (41.80 g, 1.5 eq, 128.4 mmol) and BINAP (2.42 g, 4.5 mol. %, 3.85 mmol) were refluxed in dioxane (210 mL) over 88 hours (T=125° C.). Gel filtration on silica gel (DCM), washing in accordance with the general synthesis instructions and concentration to dryness provided 26.44 g (113% yield) of raw product. Purification by column chromatography on silica gel (DCM/n-hexane=1:5) and washing with methanol led to 16.43 g of secondary amine (70% yield, HPLC purity >99.5%).

1.1.15 Synthesis of N-(2,4-dimethylphenyl)naphthalen-2-amine (precursor to (16))

The synthesis was performed proceeding from the general instructions. 2-bromonaphthalene (5.00 g, 1.0 eq, 24.2 mmol), 2,4-dimethylaniline (3.07 g, 1.05 eq, 25.4 mmol), palladium(II) acetate (163 mg, 3.0 mol. %, 0.72 mmol), caesium carbonate (11.02 g, 1.4 eq, 33.8 mmol) and BINAP (677 mg, 4.5 mol. %, 1.09 mmol) were refluxed in dioxane (50 mL) overnight (T=125° C.). Gel filtration on silica gel (DCM), washing in accordance with the general synthesis instructions and concentration to dryness provided approximately 7 g (119% yield) of raw product. Purification by column chromatography on silica gel (DCM/n-hexane=1:4) provided two fractions measuring 2.53 g (43% yield, HPLC purity 99.6%) and 2.60 g (44% yield, HPLC purity 97.8%) of secondary amine. The first fraction was reacted further in the next stage without further purification.

1.1.16 Synthesis of N-(4-isopropylphenyl)naphthalen-2-amine (precursor to (10))

The synthesis was performed proceeding from the general instructions. 2-bromonaphthalene (6.00 g, 1.0 eq, 29.0 mmol), 4-isopropylaniline (3.48 g, 1.3 eq, 37.6 mmol), palladium(II) acetate (195 mg, 3.0 mol. %, 0.87 mmol), caesium carbonate (14.18 g, 1.5 eq, 43.5 mmol) and BINAP (0.82 g, 4.5 mol. %, 1.3 mmol) were refluxed in dioxane (160 mL) over 48 hours (T=125° C.). Filtration for removal of insoluble constituents, washing in accordance with the general synthesis instructions and concentration to dryness, followed by purification by column chromatography on silica gel (DCM/n-hexane=1:1) provided a light-grey solid raw product. This was received in n-hexane, treated in ultrasonic bath and isolated via filtration, washed with n-hexane and dried. 3.75 g (yield 50%, HPLC purity 99.1%) of secondary amine were obtained as white solid.

1.1.17 Synthesis of N-(m-tolyl)naphthalen-2-amine (precursor to (21))

The synthesis was performed proceeding from the general instructions. 2-bromonaphthalene (5.00 g, 1.0 eq, 24.2 mmol), m-toluidine (2.72 g, 1.05 eq, 25.4 mmol), palladium (II) acetate (162 mg, 3.0 mol. %, 0.73 mmol), caesium carbonate (11.02 g, 1.4 eq, 33.8 mmol) and BINAP (677 mg, 4.5 mol. %, 1.09 mmol) were refluxed in dioxane (50 mL) overnight (T=125° C.). Gel filtration on silica gel (DCM), washing in accordance with the general synthesis instructions and concentration to dryness delivered approximately 7 g (125% yield) of raw product. Purification by column chromatography on silica gel (gradient DCM/n-hexane=1:4→DCM/n-hexane=1:1) provided 3.3 g (yield 59%, HPLC purity 99.8%) of secondary amine for direct further reaction in the next stage.

1.1.18 Synthesis of N-mesityl-[1,1'-biphenyl]-4-amine (precursor to (20))

The synthesis was performed proceeding from the general instructions. 4-bromobiphenyl (18.75 g, 1.0 eq, 80.5 mmol), 2,4,6-trimethylaniline (14.10 g, 1.3 eq, 104.6 mmol), palladium(II) acetate (0.55 g, 3.0 mol. %, 2.45 mmol), caesium carbonate (39.30 g, 1.5 eq, 120.7 mmol) and BINAP (1.75 g, 3.5 mol. %, 2.79 mmol) were refluxed in dioxane (210 mL) over 2 days (T=125° C.). Gel filtration on silica gel (DCM), washing in accordance with the general synthesis instructions and concentration to dryness provided 27.5 g (119% yield) of raw product. Purification by column chromatography on silica gel (gradient DCM/n-hexane=1:2) and treatment of the isolated fractions with methanol in an ultrasonic bath provided 12.4 g (53% yield, HPLC purity >89%) of secondary amine. Recrystallisation from boiling methanol lead to two fractions measuring 3 g (13% yield, HPLC purity 97.7%, GC-MS purity 100%) and 4.9 g (21% yield, HPLC purity 93.3%). The first fraction was reacted further in the next stage without further purification.

1.1.19 Synthesis of N-(3,5-bis(trifluoromethyl)phenyl)naphthalen-2-amine (precursor to (28))

The synthesis was performed proceeding from the general instructions. 2-bromonaphthalene (5.00 g, 1.0 eq, 24.2 mmol), 3,5-bis(trifluoromethyl)aniline (5.81 g, 1.05 eq, 25.4 mmol), palladium(II) acetate (163 mg, 3.0 mol. %, 0.72 mmol), caesium carbonate (11.02 g, 1.4 eq, 33.8 mmol) and BINAP (677 mg, 4.5 mol. %, 1.09 mmol) were refluxed in dioxane (50 mL) overnight (T=125° C.). Gel filtration on silica gel (DCM), washing in accordance with the general synthesis instructions and concentration to dryness as well as purification by column chromatography (DCM/n-hexane=1:2) of the obtained raw product on silica gel provided 6.40 g (75% yield, HPLC purity 99.3%) of secondary amine.

1.1.21 Synthesis of N-(m-tolyl)naphthalen-1-amine (precursor to (22))

The synthesis was performed proceeding from the general instructions. 1-bromonaphthalene (5.00 g, 1.0 eq, 24.2 mmol), m-toluidine (2.72 g, 1.05 eq, 25.4 mmol), palladium (II) acetate (162 mg, 3.0 mol. %, 0.73 mmol), caesium carbonate (11.02 g, 1.4 eq, 33.8 mmol) and BINAP (677 mg, 4.5 mol. %, 1.09 mmol) were refluxed in dioxane (50 mL) overnight (T=125° C.). Gel filtration on silica gel (DCM), washing in accordance with the general synthesis instructions and concentration to dryness provided approximately 7 g (111% yield) of raw product. Purification by column chromatography on silica gel (DCM/n-hexane=1:1) provided 5.4 g of secondary amine (95% yield, HPLC purity >99.0%) for further reaction in the next stage.

1.1.22 Synthesis of N-(3,5-dimethylphenyl)naphthalen-2-amine (precursor to (48))

The synthesis was performed proceeding from the general instructions. 2-bromonaphthalene (25 g, 1.0 eq, 120.7 mmol), palladium(II) acetate (813 mg, 3.0 mol. %, 3.62 mmol), BINAP (3.38 g, 4.5 mol. %, 5.43 mmol), caesium carbonate (58.98 g, 1.5 eq, 181.0 mmol) and 3,5-dimethylaniline (15.36 g, 1.05 eq, 126.7 mmol) were refluxed in dioxane (250 mL) at 125° C. over 19 hours. Purification by column chromatography on silica gel (n-hexane/DCM=2:1) provided 15.1 g (50% yield, HPLC purity: 99.9%) of secondary amine.

1.1.23 Synthesis of N-(3,5-dimethylphenyl)-[1,1'-biphenyl]-4-amine (precursor to (49))

The synthesis was performed proceeding from the general instructions. 4-bromobiphenyl (20 g, 1.0 eq, 85.8 mmol), palladium(II) acetate (578 mg, 3.0 mol. %, 2.57 mmol), BINAP (2.40 g, 4.5 mol. %, 3.86 mmol), caesium carbonate (39.1 g, 1.4 eq, 120.1 mmol) and 3,5-dimethylaniline (10.92 g, 1.05 eq, 90.1 mmol) were refluxed in dioxane (200 mL) at 125° C. over 44 hours. Purification by column chromatography on silica gel (n-hexane/DCM=2:1) and washing in methanol delivered 15.6 g (66% yield, HPLC purity: 99.5%) of secondary amine.

1.2 Characterisation Data

1.2.1 Characterisation of N-(p-tolyl)-[1,1'-biphenyl]-4-amine (precursor to (6))

TLC (reversal phase, MeCN/water=9:1): Rf=0.38
TLC (silica gel, DCM/n-hexane=3:8): Rf=0.28
DSC: melting point: 133° C. (onset), unsublimated material
1H-NMR (CD2Cl2 referenced to 5.31 ppm, 500.13 MHz): δ [ppm]=2.31 ppm (s, 3H, Me), 5.79 (s, 1H, NH), 7.04 ("d", J=8.5 Hz, 2H), 7.07 ("d", J=8.5 Hz, 2H), 7.11 ("d", J=8.5 Hz, 2H), 7.28 ("t", J=7.5 Hz, 1H, biphenyl H-4'), 7.40 ("t", J=7.5 Hz, 2H, biphenyl H-3'), 7.50 ("d", J=8.5 Hz, 2H), 7.57 ("d", J=7.5 Hz, 2H, biphenyl H-2').
13C-NMR (CD2Cl2 referenced to 53.73 ppm, 125.76 MHz): δ [ppm]=20.69 (q, CH3), 117.00 (d), 119.24 (d), 126.58 (d), 126.75 (d), 128.08 (d), 129.01 (d), 130.13 (d), 131.49 (s), 133.01 (s), 140.36 (s), 141.10 (s), 143.81 (s).

1.2.2 Characterisation of N-(p-tolyl)naphthalen-2-amine (precursor to (4))

TLC (silica gel, DCM/n-hexane 2:3): Rf=0.39
DSC: melting point: 101° C. (onset), unsublimated material
1H-NMR (CDCl3 referenced to 7.26 ppm, 500.13 MHz): δ [ppm]=2.36 (s, 3H, Me), 5.78 (br.s, 1H, NH), 7.11 ("d" with discernible fine splitting, J=8.5 Hz, 2H, tolyl-H), 7.16 ("d", J=8.5 Hz, 2H, tolyl-H), 7.19 ("dd", J=8.5 Hz, 2.0 Hz, 1H, H-3), 7.30 ("t" with discernible fine splitting, J=8.0 Hz, 1H, H-6), 7.39 ("d", J=2.0 Hz, 1H, H-1), 7.42 ("t" with discernible fine splitting, J=8.0 Hz, 1H, H-7), 7.64 ("d", J=8.0 Hz, 1H, H-4 or H-5 or H-8), 7.74 ("d", J=8.5 Hz, 1H, H-4 or H-5 or H-8), 7.75 ("d", J=8.5 Hz, 1H, H-4 or H-5 or H-8).
13C-NMR (CDCl3 referenced to 77.0 ppm, 125.76 MHz): δ [ppm]=20.71 (q, CH3), 110.28 (d), 119.32 (d, tolyl-CH), 119.54 (d), 123.14 (d), 126.33 (d), 126.36 (d), 127.59 (d), 128.85 (s), 129.08 (d), 129.91 (d, tolyl-CH), 131.34 (s), 134.69 (s), 140.05 (s), 141.66 (s).

| Elemental analysis: | ber. values | C 87.52%, H 6.48%, N 6.06% |
| | exp. values | C 87.48%, H 6.61%, N 6.01% |

1.2.3 Characterisation of N-(4-methoxyphenyl)-[1,1'-biphenyl]-4-amine (precursor to (7))

TLC (silica gel, DCM/n-hexane=1:2): Rf=0.18
DSC: melting point: 124° C. (onset), unsublimated material
1H-NMR (CDCl3 referenced to 7.26 ppm, 500.13 MHz): δ [ppm]=The spectrum indicates a strong dynamic effect, which results in broadly propagated signals in part. 3.82 (br. s, 3H, MeO), 5.57 (very broad s, 1H, NH), 6.89 ("d", J=8.5 Hz, 2H), 6.98 very broad s, 2H), 7.11 (very broad s, 2H), 7.28 (br. m, triplet-like splitting, 1H, p-Ph), 7.41 ("t", J=7.5 Hz, 2H, m-Ph), 7.47 (br. s, 2H), 7.55 (br. d, J=6.5 Hz, 2H).
13C-NMR (CDCl3 referenced to 77.0 ppm, 125.76 MHz): δ [ppm]=55.53 (q, OCH3), 114.69 (d), 115.73 (d), 122.39 (d), 126.33 (d), 126.37 (d), 127.91 (d), 128.66 (d), 132.41 (s), 135.42 (s), 140.95 (s), 144.56 (s), 155.41 (s, 0-bound).

| Elemental analysis: | ber. values | C 82.88%, H 6.22%, N 5.09%, O 5.81%. |
| | exp. values | C 82.42%, H 6.29%, N 5.13%, O 6.23%. |

1.2.4 Characterisation of N-(p-tolyl)naphthalen-1-amine (precursor to (1))

TLC (silica gel, DCM/n-hexane=1:4): Rf=0.39
DSC: melting point: 77° C. (onset), unsublimated material
1H-NMR (CD2Cl2 referenced to 5.31 ppm, 500.13 MHz): δ [ppm]=2.29 (s, 3H, CH3), 5.98 (br. s, 1H, NH), 6.94 ("d", J=8.5 Hz, 2H, tolyl), 7.08 ("d", J=8.5 Hz, 2H, tolyl), 7.26 ("d", J=7.5 Hz, 1H, naphthyl), 7.35 ("t", J=7.5 Hz, 1H, naphthyl), 7.45-7.50 (m, 3H, naphthyl), 7.85 ("dd", J=7.5 Hz, 2.5 Hz, 1H, naphthyl), 7.99 ("d" with discernible fine splitting, J=7.5 Hz, 1H, naphthyl).
13C-NMR (CD2Cl2 referenced to 53.73 ppm, 125.76 MHz): δ [ppm]=20.66 (q, Me), 114.14 (d, naphthyl C-2), 118.79 (d, tolyl), 121.77 (d, naphthyl), 122.13 (d, naphthyl), 125.74 (d, naphthyl), 126.33 (d, naphthyl), 126.39 (d, naphthyl), 127.28 (s), 128.77 (d, naphthyl), 130.11 (d, tolyl), 130.85 (s), 135.04 (s), 140.04 (s, N-bound), 142.11 (s, N-bound).

1.2.5 Characterisation of N-(4-methoxyphenyl)naphthalen-1-amine (precursor to (2))

TLC (silica gel, DCM/n-hexane=1:1): Rf=0.38
DSC: melting point: 111° C. (onset), unsublimated material
1H-NMR (CD2Cl2 referenced to 5.31 ppm, 500.13 MHz): δ [ppm]=2.29 (s, 3H, CH3), 5.98 (br. s, 1H, NH), 6.94 ("d", J=8.5 Hz, 2H, tolyl), 7.08 ("d", J=8.5 Hz, 2H, tolyl), 7.26 ("d", J=7.5 Hz, 1H, naphthyl), 7.35 ("t", J=7.5 Hz, 1H, naphthyl), 7.45-7.50 (m, 3H, naphthyl), 7.85 ("dd", J=7.5 Hz, 2.5 Hz, 1H, naphthyl), 7.99 ("d" with discernible fine splitting, J=7.5 Hz, 1H, naphthyl).
13C-NMR (CD2Cl2 referenced to 53.73 ppm, 125.76 MHz): δ [ppm]=20.66 (q, Me), 114.14 (d, naphthyl C-2), 118.79 (d, tolyl), 121.77 (d, naphthyl), 122.13 (d, naphthyl), 125.74 (d, naphthyl), 126.33 (d, naphthyl), 126.39 (d, naphthyl), 127.28 (s), 128.77 (d, naphthyl), 130.11 (d, tolyl), 130.85 (s), 135.04 (s), 140.04 (s, N-bound), 142.11 (s, N-bound).

1.2.6 Characterisation of N-(4-methoxyphenyl)naphthalen-2-amine (precursor to (5))

TLC (silica gel, DCM/n-hexane=1:1): Rf=0.60
DSC: melting point: 103° C. (onset), unsublimated material
1H-NMR (CDCl3 referenced to 7.26 ppm, 500.13 MHz): δ [ppm]=3.83 (s, 3H, OMe), 5.68 (br. s, 1H, NH), 6.92 ("d" with fine splitting, J=9.0 Hz, 2H, phenylene), 7.12 ("dd" J=8.5 Hz, 2.5 Hz, 1H, naphthyl H-5 or H-8), 7.17 ("d" with fine splitting, J=9.0 Hz, 2H, phenylene), 7.22 ("d", J=3.0 Hz, 1H, naphthyl H-1), 7.25 ("t" with fine splitting, J=8.0 Hz, 1H, naphthyl H-6 or H-7), 7.37 ("t" with fine splitting, J=8.0 Hz, 1H, naphthyl H-6 or H-7), 7.59 ("d", J=8.0 Hz, 1H, naphthyl H-3 or H-4), 7.70 ("d", J=9.0 Hz, 1H, naphthyl H-5 or H-8), 7.71 ("d", J=8.0 Hz, 1H, naphthyl H-3 or H-4).

13C-NMR (CDCl3 referenced to 77.00 ppm, 125.76 MHz): δ [ppm]=55.56 (q, OMe), 108.76 (d, naphthyl), 114.72 (d, phenylene), 118.86 (d, naphthyl), 122.56 (d, phenylene), 122.84 (d, naphthyl), 126.20 (d, naphthyl), 126.36 (d, naphthyl), 127.59 (d, naphthyl), 128.52 (s), 129.11 (d, naphthyl), 134.77 (s), 135.47 (s), 142.88 (s, CAr—N), 155.52 (s, CAr—O).

1.2.7 Characterisation of N-(4-phenoxyphenyl)[1,1'-biphenyl]-4-amine (precursor to (13))

TLC (silica gel, DCM/n-hexane=2:1): Rf=0.76

DSC: melting point: 137° C. (onset), unsublimated material

1H-NMR (CDCl3 referenced to 7.26 ppm, 500.13 MHz): δ [ppm]=5.69 (br. s, 1H, NH), 6.98-7.02 (m, 4H), 7.08 ("t", J=7.5 Hz, 1H, p-Ph), 7.08 ("d", J=8.5 Hz, 2H), 7.13 ("dt", J=9.0 Hz, 2.5 Hz, 2H), 7.30 ("t", J=7.5 Hz, 1H, p-Ph), 7.33 ("t" with fine splitting, J=8.0 Hz, 2H, m-Ph), 7.42 ("t", J=8.0 Hz, 2H, m-Ph), 7.51 ("dt", J=9.0 Hz, 2.5 Hz, 2H), 7.57 ("dd", J=8.0 Hz, 1.0 Hz, 2H, o-Ph).

13C-NMR (CDCl3 referenced to 77.00 ppm, 125.76 MHz): δ [ppm]=116.83 (br.), 117.98 (d), 120.49, 120.63, 122.68 (d), 126.47 (d), 126.51 (d), 127.98 (br.), 128.71 (d), 129.65 (d), 133.2 (very broad), 138.4 (very broad), 140.82 (br.), 143.3 (very broad), 151.4 (very broad), 158.08 (s, i-Ph, 0-bound). There would appear to be a type of dynamic effect, resulting in broadly propagated signals.

1.2.8 Characterisation of N-([1,1'-biphenyl]-4-yl)naphthalen-1-amine (precursor to (8))

TLC (silica gel, DCM/n-hexane=1:1): Rf=0.75

DSC: melting point: 150° C. (onset), unsublimated material

1H-NMR (CD2Cl2 referenced to 5.31 ppm, 500.13 MHz): δ [ppm]=6.12 (br. s, 1H, NH), 7.06 ("d" with fine splitting, J=8.5 Hz, 2H, phenylene), 7.28 ("t", J=7.5 Hz, 1H, p-Ph), 7.39-7.43 (m, 4H, m-Ph, 2× naphthyl), 7.51 (high symm. m, 2H, naphthyl), 7.51 ("d" with fine splitting, J=8.5 Hz, 2H, phenylene), 7.57 ("dd", J=8.5 Hz, 1.0 Hz, 2H, o-Ph), 7.60 (m, 1H, naphthyl), 7.89 (in, duplet-like splitting, 1H, naphthyl), 8.04 (m, duplet-like splitting, 1H, naphthyl).

13C-NMR (CD2Cl2 referenced to 53.73 ppm, 125.76 MHz): δ [ppm]=116.59 (d, naphthyl), 117.60 (d, phenylene), 122.11 (d, naphthyl or p-Ph), 123.43 (d, naphthyl or p-Ph), 126.03 (d, naphthyl or p-Ph), 126.35 (d, naphthyl or p-Ph), 126.46 (d, naphthyl or p-Ph), 126.63 (d, phenylene), 126.81 (d, naphthyl or p-Ph), 128.12 (d, phenylene), 128.18 (s), 128.80 (d, naphthyl or p-Ph), 129.03 (d, phenylene), 133.29 (s), 135.08 (s), 138.83 (s), 141.10 (s, CAr—N), 144.73 (s, CAr—N).

1.2.9 Characterisation of N-([1,1'-biphenyl]-4-yl)naphthalen-2-amine (precursor to (9))

TLC (silica gel, DCM/n-hexane=1:1): Rf=0.46

DSC: melting point: 146° C. (onset), unsublimated material

1H-NMR (CD2Cl2 referenced to 5.31 ppm, 500.13 MHz): δ [ppm]=6.08 (br. s, 1H, NH), 7.25 ("d" with fine splitting, J=8.5 Hz, 2H, phenylene), 7.28-7.32 (m, 3H), 7.39-7.44 (m, 3H), 7.50 ("d", J=2.0 Hz, 1H, naphthyl H-1), 7.57 ("d" with fine splitting, J=9.0 Hz, 2H, phenylene), 7.60 ("dd", J=8.0 Hz, 1.0 Hz, 2H, o-Ph), 7.67 ("d", J=8.5 Hz, 1H, naphthyl), 7.76 ("t", J=9.0 Hz, 2H, m-Ph).

13C-NMR (CD2Cl2 referenced to 53.73 ppm, 125.76 MHz): δ [ppm]=111.75 (d, naphthyl), 118.46 (d, biphenyl), 120.35 (d, naphthyl or p-Ph), 123.82 (d, naphthyl or p-Ph), 126.71 (d, biphenyl), 126.74 (d, naphthyl or p-Ph), 126.77 (d, naphthyl or p-Ph), 126.96 (d, naphthyl or p-Ph), 127.88 (d, naphthyl or p-Ph), 128.20 (d, biphenyl), 129.07 (d, biphenyl), 129.45 (d, naphthyl or p-Ph), 129.54 (s), 134.19 (s), 134.96 (s), 140.99 (s), 141.00 (s), 142.66 (s, CAr—N).

1.2.10 Characterisation of N-(4-(tert-butyl)phenyl)naphthalen-2-amine (precursor to (11))

TLC (silica gel, DCM/n-hexane=1:2): Rf=0.47

DSC: melting point: 77° C. (onset), unsublimated material, 2 peaks arranged closely together obtained 1H-NMR (CD2Cl2 referenced to 5.31 ppm, 500.13 MHz): δ [ppm]=1.32 (s, 9H, CH3), 5.92 (br. S, 1H, NH), 7.13 ("d" with fine splitting, J=8.5 Hz, 2H, phenylene), 7.19 ("dd", J=9.0 Hz, 2.0 Hz, 1H, naphthyl H-3 or H-4), 7.26 ("t" with fine splitting, J=8.0 Hz, 1H, naphthyl H-6 or H-7), 7.34 ("d" with fine splitting, J=8.5 Hz, 2H, phenylene), 7.38 ("t" with fine splitting, J=8.5 Hz, 1H, naphthyl H-6 or H-7), 7.39 ("d", J=1.5 Hz, 1H, naphthyl H-1), 7.62 ("d", J=8.5 Hz, 1H, naphthyl H-5 or H-8), 7.72 (2×"d" overlapped, J=9.0 Hz, 2H, naphthyl H-3 and/or H-4 and/or H-5 and/or H-8).

13C-NMR (CD2Cl2 referenced to 53.73 ppm, 125.76 MHz): δ [ppm]=31.50 (q, Me), 34.41 (s, CMe3), 110.15 (d, naphthyl), 118.85 (d, phenylene), 119.87 (d, naphthyl), 123.39 (d, naphthyl), 126.49 (d, phenylene), 126.56 (d, naphthyl), 126.67 (d, naphthyl), 127.84 (d, naphthyl), 129.15 (s), 129.32 (d, naphthyl), 135.06 (s), 140.32 (s), 141.95 (s), 145.01 (s, CAr—N).

1.2.11 Characterisation of N-(4-phenoxyphenyl)naphthalen-2-amine (precursor to (12))

TLC (silica gel, DCM/n-hexane=1:1): Rf=0.35

DSC: melting point: 98° C. (onset), unsublimated material

1H-NMR (CD2Cl2 referenced to 5.31 ppm, 500.13 MHz): δ [ppm]=5.91 (br. s, 1H, NH), 7.00 ("d" with fine splitting, J=8.5 Hz, 4H, phenylene and/or o-Ph), 7.07 ("t", J=7.5 Hz, 1H, p-Ph), 7.18 (m, coupling pattern unclear due to signal overlap, 1H, naphthyl), 7.19 ("d" with fine splitting, J=9.0 Hz, 2H, phenylene and/or o-Ph), 7.27 ("td", J=8.0 Hz, 1.0 Hz, 1H, naphthyl H-6 or H-7), 7.33 ("t" with fine splitting, J=8.0 Hz, 2H, m-Ph), 7.36 ("d", 2.5 Hz, 1H, naphthyl H-1), 7.38 ("td", J=8.0 Hz, 1.0 Hz, 1H, naphthyl H-6 or H-7), 7.63 ("d", J=8.0 Hz, 1H, naphthyl), 7.72 ("d", J=8.0 Hz, 1H, naphthyl), 7.73 ("d", J=8.5 Hz, 1H, naphthyl).

13C-NMR (CD2Cl2 referenced to 53.73 ppm, 125.76 MHz): δ [ppm]=110.11 (d, naphthyl), 118.25 (d, phenylene), 119.68 (d, naphthyl or p-Ph), 120.78 (d, phenylene), 121.07 (d, phenylene), 123.01 (d, naphthyl or p-Ph), 123.49 (d, naphthyl or p-Ph), 126.57 (d, naphthyl or p-Ph), 126.74 (d, naphthyl or p-Ph), 127.86 (d, naphthyl or p-Ph), 129.19 (s), 129.43 (d, naphthyl or p-Ph), 129.98 (d, phenylene), 135.05 (s), 138.86 (s), 142.13 (s, CAr—N), 151.82 (s, CAr—O), 158.48 (s, CAr—O).

1.2.12 Characterisation of N-(4-(tert-butyl)phenyl)[1,1'-biphenyl]-4-amine (precursor to (25))

TLC (silica gel, DCM/n-hexane=1:2): Rf=0.54

DSC: melting point 97° C. (onset), unsublimated material

1H-NMR (CD2Cl2 referenced to 5.31 ppm, 500.13 MHz): δ [ppm]=1.31 (s, 9H, CH3), 5.82 (br. s, 1H, NH), 7.08 (br. m, 4H, phenylene), 7.28 ("t", J=7.5 Hz, 1H, p-Ph), 7.32 ("d", J=8.5 Hz, 2H, phenylene), 7.40 ("t", J=7.5 Hz, 2H, m-Ph), 7.50 ("d", J=8.5 Hz, 2H, phenylene), 7.57 ("d", J=7.5 Hz, 2H, o-Ph).

13C-NMR (CD2Cl2 referenced to 53.73 ppm, 125.76 MHz): δ [ppm]=31.52 (q, Me), 34.39 (s, CMe3), 117.16 (d, phenylene), 118.61 (d, phenylene), 126.46 (d), 126.60 (d), 126.78 (d, p-Ph), 128.10 (d), 129.03 (d), 133.11 (s), 140.33 (s), 141.11 (s), 143.65 (s, CAr—N), 144.79 (s, CAr—N).

1.2.13 Characterisation of N-(p-tolyl)-[1,1'-biphenyl]-2-amine (precursor to (38))

TLC (silica gel, DCM/n-hexane=1:5): Rf=0.34

1H-NMR (CD2Cl2 referenced to 5.31 ppm, 500.13 MHz); δ [ppm]=2.27 (s, 3H, Me), 5.58 (br. s, 1H, NH), 6.93 ("d" with fine splitting, J=8.5 Hz, 2H, phenylene), 6.94 ("dd", J=7.5 Hz, 1.5 Hz, 1H), 7.06 ("d", J=8.5 Hz, 2H, phenylene), 7.20 ("t" with fine splitting, J=8.0 Hz, 1H, p-Ph), 7.21 ("d", J=7.5 Hz, 1H), 7.25 ("dd", J=9.0 Hz, 1.0 Hz, 1H), 7.33-7.38 (m, 1H), 7.42-7.44 (m, 4H).

13C-NMR (CD2Cl2 referenced to 53.73 ppm, 125.76 MHz): δ [ppm]=20.69 (q, Me), 116.82 (d, 1C), 119.45 (d, 2C), 120.69 (d, 1C), 127.69 (d, 1C), 128.51 (d, 1C), 129.20 (d, 2C), 129.60 (d, 2C), 130.09 (d, 2C), 131.09 (d, 1C), 131.27 (s), 131.34 (s), 139.53 (s), 140.96 (s, CAr—N), 141.35 (s, CAr—N). The carbon number specified with the individual signals was based on the respective signal intensities.

1.2.14 Characterisation of N-(2,4-dimethylphenyl)-[1,1'-biphenyl]-4-amine (precursor to (17))

TLC (silica gel, DCM/n-hexane=1:5): Rf=0.25

DSC: melting point: 59° C. (onset), unsublimated material

1H-NMR (CD2Cl2 referenced to 5.31 ppm, 500.13 MHz): δ [ppm]=2.22 (s, 3H, Me), 2.29 (s, 3H, Me), 5.46 (s, 1H, NH), 6.90 ("d" with fine splitting, J=8.5 Hz, 2H, phenylene), 6.98 ("dd", J=8.0 Hz, 1.5 Hz, 1H, broadened signal, xylene ring), 7.06 (s, 1H, broadened signal, xylene ring, CH(CMe)2), 7.15 ("d", J=8.0 Hz, 1H, xylene ring), 7.26 ("t" with fine splitting, J=7.5 Hz, 1H, p-Ph), 7.39 ("t" with fine splitting, J=7.5 Hz, 2H, m-Ph), 7.46 ("d" with fine splitting, J=9.0 Hz, 2H, phenylene), 7.55 ("dd", J=8.0 Hz, 1.5 Hz, 2H, o-Ph).

13C-NMR (CD2Cl2 referenced to 53.73 ppm, 125.76 MHz): δ [ppm]=17.94 (q, Me), 20.80 (q, Me), 116.38 (d, phenylene or o-Ph or m-Ph), 121.46 (d, xylene or p-Ph), 126.54 (d, phenylene or o-Ph or m-Ph), 126.64 (d, xylene or p-Ph), 127.56 (d, xylene or p-Ph), 128.05 (d, phenylene or o-Ph or m-Ph), 129.00 (d, phenylene or o-Ph or m-Ph), 130.57 (s), 131.96 (d, xylene or p-Ph), 132.32 (s), 132.98 (s), 138.24 (s), 141.22 (s, CAr—N), 144.98 (s, CAr—N).

1.2.15 Characterisation of N-(2,4-dimethylphenyl)naphthalen-2-amine (precursor to (16))

TLC (silica gel, DCM/n-hexane=1:1): Rf=0.56

DSC: no DSC measurement, since substance was obtained as oil

1H-NMR (CD2Cl2 referenced to 5.31 ppm, 500.13 MHz): δ [ppm]=2.25 (s, 3H, Me), 2.33 (s, 3H, Me), 5.56 (s, br., 1H, NH), 7.02 ("dd", J=8.0 Hz, 1.5 Hz, broadened signal, 1H), 7.06 ("d", J=2.5 Hz, 1H, naphthyl H-1), 7.10 (br. s, 1H, m-H xylyl), 7.13 ("dd", J=8.5 Hz, 2.5 Hz, 1H), 7.21 ("d", J=8.0 Hz, 1H), 7.25 ("ddd", J=8.0 Hz, 7.0 Hz, 1.0 Hz, 1H, naphthyl H-6 or H-7), 7.36 ("ddd", J=8.0 Hz, 7.0 Hz, 1.5 Hz, 1H, naphthyl H-6 or H-7), 7.57 ("d", J=8.5 Hz, 1H), 7.712 ("d", J=9.0 Hz, 1H), 7.715 ("d", J=7.5 Hz, 1H).

13C-NMR (CD2Cl2 referenced to 53.73 ppm, 125.76 MHz): δ [ppm]=17.94 (q, o-Me), 20.82 (q, p-Me), 109.21 (d), 119.38 (d), 121.89 (d), 123.03 (d), 126.39 (d), 126.60 (d), 127.60 (d), 127.83 (d), 128.78 (s), 129.23 (d), 130.92 (s), 132.00 (d), 133.27 (s), 135.18 (s), 138.25 (s, CAr—N), 143.34 (s, CAr—N).

1.2.16 Characterisation of N-(4-isopropylphenyl)naphthalen-2-amine (precursor to (10))

TLC (silica gel, DCM/n-hexane=1:1): Rf=0.46

DSC: melting point: 69° C. (onset), unsublimated material

1H-NMR (CD2Cl2 referenced to 5.31 ppm, 500.13 MHz): δ [ppm]=1.25 (d, 3J=7.0 Hz, 6H, Me), 2.89 ("quint", J=7.0 Hz, 1H, CHMe2), 5.90 (s, 1H, NH), 7.13 ("d" with fine splitting, J=8.5 Hz, 2H, phenylene), 7.18 ("d", J=9.0 Hz, 1H, naphthyl), 7.19 ("d" with fine splitting, J=8.0 Hz, 2H, phenylene), 7.26 ("ddd", J=8.0 Hz, 7.0 Hz, 1.0 Hz, 1H, naphthyl H-6 or H-7), 7.38 ("ddd", J=8.0 Hz, 7.0 Hz, 1.0 Hz, 1H, naphthyl H-6 or H-7), 7.38 (coupling pattern unclear due to signal overlap, 1H, naphthyl H-1), 7.62 ("d", J=8.5 Hz, 1H, naphthyl), 7.72 (2×d overlapped, J=9.0 Hz, 2H, naphthyl).

13C-NMR (CD2Cl2 referenced to 53.73 ppm, 125.76 MHz): δ [ppm]=24.23 (q, Me), 33.80 (d, CMe2), 110.10 (d, naphthyl), 119.35 (d, phenylene), 119.84 (d, naphthyl), 123.39 (d, naphthyl), 126.57 (d, naphthyl), 126.68 (d, naphthyl), 127.56 (d, phenylene), 127.85 (d, naphthyl), 129.14 (s), 129.33 (d, naphthyl), 135.09 (s), 140.64 (s), 142.05 (s, CAr—N), 142.85 (CAr—N).

1.2.17 Characterisation of N-(m-tolyl)naphthalen-2-amine (precursor to (21))

TLC (silica gel, DCM/n-hexane=1:1): Rf=0.59

DSC: melting point: 67° C. (onset), unsublimated material

1H-NMR (CD2Cl2 referenced to 5.31 ppm, 500.13 MHz): δ [ppm]=2.33 (s, 3H, Me), 5.93 (br. s, 1H, NH), 6.81 ("d", J=7.5 Hz, 1H), 6.99 ("d" with fine splitting, J=6.5 Hz, 1H), 7.00 (s, 1H, o-H tolyl), 7.19 (symm. m, 1H), 7.22 ("dd", J=8.5 Hz, 2.5 Hz, 1H), 7.29 ("ddd", J=8.0 Hz, 7.0 Hz, 1.0 Hz, 1H, naphthyl H-6 or H-7), 7.40 ("ddd", J=8.0 Hz, 7.0 Hz, 1.0 Hz, 1H, naphthyl H-6 or H-7), 7.43 ("d", J=2.0 Hz, 1H, naphthyl H-1), 7.65 ("d", J=8.0 Hz, 1H), 7.738 ("d", J=7.5 Hz, 1H), 7.742 ("d", J=9.0 Hz, 1H).

13C-NMR (CD2Cl2 referenced to 53.73 ppm, 125.76 MHz): δ [ppm]=21.55 (q, Me), 111.19 (d), 115.64 (d), 119.23 (d), 120.23 (d), 122.56 (d), 123.60 (d), 126.65 (d), 126.67 (d), 127.83 (d), 129.33 (d), 129.46 (d), 134.98 (s), 139.68 (s), 141.46 (s, CAr—N), 143.07 (s, CAr—N). One of the quart. carbon signals is overlapped by other signals of the secondary amine.

1.2.18 Characterisation of N-mesityl-[1,1'-biphenyl]-4-amine (precursor to (20))

TLC (silica gel, DCM/n-hexane=1:1): Rf=0.55

DSC: melting point: 76° C. (onset), unsublimated material

1H-NMR (CD2Cl2 referenced to 5.31 ppm, 500.13 MHz): δ [ppm]=2.18 (s, 6H, ortho-Me), 2.30 (s, 3H, para-Me), 5.28 (br. S, 1H, NH), 6.53 ("d" with fine splitting, J=8.5 Hz, 2H, phenylene), 6.96 (s, 2H, mesityl-CH), 7.23 ("t" with fine splitting, J=7.5 Hz, 1H, p-Ph), 7.37 ("t", J=8.0

Hz, 2H, m-Ph), 7.40 ("d" with fine splitting, J=8.5 Hz, 2H, phenylene), 7.52 ("dd", J=8.0 Hz, 1.5 Hz, 2H, o-Ph).

13C-NMR (CD2Cl2 referenced to 53.73 ppm, 125.76 MHz): δ [ppm]=18.26 (q, ortho-Me), 20.93 (q, para-Me), 113.67 (d), 126.34 (d, p-Ph), 126.40 (d), 128.07 (d), 128.93 (d), 129.45 (d), 130.77 (s), 135.61 (s), 135.94 (s), 136.28 (s), 141.41 (s, CAr—N), 146.67 (s, CAr—N).

1.2.19 Characterisation of N-(3,5-bis(trifluoromethyl)phenyl)naphthalen-2-amine (precursor to (28))

TLC (silica gel, DCM/n-hexane=1:1): Rf=0.65
DSC: melting point: 91° C. (onset), unsublimated material 1H-NMR (CD2Cl2 referenced to 5.31 ppm, 500.13 MHz): δ [ppm]=6.30 (br. s, 1H, NH), 7.30 ("dd", J=9.0 Hz, 2.0 Hz, 1H, naphthyl), 7.37 (br. s, 1H, arom. CH between CF3 groups), 7.41 ("ddd", J=8.0 Hz, 7.0 Hz, 1.0 Hz, 1H, naphthyl H-6 or H-7), 7.48 ("ddd", J=8.0 Hz, 7.0 Hz, 1.0 Hz, 1H, naphthyl H-6 or H-7) and overlapped 7.48 (br. s, 2H, o-H subst. phenyl), 7.56 ("d", J=2.5 Hz, 1H, naphthyl H-1), 7.74 ("d", J=8.0 Hz, 1H, naphthyl), 7.82 ("d", J=8.0 Hz, 1H, naphthyl), 7.86 ("d", J=8.5 Hz, 1H, naphthyl).

13C-NMR (CD2Cl2 referenced to 53.73 ppm, 125.76 MHz): δ [ppm]=113.36 (d, "quint" splitting, 3JCF=3.9 Hz, arom. CH between CF3 groups), 115.86 (d, br. q-splitting, 3JCF=3.0 Hz, o-C subst. phenyl), 116.14 (d, naphthyl), 121.27 (d, naphthyl), 123.79 (s, q-splitting, 1JCF=272.6 Hz, CF3), 125.15 (d, naphthyl), 127.09 (d, naphthyl), 127.20 (d, naphthyl), 127.99 (d, naphthyl), 130.03 (d, naphthyl), 130.74 (s), 132.81 (s, q-splitting, 2JCF=32.9 Hz, CAr—CF3), 134.63 (s), 138.44 (s, CAr—N), 145.76 (s, CAr—N).

1.2.21 Characterisation of N-(m-tolyl)naphthalen-1-amine (precursor to (22))

TLC (silica gel, DCM/n-hexane=1:1): Rf=0.61
1H-NMR (CD2Cl2 referenced to 5.31 ppm, 500.13 MHz): δ [ppm]=2.31 (s, 3H, Me), 5.99 (br. s, 1H, NH), 6.77 ("d", J=7.5 Hz, 1H), 6.82 ("dd", J=8.0 Hz, 2.5 Hz, 1H), 6.86 S, 1H, o-H tolyl), 7.16 ("t", J=7.5 Hz, 1H, m-tolyl or H-3 naphthyl), 7.38 ("dd", J=7.5 Hz, 1.5 Hz, 1H), 7.42 ("t", J=7.5 Hz, 1H, m-tolyl or H-3 naphthyl), 7.50 ("ddd", J=8.0 Hz, 6.5 Hz, 1.5 Hz, 1H, naphthyl H-6 or H-7), 7.53 ("ddd", J=7.5 Hz, 6.5 Hz, 1.5 Hz, 1H, naphthyl H-6 or H-7), 7.58 ("d", J=8.0 Hz, 1H), 7.89 ("d" with fine splitting, J=8.0 Hz, 1H), 8.03 ("d" with fine splitting, J=8.0 Hz, 1H).

13C-NMR (CD2Cl2 referenced to 53.73 ppm, 125.76 MHz): δ [ppm]=21.54 (q, Me), 114.86 (d), 115.79 (d), 118.40 (d), 121.69 (d), 121.99 (d), 122.87 (d), 125.87 (d), 126.35 (d), 126.37 (d), 127.91 (s), 128.75 (d), 129.39 (d), 135.04 (s), 139.31 (s), 139.56 (s), 144.99 (s, CAr—N).

1.2.22 Characterisation of N-(3,5-dimethylphenyl)naphthalen-2-amine (precursor to (48))

TLC (silica gel, DCM/n-hexane=2:1): Rf=0.61
DSC: melting point: 98° C. (onset), unsublimated material 1H-NMR (CD2Cl2 referenced to 5.31 ppm, 500.13 MHz): δ [ppm]=2.29 (s, 6H, Me), 5.88 (br. s, 1H, NH), 6.65 (s, 1H, p xylyl), 6.81 (s, 2H, o-xylyl), 7.21 ("dd", J=8.5 Hz, 2.0 Hz, 1H), 7.39 ("ddd", J=8.0 Hz, 7.0 Hz, 1.0 Hz, 1H, naphthyl H 6 or H 7), 7.39 ("ddd", J=8.0 Hz, 7.0 Hz, 1.0 Hz, 1H, naphthyl H 6 or H 7), 7.41 ("d", J=2.0 Hz, 1H, naphthyl H 1), 7.65 ("d", J=8.5 Hz, 1H), 7.73 ("d", J=9.0 Hz, 2H).

13C-NMR (CD2Cl2 referenced to 53.73 ppm, 125.76 MHz): δ [ppm]=21.45 (q, Me), 111.18 (d), 116.42 (d, o-xylyl), 120.28 (d), 123.54 (d), 123.59 (d), 126.64 (2×d, signal overlap due to intensity), 127.83 (d), 129.29 (d), 135.01 (s), 139.42 (2×s, signal overlap due to intensity), 141.62 (s), 143.00 (s, CAr—N).

1.2.23 Characterisation of von N-(3,5-dimethylphenyl)[1,1'-biphenyl]-4-amine (precursor to (49))

TLC (silica gel, DCM/n-hexane=2:1): Rf=0.54
DSC: melting point: 110° C. (onset), unsublimated material
GC-MS: m/z=273/274/275

2. Coupling of the Secondary Amines to the Terphenyl Core, General Instructions

Scheme 2. General reaction scheme for coupling of the secondary amines to the terphenyl core

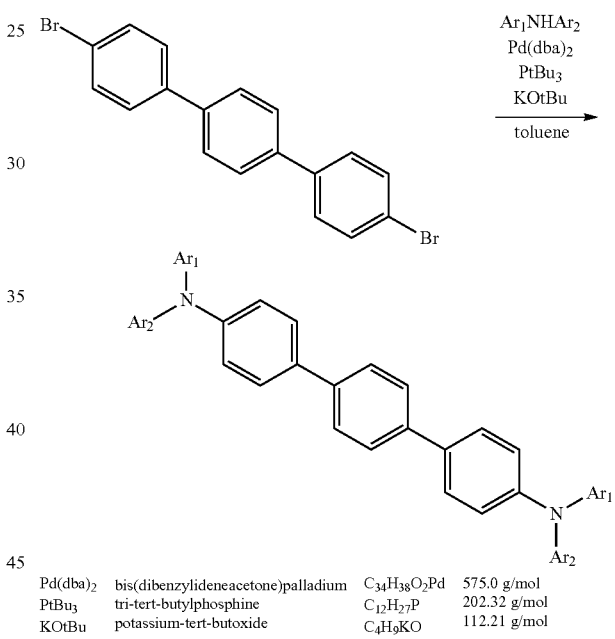

| Pd(dba)2 | bis(dibenzylideneacetone)palladium | C34H38O2Pd | 575.0 g/mol |
| PtBu3 | tri-tert-butylphosphine | C12H27P | 202.32 g/mol |
| KOtBu | potassium-tert-butoxide | C4H9KO | 112.21 g/mol |

2.1 General Synthesis Instructions

All procedures were performed in thoroughly heated glassware in an inert argon atmosphere. Commercially obtainable compounds were used in the acquired purities without additional preliminary purification steps, apart from the solvents, which were used in degassed and dried form.

Secondary amine (2.0-2.2 eq), 4,4"-dibromo-p-terphenyl (1.0 eq), tri-tert-butylphosphine (2.0-3.0 mol. %), tris(dibenzylideneacetone)dipalladium(0) (2.0 mol. %) and potassium tert-butanolate (3.0 eq) are weighed out under argon atmosphere. The mixture is dissolved in toluene (degassed, SPS quality) and stirred at 80-85° C. or under reflux (120° C.) until practically complete conversion of the starting amine (TLC control).

After cooling, excess base is separated either by washing with water or via filtration (in part over a layer of silica gel), the product is precipitated by addition of n-hexane and is purified by means of washing with methanol or via column chromatography on silica gel (DCM/n-hexane mixtures). Additional purification is achieved by means of gradient sublimation.

2.1.1 Synthesis of N4,N4''-di(naphthalen-2-yl)-N4, N4''-diphenyl-[1,1':4',1''-terphenyl]-4,4''-diamine (3)

The synthesis was performed in accordance with the general synthesis instructions. N-phenyl-2-naphthylamine (1.24 g, 2.2 eq, 5.7 mmol), 4,4''-dibromo-p-terphenyl (1.00 g, 1 eq, 2.6 mmol), tri-tert-butylphosphine (16 mg, 3 mol. %, 0.077 mmol), bis(dibenzylideneacetone)palladium (30 mg, 2 mol. %, 0.052 mmol) and potassium tert-butanolate (869 mg, 3 eq, 7.7 mmol) were stirred in toluene (25 mL, SPS quality) overnight (18 h) at 80° C. Filtration and thorough washing with n-hexane and methanol until the filtrate runs clear provided 1.5 g (88% yield, HPLC purity 99.7%) of diamine.

Further purification was achieved by means of gradient sublimation (sublimation yields 50-87%).

2.1.2 Synthesis of N4,N4''-di([1,1'-biphenyl]-4-yl)-N4,N4''-di-p-tolyl-[1,1':4',1''-terphenyl]-4,4''-diamine (6)

The synthesis was performed in accordance with the general synthesis instructions. N-(p-tolyl)-[1,1'-biphenyl]-4-amine (1.47 g, 0.2.2 eq, 5.7 mmol), 4,4''-dibromo-p-terphenyl (1.00 g, 1 eq, 2.6 mmol), tri-tert-butylphosphine (16 mg, 3.0 mol. %, 0.077 mmol), bis(dibenzylideneacetone)palladium (30 mg, 2.0 mol. %, 0.052 mmol) and potassium tert-butanolate (869 mg, 3 eq, 7.7 mmol) were stirred in toluene (25 mL, SPS quality) overnight (18 h) at 80° C. Filtration and subsequent product precipitation by means of n-hexane provided 1.63 g (85% yield, HPLC purity 97%) of diamine.

Further purification was achieved by means of gradient sublimation (sublimation yields von 67-74%).

2.1.3 Synthesis of N4,N4''-di(naphthalen-2-yl)-N4, N4''-di-p-tolyl-[1,1':4',1''-terphenyl]-1-4,4''-diamine (4)

The synthesis was performed in accordance with the general synthesis instructions. N-(p-tolyl)naphthalen-2-amine (3.97 g, 17.0 mmol, 2.2 eq), 4,4''-dibromo-p-terphenyl (3.00 g, 7.7 mmol, 1.0 eq), tri-tert-butylphosphine (31 mg, 0.16 mmol, 2.0 mol. %), tris(dibenzylideneacetone) dipalladium(0) (142 mg, 0.16 mmol, 2.0 mol. %) and sodium tert-butanolate (2.23 g, 23.2 mmol, 3.0 eq) were stirred in toluene (75 mL, degassed, SPS quality) overnight at 85° C. Filtration, product precipitation with n-hexane and purification by column chromatography on silica gel (DCM/n-hexane=1:1) provided 4.13 g (77% yield, HPLC purity 98.3%) of diamine.

Further purification was achieved via gradient sublimation (sublimation yield 87%, HPLC purity 99.8%).

2.1.4 Synthesis of N4,N4''-di([1,1'-biphenyl]-4-yl)-N4,N4''-bis(4-methoxyphenyl)-[1,1':4',1''-terphenyl]-4,4''-diamine (7)

The synthesis was performed in accordance with the general synthesis instructions. N-(4-methoxyphenyl)-[1,1'-biphenyl]-4-amine (4.68 g, 2.2 eq, 17.0 mmol), 4,4''-dibromo-p-terphenyl (3.00 g, 1 eq, 7.7 mmol), tri-tert-butylphosphine (47 mg, 3.0 mol. %, 0.23 mmol), bis(dibenzylideneacetone)palladium (89 mg, 2.0 mol. %, 0.16 mmol) and potassium tert-butanolate (2.60 g, 3 eq, 23.2 mmol) were stirred in toluene (75 mL, SPS quality) overnight (18 h) at 80° C. Product precipitation with n-hexane, washing with water and treatment with MTBE/n-hexane in an ultrasonic bath provided 4.52 g (75% yield, HPLC purity 99.7%) of diamine.

Attempts at further purification by means of gradient sublimation were unsuccessful and led to partial decomposition of the compound.

2.1.5 Synthesis of N4,N4''-di(naphthalen-1-yl)-N4, N4''-di-p-tolyl-[1,1':4',1''-terphenyl]-4,4''-diamine (1)

The synthesis was performed in accordance with the general synthesis instructions. N-(p-tolyl)naphthalen-1-amine (3.97 g, 2.2 eq, 17.0 mmol), 4,4''-dibromo-p-terphenyl (3.00 g, 1.0 eq, 7.7 mmol), tri-tert-butylphosphine (47 mg; 3.0 mol. %, 0.23 mmol), bis(dibenzylideneacetone) palladium (89 mg, 2.0 mol. %, 0.16 mmol) ad potassium tert-butanolate (2.60 g, 3.0 eq, 23.2 mmol) were stirred in toluene (75 mL, SPS quality) overnight (18 h) at 80° C. Filtration over Celite®, concentration of the filtrate and precipitation from DCM/n-hexane provided 5.24 g (yield 98%, HPLC purity 97.8%) of diamine. The HPLC purity could be increased to 99.2% by means of column chromatography on silica gel (n-hexane/DCM=1:1).

Further purification was achieved by means of gradient sublimation (sublimation yield 77%).

2.1.6 Synthesis of N4,N4''-bis(4-methoxyphenyl)-N4,N4''-di(naphthalen-1-yl)[1,1':4',1''-terphenyl]-4,4''-diamine (2)

The synthesis was performed in accordance with the general synthesis instructions. N-(4-methoxyphenyl)naphthalen-1-amine (4.24 g, 17.0 mmol, 2.2 eq), 4,4''-dibromo-p-terphenyl (3.00 g, 7.7 mmol, 1 eq), tri-tert-butylphosphine (47 mg, 0.23 mmol, 3.0 mol. %), bis(dibenzylideneacetone) palladium (89 mg, 0.16 mmol, 2.0 mol. %) and potassium-tert-butanolate (2.60 g, 23.2 mmol, 3.0 eq) were stirred in toluene (75 mL, SPS quality) overnight (18 h) at 80° C. Product precipitation by means of n-hexane, separation by means of filtration and purification by column chromatography on silica gel (DCM/n-hexane=1:1) provided 4.4 g of product (HPLC purity 98.5%). Since the raw products from a number of batches were combined and purified by chromatography, the yield can only be back-calculated. Here, a value of 59% is given.

Attempts at further purification by means of gradient sublimation were unsuccessful and led to partial decomposition of the compound.

2.1.7 Synthesis of N4,N4''-bis(4-methoxyphenyl)-N4,N4''-di(naphthalen-2-yl)[1,1':4',1''-terphenyl]-4,4''-diamine (5)

The synthesis was performed in accordance with the general synthesis instructions. N-(p-tolyl)naphthalen-2-amine (4.24 g, 17.0 mmol, 2.2 eq), 4,4''-dibromo-p-terphenyl (3.00 g, 7.7 mmol, 1 eq), tri-tert-butylphosphine (47 mg, 0.23 mmol, 3.0 mol. %), bis(dibenzylideneacetone)palladium (89 mg, 0.16 mmol, 2.0 mol. %) and potassium tert-butanolate (2.60 g, 23.2 mmol, 3.0 eq) were stirred in toluene (75 mL, SPS quality) overnight (18 h) at 80° C. Product precipitation by means of n-hexane, separation by means of filtration and purification by column chromatography on silica gel (DCM/n-hexane=1:1) provided 5.3 g of product (HPLC purity 98.6%). Since the raw products from a number of batches were combined and purified by chromatography, the yield can only be back-calculated. Here, a value of 71% is given.

Attempts at further purification by means of gradient sublimation were unsuccessful and led to partial decomposition of the compound.

2.1.8 Synthesis of N4,N4"-di([1,1'-biphenyl]-4-yl)-N4,N4"-bis(4-phenoxyphenyl)-[1,1':4',1"-terphenyl]-4,4"-diamine (13)

The synthesis was performed in accordance with the general synthesis instructions. N-(4-phenoxyphenyl)-[1,1'-biphenyl]-4-amine (4.00 g, 2.2 eq, 11.9 mmol), 4,4"-dibromo-p-terphenyl (2.09 g, 1.0 eq, 5.3 mmol), tri-tert-butylphosphine (33 mg, 3.0 mol. %, 0.16 mmol), bis(dibenzylideneacetone)palladium (62 mg, 2.0 mol. %, 0.11 mmol) and potassium tert-butanolate (1.82 g, 3.1 eq, 16.2 mmol) were stirred in toluene (50 mL, SPS quality) overnight (20 h) at 80° C. Gel filtration over silica gel (DCM), concentration under vacuum and washing with methanol provided 4.77% (98% yield, HPLC purity 99.6%) of diamine.

Further purification was achieved by means of gradient sublimation (sublimation yield 87%, HPLC purity after sublimation >99.9%).

2.1.9 Synthesis of N4,N4"-di([1,1'-biphenyl]-4-yl)-N4,N4"-di(naphthalen-1-yl)[1,1':4',1"-terphenyl]-4,4"-diamine (8)

The synthesis was performed in accordance with the general synthesis instructions. N-([1,1'-biphenyl]-4-yl)naphthalen-1-amine (5.02 g, 17.0 mmol, 2.2 eq), 4,4"-dibromo-p-terphenyl (3.00 g, 7.7 mmol, 1 eq), tri-tert-butylphosphine (47 mg, 0.23 mmol, 3.0 mol. %), bis(dibenzylideneacetone)palladium (89 mg, 0.16 mmol, 2.0 mol. %) and potassium tert-butanolate (2.60 g, 23.2 mmol, 3.0 eq) were stirred in toluene (75 mL, SPS quality) overnight (18 h) at 80° C. Product precipitation with n-hexane and thorough washing with methanol delivered 6.02 g of product (95% yield, HPLC purity >98.2%).

Further purification was achieved by means of gradient sublimation (sublimation yield 46-73%). Here, the product contained approximately 1% of the 2-naphthyl constitutional isomer.

2.1.10 Synthesis of N4,N4"-di([1,1'-biphenyl]-4-yl)-N4,N4"-di(naphthalen-2-yl)[1,1':4',1"-terphenyl]-4,4"-diamine (9)

The synthesis was performed in accordance with the general synthesis instructions. N-([1,1'-biphenyl]-4-yl)naphthalen-2-amine (5.02 g, 17.0 mmol, 2.2 eq), 4,4"-dibromo-p-terphenyl (3.00 g, 7.7 mmol, 1 eq), tri-tert-butylphosphine (47 mg, 0.23 mmol, 3.0 mol. %), bis(dibenzylideneacetone)palladium (89 mg, 0.16 mmol, 2.0 mol. %) and potassium tert-butanolate (2.60 g, 23.2 mmol, 3.0 eq) were stirred in toluene (75 mL, SPS quality) overnight (18 h) at 80° C. Precipitation with n-hexane, thorough washing with methanol and n-hexane and subsequent purification by column chromatography of the remaining residue on silica gel (DCM/n-hexane=1:1) provided 3.86 g of diamine (61% yield, HPLC purity >97.3%).

Further purification was achieved by means of gradient sublimation (sublimation yields 63-80%).

2.1.11 Synthesis of N4,N4"-bis(4-(tert-butyl)phenyl)-N4,N4"-di(naphthalen-2-yl)[1,1':4',1"-terphenyl]-4,4"-diamine (11)

The synthesis was performed in accordance with the general synthesis instructions. N-(4-(tert-butyl)phenyl)naphthalen-2-amine (1.50 g, 2.1 eq, 5.4 mmol), 4,4"-dibromo-p-terphenyl (1.00 g, 1.0 eq, 2.6 mmol), tri-tert-butylphosphine (85 mg, 16.0 mol. %, 0.42 mmol), bis(dibenzylideneacetone)palladium (30 mg, 2.0 mol. %, 0.05 mmol) and potassium tert-butanolate (875 mg, 3.0 eq, 7.8 mmol) were stirred in toluene (60 mL, SPS quality) overnight (23 h) at 85° C. Addition of chloroform, washing with water and gel filtration over silica gel (chloroform), followed by ultrasound treatment of the residue obtained from the filtrate in vacuo delivered 2.72 g (135% yield, HPLC purity 98.0%).

Further purification was achieved by means of gradient sublimation (sublimation yield 76%, HPLC purity: 99.0%).

2.1.12 Synthesis of N4,N4"-di(naphthalen-2-yl)-N4,N4"-bis(4-phenoxyphenyl)[1,1':4',1"-terphenyl]-4,4"-diamine (12)

The synthesis was performed in accordance with the general synthesis instructions. N-(4-phenoxyphenyl)naphthalen-2-amine (2.50 g, 2.2 eq, 8.0 mmol), 4,4"-dibromo-p-terphenyl (1.42 g, 1.0 eq, 3.7 mmol), tri-tert-butylphosphine (22 mg, 3.0 mol. %, 0.11 mmol), bis(dibenzylideneacetone)palladium (42 mg, 2.0 mol. %, 0.07 mmol) and potassium tert-butanolate (1.23 g, 3.0 eq, 11.0 mmol) were stirred in toluene (30 mL, SPS quality) overnight at 80° C. Filtration over Celite® followed by a recrystallisation (DCM/n-hexane) of the residue obtained from the filtrate under vacuum delivered 2.9 g of raw product (96% yield). Purification by column chromatography on silica gel (gradient chloroform/n-hexane=1:4→1:1) ultimately gave 2.34 g of diamine (yield 75%, HPLC purity 98.6%).

Further purification was achieved by means of gradient sublimation (sublimation yield 82%).

2.1.13 Synthesis of N4,N4"-di([1,1'-biphenyl]-4-yl)-N4,N4"-bis(4-(tert-butyl)phenyl)-[1,1':4',1"-terphenyl]-4,4"-diamine (25)

The synthesis was performed in accordance with the general synthesis instructions. N-(4-(tert-butyl)phenyl)-[1,1'-biphenyl]-4-amine (2.00 g, 2.2 eq, 6.6 mmol), 4,4"-dibromo-p-terphenyl (1.17 g, 1.0 eq, 3.0 mmol), tri-tert-butylphosphine (18 mg, 3.0 mol. %, 0.09 mmol), bis(dibenzylideneacetone)palladium (35 mg, 2.0 mol. %, 0.06 mmol) and potassium tert-butanolate (1.02 g, 3.0 eq, 9.1 mmol) were stirred in toluene (25 mL, SPS quality) overnight at 80° C. Product precipitation with n-hexane, separation via filtration and thorough washing with methanol and with n-hexane and drying provided 2.7 g of raw product (108% yield). Recrystallisation from DCM/n-hexane gave 2.4 g of diamine (yield 97%, HPLC purity 100%).

Further purification was achieved by means of gradient sublimation (sublimation yield 84%, HPLC purity after sublimation >99.9%).

2.1.14 Synthesis of N4,N4"-di([1,1'-biphenyl]-2-yl)-N4,N4"-di-p-tolyl-[1,1':4',1"-terphenyl]-4,4"-diamine (38)

The synthesis was performed in accordance with the general synthesis instructions. N-(p-tolyl)[1,1'-biphenyl]-2-amine (2.49 g, 2.2 eq, 9.6 mmol), 4,4"-dibromo-p-terphenyl (1.69 g, 1.0 eq, 4.4 mmol), tri-tert-butylphosphine (27 mg, 3.0 mol. %, 0.13 mmol), bis(dibenzylideneacetone)palladium (50 mg, 2.0 mol. %, 0.09 mmol) and potassium tert-butanolate (1.47 g, 3.0 eq, 13.1 mmol) were stirred in toluene (30 mL, SPS quality) overnight at 80° C. After concentration and product precipitation with n-hexane, separation via filtration and subsequent rapid gel filtration over silica gel (DCM), it was possible to obtain 2.84 g of product (89% yield, HPLC purity 99.6%).

Further purification was achieved by means of gradient sublimation (sublimation yield 90%).

2.1.15 Synthesis of 2',5'-dimethyl-N4,N4"-di(naphthalen-2-yl)-N4,N4"-diphenyl-[1,1':4',1"-terphenyl]-4,4"-diamine (41)

The synthesis was performed in accordance with the general synthesis instructions. The dimethyl-substituted dibromoterphenyl was produced in accordance with instructions from the literature (C. Baillie, J. Xiao, Tetrahedron 2004, 60, 4159-4168.).

N-phenylnaphthalen-2-amine (1.94 g, 2.0 eq, 8.8 mmol), 4,4"-dibromo-2',5'-dimethyl-1,1':4',1"-terphenyl (1.84 g, 1.0 eq, 4.4 mmol), tri-tert-butylphosphine (27 mg, 3.0 mol. %, 0.13 mmol), bis(dibenzylideneacetone)palladium (51 mg, 2.0 mol. %, 0.09 mmol) and potassium tert-butanolate (1.48 g, 3.0 eq, 13.2 mmol) were stirred in toluene (150 mL, SPS quality) over 43½ hours at 80° C. After gel filtration, treatment of the residue obtained from the filtrate (2.86 g) with methanol in an ultrasonic bath and drying in a vacuum drying cabinet at 40° C., there remained 131 g of raw product (43% yield, HPLC purity 55.3%). Purification by means of MPLC (DCM/n-hexane, linear gradient 15% DCM 35% DCM over 35 min), subsequent precipitation by careful evaporation of the methylene chloride and washing with methanol provided 0.55 g (18% yield, HPLC purity 96.3%) of tertiary diamine.

Further purification was achieved by means of gradient sublimation (sublimation yield 49%).

2.1.16 Synthesis of N4,N4"-di([1,1'-biphenyl]-4-yl)-N4,N4"-bis(2,4-dimethylphenyl)-[1,1':4',1"-terphenyl]-4,4"-diamine (17)

The synthesis was performed in accordance with the general synthesis instructions. N-(2,4-dimethylphenyl)[1,1'-biphenyl]-4-amine (2.96 g, 2.1 eq, 10.8 mmol), 4,4"-dibromo-p-terphenyl (2.00 g, 1.0 eq, 5.2 mmol), tri-tert-butylphosphine (32 mg, 3.0 mol. %, 0.16 mmol), bis(dibenzylideneacetone)palladium (60 mg, 2.0 mol. %, 0.10 mmol) and potassium tert-butanolate (1.75 g, 3.0 eq, 15.6 mmol) were stirred in toluene (70 mL, SPS quality) over 67 hours at 80° C. After gel filtration on silica gel (DCM/n-hexane=1:2) and treatment of the residue obtained from the filtrate under vacuum with methanol in an ultrasonic bath, there remained 4.08 g of diamine (quantitative conversion, HPLC purity 99.1%).

Further purification was achieved by means of gradient sublimation (sublimation yield 80%).

2.1.17 Synthesis of N4,N4"-bis(2,4-dimethylphenyl)-N4,N4"-di(naphthalen-2-yl)[1,1':4',1"-terphenyl]-4,4"-diamine (16)

The synthesis was performed in accordance with the general synthesis instructions. N-(2,4-dimethylphenyl)naphthalen-2-amine (3.11 g, 2.1 eq, 12.6 mmol), 4,4"-dibromo-p-terphenyl (2.32 g, 1.0 eq, 6.0 mmol), tri-tert-butylphosphine (49 mg, 4.0 mol. %, 0.24 mmol), palladium(II) acetate (27 mg, 2.0 mol. %, 0.12 mmol) and sodium tert-butylate (1.73 g, 3.0 eq, 18.0 mmol) were stirred in toluene (30 mL, SPS quality) over 3 hours at 120° C. (reflux). The reaction mixture was left to cool overnight to room temperature, suctioned off over a frit, and the residue was then washed with n-hexane, methanol and diethyl ether. Purification by column chromatography of the raw product remaining after drying (4.2 g, 97% yield, HPLC purity 97%) provided 3.44 g (80% yield, HPLC purity 97.5%) of the desired diamine.

Further purification was achieved by means of gradient sublimation (sublimation yield 86%).

2.1.18 Synthesis of N4,N4"-bis(4-isopropylphenyl)-N4,N4"-di(naphthalen-2-yl)[1,1':4',1"-terphenyl]-4,4"-diamine (10)

The synthesis was performed in accordance with the general synthesis instructions. N-(4-Isopropylphenyl)naphthalen-2-amine (1.50 g, 2.2 eq, 5.7 mmol), 4,4"-dibromo-p-terphenyl (1.01 g, 1.0 eq, 2.6 mmol), tri-tert-butylphosphine (16 mg, 3.0 mol. %, 0.08 mmol), bis(dibenzylideneacetone)palladium (30 mg, 2.0 mol. %, 0.05 mmol) and potassium tert-butanolate (879 mg, 3.0 eq, 7.8 mmol) were stirred in toluene (25 mL, SPS quality) overnight at 80° C.

The reaction mixture was cooled to room temperature, and precipitated solid was separated via filtration and then washed thoroughly with methanol and n-hexane. The remaining raw product (4 g) was taken up in DCM/toluene and washed with saturated aqueous sodium chloride solution. Insoluble solid was separated and purified with the residue from the concentration of the dried (over MgSO4) organic phase. There remained 3.5 g (179% yield, HPLC purity >72%) of raw product, which was purified via MPLC chromatography purification, (provided 2.6 g of product, 133% yield, HPLC purity 93.2%) and subsequent crystallisation from DCM/n-hexane and washing of the obtained solid with DCM. It was possible to obtain 1.28 g (66% yield, HPLC purity 89.6%, only a significant impurity of 9.2% was contained, supposedly unconverted 4,4"-dibromo-p-terphenyl) of desired diamine.

Further purification was achieved by means of gradient sublimation (sublimation yield 85%), wherein the impurity was able to be practically completely separated as "forerun" and it was possible to achieve an HPLC purity of 99.1%.

2.1.19 Synthesis of N4,N4"-di(naphthalen-2-yl)-N4,N4"-di-m-tolyl-[1,1':4',1"-terphenyl]-1-4,4"-diamine (21)

The synthesis was performed in accordance with the general synthesis instructions. N-(m-tolyl)naphthalen-2-amine (3.00 g, 2.2 eq, 12.9 mmol), 4,4"-dibromo-p-terphenyl (2.27 g, 1.0 eq, 5.8 mmol), tri-tert-butylphosphine (35 mg, 3.0 mol. %, 0.18 mmol), bis(dibenzylideneacetone)palladium (67 mg, 2.0 mol. %, 0.12 mmol) and potassium tert-butanolate (1.97 g, 3.0 eq, 17.5 mmol) were stirred in toluene (30 mL, SPS quality) overnight at 80° C. Product precipitation with n-hexane, separation via filtration and thorough washing with methanol and with n-hexane and drying provided 3.8 g of raw product (94% yield, HPLC purity 97.5%). In addition, it was possible to isolate a second fraction of 0.8 g (20% yield, HPLC purity 98.3%) from the filtrate. The two fractions were combined and purified by column chromatography on silica gel (DCM/n-hexane=1:2). After drying under vacuum (50° C.), it was possible to obtain 2.6 g (64% yield, HPLC purity 97.7%) of the desired diamine.

Further purification was achieved by means of gradient sublimation (sublimation yield 81%).

2.1.20 Synthesis of N4,N4"-di([1,1'-biphenyl]-4-yl)-N4,N4"-dimesityl-[1,1':4',1"-terphenyl]-4,4"-diamine (20)

The synthesis was performed in accordance with the general synthesis instructions. N-mesityl-[1,1'-biphenyl]-4-amine (3.00 g, 2.2 eq, 10.4 mmol), 4,4"-dibromo-p-terphenyl (1.84 g, 1.0 eq, 4.7 mmol), tri-tert-butylphosphine (29 mg, 3.0 mol. %, 0.14 mmol), bis(dibenzylideneacetone)palladium (55 mg, 2.0 mol. %, 0.10 mmol) and potassium tert-butanolate (1.59 g, 3.0 eq, 14.2 mmol) were stirred in toluene (60 mL, SPS quality) overnight at 80° C. Product precipitation with n-hexane, separation via filtration and thorough washing with n-hexane as well as drying and subsequent purification by column chromatography on silica gel (DCM/n-hexane=1:1) provided 2.7 g (yield 71%, HPLC purity 98.1%) of desired diamine.

Further purification was achieved by means of gradient sublimation (sublimation yield 77%, HPLC purity 99.2% after sublimation).

2.1.21 Synthesis of N4,N4"-bis(3,5-bis(trifluoromethyl)phenyl)-N4,N4"-di(naphthalen-2-yl)-[1,1':4',1"-terphenyl]-4,4"-diamine (28)

The synthesis was performed in accordance with the general synthesis instructions. N-(3,5-bis(trifluoromethyl)phenyl)naphthalen-2-amine (3.00 g, 2.2 eq, 12.1 mmol), 4,4"-dibromo-p-terphenyl (2.14 g, 1.0 eq, 5.5 mmol), tri-tert-butylphosphine (33 mg, 3.0 mol. %, 0.176 mmol), bis(dibenzylideneacetone)palladium (63 mg, 2.0 mol. %, 0.11 mmol) and potassium tert-butanolate (1.85 g, 3.0 eq, 16.5 mmol) were stirred in toluene (50 mL, SPS quality) overnight at 80° C. Product precipitation with n-hexane, separation via filtration and thorough washing with n-hexane as well as drying and subsequent purification by column chromatography on silica gel (DCM/n-hexane=1:2) provided 4.17 g (81% yield, HPLC purity 96.5%) of desired amine.

Further purification was achieved by means of gradient sublimation (sublimation yield 84%, HPLC purity 99.1% after sublimation).

2.1.22 Synthesis of N4,N4,N4",N4"-tetrakis(4-(tert-butyl)phenyl)-[1,1':4',1"-terphenyl]-4,4"-diamine (26)

Contrary to the general synthesis instructions, the synthesis was performed proceeding from 4,4"-diaminoterphenyl, but with use of the same catalyst system.

1-bromo-4-(tert-butyl)benzene (3.60 g, 4.4 eq, 16.9 mmol), 4,4"-diamino-p-terphenyl (1.00 g, 1.0 eq, 3.8 mmol), tri-tert-butylphosphine (154 mg, 20 mol. %, 0.76 mmol), bis(dibenzylideneacetone)palladium (219 mg, 10 mol. %, 0.38 mmol) and potassium tert-butanolate (2.56 g, 6.0 eq, 22.8 mmol) were stirred in toluene (100 mL, SPS quality) over 69½ hours at 80° C. under argon atmosphere.

After cooling, the filtrate was concentrated to dryness, filtered over a layer of silica gel (post-rinsing with DCM/n-hexane=1:3 until the filtrate runs clear). The remaining residue (3.34 g light-orange solid) was taken up in 400 mL methanol, treated over 15 minutes in an ultrasonic bath and then isolated via filtration. Post-washing with methanol (2×50 mL) and drying overnight in a vacuum drying cabinet (at 40° C.) provided 2.91 g (97% yield, HPLC purity 99.4%) of desired amine.

Further purification was achieved by means of gradient sublimation (sublimation yield 87%).

2.1.23 Synthesis of N4,N4"-di(naphthalen-1-yl)-N4,N4"-di-m-tolyl-[1,1':4',1"-terphenyl]-4,4"-diamine (22)

The synthesis was performed in accordance with the general synthesis instructions. N-(m-tolyl)naphthalen-1-amine (3.80 g, 2.2 eq, 16.3 mmol), 4,4"-dibromo-p-terphenyl (2.88 g, 1.0 eq, 7.4 mmol), tri-tert-butylphosphine (45 mg, 3.0 mol. %, 0.22 mmol), bis(dibenzylideneacetone)palladium (85 mg, 2.0 mol. %, 0.15 mmol) and potassium tert-butanolate (2.49 g, 3.0 eq, 22.2 mmol) were stirred in toluene (50 mL, SPS quality) overnight at 80° C. Product precipitation with n-hexane, separation via filtration and thorough washing with methanol and also with n-hexane and subsequent drying provided 5.7 g of raw product (111% yield). Purification by column chromatography on silica gel (DCM/n-hexane=1:2) provided 4.1 g (80% yield, HPLC purity 100%) of desired amine.

Further purification was achieved by means of gradient sublimation (sublimation yield 89%, HPLC purity 99.9%).

2.1.24 Synthesis of N4,N4"-di([1,1'-biphenyl]-4-yl)-N4,N4"-bis(4-(tert-butyl)phenyl)-2',5'-dimethyl-[1,1':4',1"-terphenyl]-4,4"-diamine (36)

The synthesis was performed in accordance with the general synthesis instructions. The dimethyl-substituted dibromoterphenyl was produced in accordance with instructions from the literature (C. Baillie, J. Xiao, Tetrahedron 2004, 60, 4159-4168.).

N-(4-(tert-butyl)phenyl)-[1,1'-biphenyl]-4-amine (2.28 g, 2.1 eq, 7.6 mmol), 4,4"-dibromo-2',5'-dimethyl-1,1':4',1"-terphenyl (1.50 g, 1.0 eq, 3.6 mmol), tri-tert-butylphosphine (22 mg, 3.0 mol. %, 0.11 mmol), bis(dibenzylideneacetone)palladium (41 mg, 2.0 mol. %, 0.07 mmol) and potassium tert-butanolate (1.21 g, 3.0 eq, 10.8 mmol) were stirred in toluene (120 mL, SPS quality) over 22½ hours at 80° C. After gel filtration (post-rinsing with DCM/n-hexane=1:2, approximately 600 mL), treatment of the residue obtained from the filtrate (3.71 g) with methanol in an ultrasonic bath and drying in a vacuum drying cabinet at 40° C., there remained 2.89 g of raw product (94% yield, HPLC purity 53.6%). Purification via column chromatography on silica gel (DCM/n-hexane=1:3) delivered two fractions of 610 mg (20% yield, HPLC purity 98.2%) and 600 mg (19% yield, HPLC purity 90.4%) of tertiary diamine.

Further purification was achieved by means of gradient sublimation (sublimation yields 77-78%).

2.1.25 Synthesis of N4,N4"-bis(3,5-dimethylphenyl)-N4,N4"-di(naphthalen-2-yl)[1,1':4',1"-terphenyl]-4,4"-diamine (48)

The synthesis was performed in slightly modified form compared with the general synthesis instructions. N-(3,5- dimethylphenyl)naphthalen-2-amine (3.82 g, 2.0 eq, 15.5 mmol), 4,4"-dibromo-p-terphenyl (3.00 g, 1.0 eq, 7.7 mmol), tri-tert-butylphosphine (47 mg, 3.0 mol. %, 0.23 mmol), palladium acetate (52 mg, 3.0 mol. %, 0.23 mmol) and sodium tert-butanolate (5.94 g, 8.0 eq, 61.8 mmol) were stirred in toluene (110 mL, SPS quality) for 2 hours at 95° C. Column chromatography (SiO2, n-hexane/DCM=1:1), and washing with hexane and methanol gave 5.21 g (93% yield, HPLC purity 99.1%) of product.

Further purification was achieved by means of gradient sublimation (sublimation yields 80-90%).

2.1.26 Synthesis of N4,N4"-di([1,1'-biphenyl]-4-yl)-N4,N4"-bis(3,5-dimethylphenyl)-[1,1':4',1"-terphenyl]-4,4"-diamine (49)

The synthesis was performed in accordance with the general synthesis instructions and modified processing. N-(3,5-dimethylphenyl)-[1,1'-biphenyl]-4-amine (3.00 g, 2.1 eq, 10.97 mmol), 4,4"-dibromo-p-terphenyl (2.03 g, 1.0 eq, 5.22 mmol), tri-tert-butylphosphine (32 mg, 3.0 mol. %, 0.16 mmol), bis(dibenzylideneacetone)palladium (60 mg, 3.0 mol. %, 0.10 mmol) and potassium tert-butanolate (1.76 g, 3.0 eq, 15.66 mmol) were stirred in toluene (60 mL, SPS quality) for 17 hours at 80° C. After cooling, the reaction solution is filtered by silica gel (DCM). 50 vol. % of hexane is added to the organic solution. A reduction of the solution leads to the precipitation of the product. 3.67 g (91% yield, HPLC purity 99.7%) of a white solid are obtained.

Further purification was achieved by means of gradient sublimation (Sublimation yield 85%).

Measurement Methods

In a standardised conductivity test at the test chamber provided, the conductivity of organic layers 50 nm thick is tested. To this end, substrates measuring 25 mm×25 mm are fixed in a substrate holder and, during vacuum deposition with organic materials, the conductivity of the layer applied by evaporation is measured. The substrate consists of a quartz glass of 1 mm and is provided with 4 ITO patterns of equal size. Four gold contacts are located on the substrate holder, via which the substrate is contacted. The substrates are tensioned in the substrate holder and are then supplied to a high-vacuum chamber (process pressure 1E-6 mbar). The organic layer is applied to the substrate during the evaporation process via the non-conductive spacing of the ITO contact patterns and is measured in-situ. This means that the measurement is begun with a layer thickness of 0 nm and a DC voltage is applied to the substrate via the described gold contacts. With growing layer up to 50 nm, the conductivity of the evaporated layer is recorded and illustrated in graph form via analysis programs.

This process can be extended by a temperature stability test. Here, a constant temperature is supplied to the substrate coated by vacuum deposition. At the same time, the conductivity of the evaporated layer is analysed. Once the conductivity has reached its maximum, a considerable nose-dive of the measured values and of the resultant measurement curve can be seen. The temperature at the maximum of the conductivity is referred to as breakdown temperature. The test is ended as soon as this maximum has been reached. The substrate coated by vacuum deposition is then removed once cooled. The test is ended as soon as the UHV chamber has been vented and the substrate coated by vapour deposition has been removed from the vacuum system.

2.2 Characterisation Data

Conductivity tests were performed with a selection of compounds according to the invention.

For this purpose, the compounds (1), (4), (6), (10), (11), (16), (17), (20), (25), (36) and (38) according to the invention were tested, whereas corresponding tests were also performed for comparative compounds (3), (8), (9), (21), (22), (26), (40) and (41), which had the following structures:

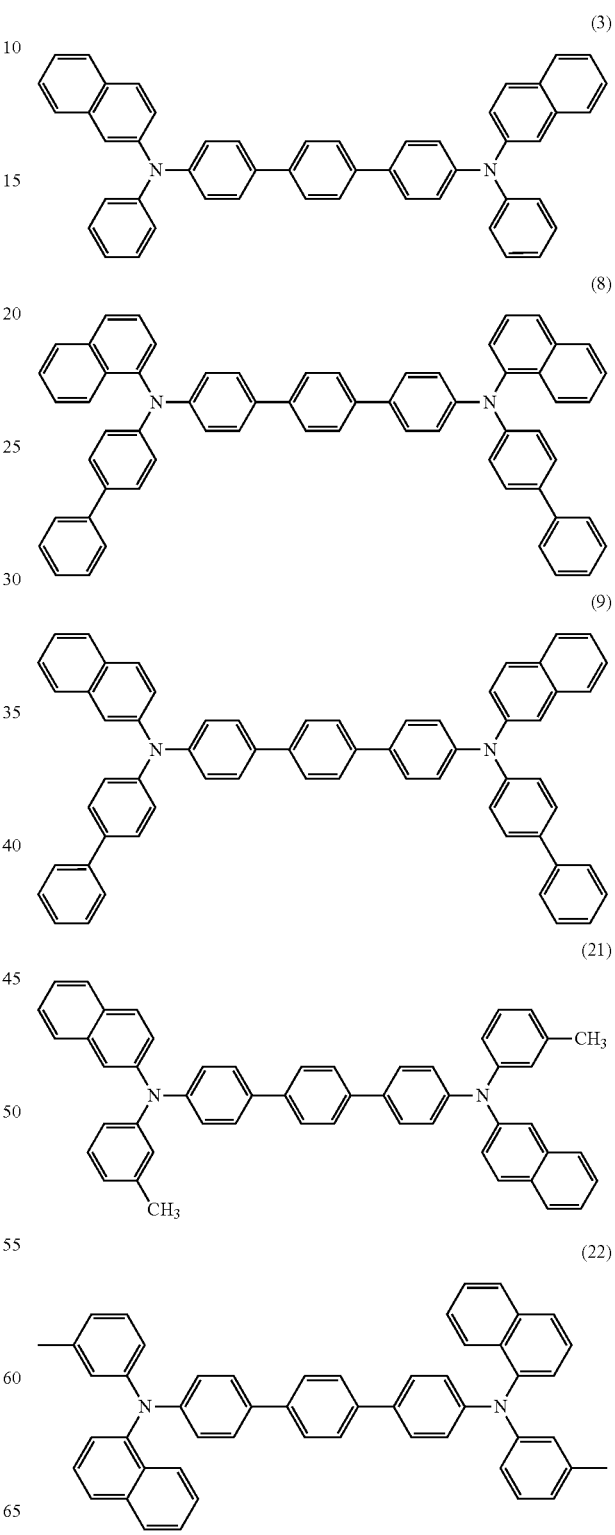

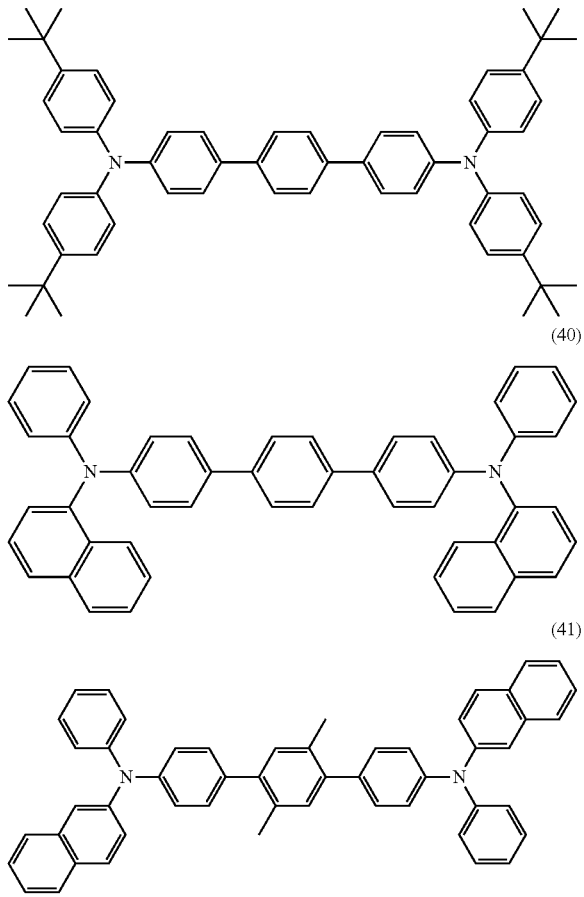

A comparison of compounds (25) and (26) shows that, although the known terphenyl diamine compound (26) substituted at the nitrogen atoms thereof with four p-tert-butyl phenyl groups has good conductivity, a combination of R2=p-tert-butyl and R1=a system with a greater conjugation then phenyl, represented here by 1,1'-biphenyl-4-yl, leads to even better conductivity than p-tert-butyl phenyl itself. The same conclusion is made with the comparison of compound (11) and compound (26), where R1=β-naphthyl produces improved conductivity. Preferred compounds thus have, at each of the two nitrogen atoms thereof, a phenyl substituted with R2, which contains a usual conjugated 6 π electron system and an aromatic substituent R1 with a conjugated π electron system that is expanded compared with phenyl, wherein the expanded conjugation occurs either by a condensation of two aromatic rings, for example as in α- or β-naphthyl, or by the direct bond thereof, as in 1,1'-biphenyl-2-yl or 1,1'-biphenyl-4-yl, for example.

Lastly, the advantages according to the invention in view of improved conductivity are also significantly evident with a comparison of the conductivities for compounds (3) (not according to the invention) and (4) (according to the invention) or (40) (not according to the invention) and (1) (according to the invention). The compounds according to the invention with R2≠H are unexpectedly better than the known analogues thereof not substituted in the phenyl ring.

A comparison between compounds (1) and (22) shows that the substitution at the para position is more favourable than at the meta position. The same can be seen in a comparison of the conductivities of compounds (4) and (21). Furthermore, in a comparison of compounds (21) and (16), which have R1=beta-naphthyl, it can be seen that R2=methyl in para- and ortho- (n=2) positions also achieves good results, which are better than with compounds with substitution in the meta position. Compounds with R2 in para- or para- and ortho position are preferred, and even double ortho-substitution is possible. A double m-substitution is surprisingly much more favourable than the single substitution, and the effect thereof is thus comparable with other double substitutions, which can be seen by the comparison of compounds (48) or (49) with (21) or (16).

In a comparison of the conductivity measurement results of compounds with R1=biphenylyl (6), (25), (38), (17), and (20), it can be seen that very good conductivities are to be achieved with all compounds that have a structure according to the above-mentioned rules. R2=alkoxy is also preferred.

A comparison of compounds (1) and (4) shows that R1=beta-naphthyl is preferred and produces better results than alpha-naphthyl. This difference between beta- and alpha-naphthyl disappears when R2 is in the meta position, as can be seen in the comparison of the data of compounds (21) and (22).

A comparison of compounds (36) and (25) or of compounds (41) and (3) shows that R3=H is preferred. At the same time, however, a comparison of compounds (36) and (3) shows that the substitution of nitrogen atoms according to the invention is advantageous insofar as the compounds according to the invention even with R3≠H are better than compounds not according to the invention with R3=H.

2.2.1 Characterisation of N4,N4'''-di(naphthalen-2-yl)-N4,N4'''-diphenyl-[1,1':4',1''-terphenyl]-4,4'''-diamine (3)

TLC (silica gel, DCM/n-hexane=1:1): Rf=0.68
CV: HOMO vs. Fc (DCM): 0.41 V (reversible), 2nd oxidation at 0.5 V (rev.)
LUMO vs. Fc (THF): −2.85 V (reversible)
DSC: melting point: 265° C. (onset), sublimated material
glass transition temperature Tg: 105° C. (onset), heating rate 10 K/min, sublimated material
1H NMR (CD2Cl2 referenced to 5.31 ppm, 500.13 MHz): δ [ppm]=7.08 ("t", J=7.5 Hz, 2H, p-H phenyl), 7.17 ("d", J=8.0 Hz, 4H, o-H phenyl), 7.18 ("d" with discernible fine splitting, J=8.5 Hz, 4H, terphenyl N-bound ring), 7.30 (m, 6H, m-H phenyl, naphthyl H), 7.35 ("ddd", J=8.0 Hz, 7.0 Hz, 1.5 Hz, 2H, naphthyl H-6 or H-7), 7.40 ("ddd", J=8.0 Hz, 7.0 Hz, 1.5 Hz, 2H, naphthyl H-6 or H-7), 7.47 ("d", J=2.5 Hz, 2H, naphthyl H-1), 7.57 ("d" with discernible fine splitting, J=8.5 Hz, 4H, terphenyl N-bound ring), 7.61 ("d", J=8.0 Hz, 2H, naphthyl H), 7.66 (s, 4H, terphenyl of middle ring), 7.75 ("d", J=8.5 Hz, 2H), 7.77 ("d", J=8.0 Hz, 2H, naphthyl H).

13C NMR (CD2Cl2 referenced to 53.73 ppm, 125.76 MHz): δ [ppm]=120.71 (d, naphthyl or p-Ph), 123.57 (d, naphthyl or p-Ph), 124.49 (d, terphenyl or m-Ph or o-Ph), 124.73 (d, naphthyl or p-Ph), 124.86 (d, naphthyl or p-Ph), 124.99 (d, terphenyl or m-Ph or o-Ph), 126.61 (d, naphthyl or p-Ph), 127.16 (d, naphthyl or p-Ph), 127.18 (d, terphenyl or m-Ph or o-Ph), 127.81 (d, naphthyl or p-Ph), 127.87 (d, terphenyl or m-Ph or o-Ph), 129.19 (d, naphthyl or p-Ph), 129.67 (d, terphenyl or m-Ph or o-Ph), 130.47 (s, naphthyl C-4a), 134.80 (s), 135.04 (s), 139.26 (s), 145.65 (s, N-bound), 147.52 (s, N-bound), 147.93 (s, N-bound).

| Elemental analysis: | ber. [%]: | C 90.33, H 5.46, N 4.21. |
| --- | --- | --- |
| | exp. [%] | C 90.17, H 5.54, N 4.23. |
| | | (after sublimation) |
| Conductivities | (10 mol. %): | 2.31E−04 S/cm (d2); 3.21E−06 S/cm (d2); 2.04E−06 S/cm (d3). |

2.2.2 Characterisation of N4,N4''-di([1,1'-biphenyl]-4-yl)-N4,N4''-di-p-tolyl-[1,1':4',1''-terphenyl]-4,4''-diamine (6)

TLC (silica gel, DCM/n-hexane=1:1): Rf=0.73
CV: HOMO vs. Fc (DCM): 0.41 V (reversible), 2nd oxidation very close to the first
LUMO vs. Fc (THF): −2.87 V (reversible)
DSC: melting point: no melting peak, even with cyclical measurement
glass transition temperature Tg: 116° C. (onset), heating rate 10 K/min, sublimated material
1H-NMR (CD2Cl2 referenced to 5.31 ppm, 500.13 MHz): δ [ppm]=2.34 (s, 6H, Me), 7.08 ("d" with discernible fine splitting, J=8.5 Hz, 4H), 7.14 (m, 12H), 7.30 ("t", J=7.5 Hz, 2H, H-4' biphenyl), 7.42 ("t", J=7.5 Hz, 4H, H-3' biphenyl), 7.50 ("d" with discernible fine splitting, J=8.5 Hz, 4H), 7.55 ("d" with discernible fine splitting, J=8.5 Hz, 4H), 7.58 ("d" with discernible fine splitting, J=8.5 Hz, 4H), 7.65 (s, 4H, terphenyl of middle ring).
13C-NMR (CD2Cl2 referenced to 53.73 ppm, 125.76 MHz): δ [ppm]=20.31 (q, Me), 123.90 (d), 123.96 (d), 125.66 (d), 126.82 (d), 127.11 (d), 127.76 (d), 127.97 (d), 129.06 (d), 130.37 (d), 133.81 (s), 134.55 (s), 135.18 (s), 139.20 (s), 140.86 (s), 145.14 (s), 147.51 (s), 147.54 (s). Proceeding from the signal integration, the signal of the p-Ph carbon of the biphenyl unit is overlapped by the signal at 127.11 ppm.

| Elemental analysis: | ber. [%]: | C 90.29, H 5.95, N 3.76. |
| --- | --- | --- |
| | exp. [%]: | C 90.36, H 5.94, N 3.78. |
| | | (after sublimation) |
| Conductivities | (10 mol. %): | 6.03E−04 S/cm (d1); 7.62E−05 S/cm (d2); 1.38E−05 S/cm (d3). |

2.2.3 Characterisation of N4,N4''-di(naphthalen-2-yl)-N4,N4''-di-p-tolyl-[1,1':4',1''-terphenyl]-4,4''-diamine (4)

TLC (silica gel, DCM/n-hexane=2:3): Rf=0.66
CV: HOMO vs. Fc (DCM): 0.40 V (reversible)
LUMO vs. Fc (THF): −2.85 V (reversible)
DSC: melting point: 240° C. (onset), sublimated material
glass transition temperature Tg: 113° C. (onset), heating rate 10 K/min, sublimated material
1H-NMR (CD2Cl2 referenced to 5.31 ppm, 500.13 MHz): δ [ppm]=2.34 (s, 6H, Me), 7.08 ("d" with fine splitting, J=8.5 Hz, 4H, phenylene), 7.14 ("d", J=8.0 Hz, 4H, phenylene), 7.16 ("d" with fine splitting, J=8.5 Hz, 4H, phenylene), 7.30 ("dd", J=8.5 Hz, 3.0 Hz, 2H, naphthyl H-5 or H-8), 7.34 ("ddd", J=8.0 Hz, 7.0 Hz, 1.0 Hz, 2H, naphthyl H-6 or H-7), 7.39 ("ddd", J=8.0 Hz, 7.0 Hz, 1.0 Hz, 2H, naphthyl H-6 or H-7), 7.43 ("d", J=2.0 Hz, 2H, naphthyl H-1), 7.55 ("d" with fine splitting, J=8.5 Hz, 4H, phenylene), 7.59 ("d", J=8.0 Hz, 2H, naphthyl), 7.65 (s, 4H, terphenyl of middle ring), 7.73 ("d", J=8.5 Hz, 2H, naphthyl), 7.76 ("d", J=8.0 Hz, 2H, naphthyl).

13C-NMR (CD2Cl2 referenced to 53.73 ppm, 125.76 MHz): δ [ppm]=20.91 (q, Me), 119.99 (d, naphthyl), 123.97 (d, terphenyl or phenylene), 124.44 (d, naphthyl), 124.68 (d, naphthyl), 125.62 (d, terphenyl or phenylene), 126.59 (d, naphthyl), 127.09 (d, naphthyl), 127.12 (d, terphenyl or phenylene), 127.78 (d, terphenyl or phenylene), 127.80 (d, naphthyl), 129.08 (d, naphthyl), 130.28 (s), 130.38 (d, terphenyl or phenylene), 133.79 (s), 134.62 (s), 134.82 (s), 139.21 (s), 145.27 (s, N-bound), 145.83 (s, N-bound), 147.67 (s, N-bound).

| Elemental analysis: | ber. values | C 90.14%, H 5.82%, N 4.04% |
| --- | --- | --- |
| | exp. values | C 90.31%, H 5.95%, N 4.06% |
| Conductivities | (10 mol. %): | 8.58E−04 S/cm (d1); 7.24E−05 S/cm (d2); 2.53E−05 S/cm (d3). |

2.2.4 Characterisation of N4,N4''-di([1,1'-biphenyl]-4-yl)-N4,N4''-bis(4-methoxyphenyl)-[1,1':4',1''-terphenyl]-4,4''-diamine (7)

TLC (silica gel, DCM/n-hexane=1:1): Rf=0.38
CV: HOMO vs. Fc (DCM): 0.33 V (reversible)
LUMO vs. Fc (THF): −2.96 V (irreversible)
DSC: melting point: no melting peak observed, unsublimated material
glass transition temperature Tg: 121° C. (peak), heating rate 10 K/min, unsublimated material
1H-NMR (CD2Cl2 referenced to 5.31 ppm, 500.13 MHz): δ [ppm]=3.81 (s, 6H, MeO), 6.90 ("d" with fine splitting, J=9.0 Hz, 4H, phenylene), 7.13 ("d" with fine splitting, J=9.0 Hz, 8H, phenylene), 7.14 ("d" with fine splitting, J=9.0 Hz, 4H, phenylene), 7.30 ("t", J=7.5 Hz, 2H, p-Ph), 7.41 ("t", J=7.5 Hz, 4H, m-Ph), 7.50 ("d" with fine splitting, J=8.5 Hz, 4H, phenylene, 7.54 ("d" with fine splitting, J=8.5 Hz, 4H, phenylene), 7.58 ("d", J=7.5 Hz, 4H, o-Ph), 7.64 (s, 4H, terphenyl of middle ring).
13C-NMR (CD2Cl2 referenced to 53.73 ppm, 125.76 MHz): δ [ppm]=55.76 (q, MeO), 115.16 (d), 123.22 (d), 123.27 (d), 126.78 (d), 127.07 (d), 127.70 (d), 127.92 (d), 127.96 (d), 129.05 (d), 134.19 (s), 134.80 (s), 139.19 (s), 140.55 (s), 140.89 (s), 147.65 (s, CAr—N), 147.68 (s, CAr—N), 157.00 (s, CAr—O). The signal of the p-Ph carbon could not be found due to signal overlaps.

| Elemental analysis: | ber. [%]: | C 86.57 H 5.71 N 3.61 O 4.12 |
| --- | --- | --- |
| | exp. [%]: | C 86.08 H 5.95 N 3.52 O not meas. |

2.2.5 Characterisation of N4,N4''-di(naphthalen-1-yl)-N4,N4''-di-p-tolyl-[1,1':4',1''-terphenyl]-4,4''-diamine (1)

TLC (silica gel, DCM/n-hexane=1:2): Rf=0.54
CV: HOMO vs. Fe (DCM): 0.40 V (reversible)
LUMO vs. Fc (THF): −2.87 V (reversible, not clearly discernible)
DSC: melting point: 235° C. (onset), sublimated material
glass transition temperature Tg: 123° C. (onset), heating rate 10 K/min, sublimated material
1H-NMR (CDCl3 referenced to 7.26 ppm, 500.13 MHz): δ [ppm]=2.30 (s, 6H, Me), 7.01 ("d" with fine splitting, J=9.0 Hz, 4H, phenylene), 7.04 ("s", 8H, phenylene), 7.36 ("dd", J=7.5 Hz, 1.5 Hz, 2H, naphthyl), 7.37 ("ddd", J=8.5 Hz, 7.0 Hz, 1.5 Hz, 2H, naphthyl H-3 or H-6 or H-7), 7.44

("d" with fine splitting, J=8.5 Hz, 4H, phenylene), 7.46 ("t", J=7.5 Hz, 2H, naphthyl H-3, or H-6 or H-7), 7.48 ("t", J=7.5 Hz, 2H, naphthyl H-3 or H-6 or H-7), 7.57 (s, 4H, terphenyl of middle ring), 7.77 ("d", J=8.0 Hz, 2H, naphthyl), 7.89 ("d", J=8.5 Hz, 2H, naphthyl, 7.98 ("d", J=8.5 Hz, 2H, naphthyl).

13C-NMR (CDCl3 referenced to 77.0 ppm, 125.76 MHz): δ [ppm]=20.74 (q, Me), 120.87 (d), 122.90 (d), 124.30, 126.09, 126.32, 126.34 (d), 126.65 (d), 127.04, 127.31 (d), 128.35, 129.78 (d), 131.20 (s), 131.86, 132.94 (s), 135.24 (s), 138.80 (s), 143.54 (s), C—N, 145.64 (s, C—N), 148.11 (s, C—N). No signal was found due to signal overlaps. The assignment of the multiplicities is based on the signal intensities or on the underlying nOe effect.

| Elemental analysis: | ber. [%]: | C 90.14 H 5.82 N 4.04 |
|---|---|---|
| | exp. [%]: | C 90.18 H 5.79 N 4.06 |
| Conductivities | (10 mol. %): | 3.60E−04 S/cm (d1); 2.13E−05 S/cm (d2); 2.10E−06 S/cm (d3). |

2.2.6 Characterisation of N4,N4"-bis(4-methoxyphenyl)-N4,N4"-di(naphthalen-1-yl)-[1,1':4',1"-terphenyl]-4,4"-diamine (2)

TLC (silica gel, DCM/n-hexane=1:1): Rf=0.49
CV: HOMO vs. Fc (DCM): Measurement not possible, electrodimerisation suspected
LUMO vs. Fc (THF): −3.09 V (THF reversible)
DSC: melting point: 258° C. (onset), unsublimated material
glass transition temperature Tg: 109° C. (onset), heating rate 10 K/min, unsublimated material
1H-NMR (CD2Cl2 referenced to 5.31 ppm, 500.13 MHz): δ [ppm]=3.76 (s, 6H, MeO), 6.81 ("d" with fine splitting, J=9.0 Hz, 4H, phenylene), 6.88 ("d" with fine splitting, J=8.5 Hz, 4H, phenylene), 7.11 ("d" with fine splitting, J=9.0 Hz, 4H, phenylene), 7.33 ("d", J=7.5 Hz, 2H, naphthyl), 7.38 ("t" with fine splitting, J=7.5 Hz, 2H, naphthyl H-6 or H-7), 7.42 ("d" with fine splitting, J=8.5 Hz, 4H, phenylene), 7.46 ("t" with fine splitting, J=8.0 Hz, 2H, naphthyl H-6 or H-7), 7.49 ("t", J=7.5 Hz, 2H, naphthyl H-3), 7.56 (s, 4H, terphenyl of middle ring), 7.78 ("d", J=8.0 Hz, 2H, naphthyl), 7.90 ("d", J=8.0 Hz, 2H, naphthyl), 7.98 ("d", J=8.5 Hz, 2H, naphthyl).

13C-NMR (CDCl3 referenced to 77.0 ppm, 125.76 MHz): δ [ppm]=55.72 (q, MeO), 114.87 (d, anisyl), 119.99 (d, naphthyl, supposed two signals overlapped), 124.48 (d, naphthyl), 125.74 (d, phenylene), 126.43 (d, naphthyl), 126.56 (d, phenylene), 126.68 (d, naphthyl), 126.83 (d, phenylene), 127.15 (d, naphthyl), 127.47 (d, phenylene), 128.73 (d, naphthyl), 131.42 (s), 132.45 (s), 135.68 (s), 139.02 (s), 141.48 (s), 143.96 (s, CArN), 149.08 (s, CArN), 156.17 (s, CArO).

| Elemental analysis: | ber. [%]: | C 86.16 H 5.56 N 3.86 |
|---|---|---|
| | exp. [%]: | C 84.95 H 5.66 N 3.78 |

2.2.7 Characterisation of N4,N4"-bis(4-methoxyphenyl)-N4,N4"-di(naphthalen-2-yl)-[1,1':4',1"-terphenyl]-4,4"-diamine (5)

TLC (silica gel, DCM/n-hexane=1:1): Rf=0.50
CV: HOMO vs. Fc (DCM): 0.33 V (reversible)
LUMO vs. Fc (THF): −2.81 V (reversible, not clear)
DSC: melting point: 226° C. (onset), unsublimated material
glass transition temperature Tg: 118° C. (onset), heating rate 10 K/min, unsublimated material
1H-NMR (CD2Cl2 referenced to 5.31 ppm, 500.13 MHz): δ [ppm]=3.81 (s, 6H, OMe), 6.90 ("d" with fine splitting, J=9.0 Hz, 4H, phenylene), 7.14 ("d" with fine splitting, J=8.5 Hz, 4H, phenylene), 7.15 ("d" with fine splitting, J=9.0 Hz, 4H, phenylene), 7.29 ("dd", J=9.0 Hz, 2.0 Hz, 2H, naphthyl H-3 or H-4), 7.32 ("ddd", J=8.0 Hz, 7.0 Hz, 1.0 Hz, 2H, naphthyl H-6 or H-7), 7.38 ("ddd", J=8.0 Hz, 7.0 Hz, 1.0 Hz, 2H, naphthyl H-6 or H-7), 7.39 ("d", J=2.0 Hz, 2H, naphthyl H-1), 7.54 ("d" with fine splitting, J=8.5 Hz, 4H, phenylene), 7.58 ("d", J=8.0 Hz, 2H, naphthyl H-5 or H-8), 7.65 (s, 4H, terphenyl of middle ring), 7.72 ("d", J=9.0 Hz, 2H, naphthyl H-3 or H-4), 7.75 ("d", J=8.0 Hz, 2H, naphthyl H-5 or H-8).

13C-NMR (CD2Cl2 referenced to 53.73 ppm, 125.76 MHz): δ [ppm]=55.75 (q, Me), 115.16 (d, phenylene), 119.13 (d, naphthyl), 123.30 (d, phenylene), 123.99 (d, naphthyl), 124.51 (d, naphthyl), 126.58 (d, naphthyl), 127.02 (d, naphthyl), 127.07 (d, phenylene), 127.78 (d, naphthyl), 127.88 (d, phenylene), 129.01 (d, naphthyl), 130.07 (s), 134.26 (s), 134.82 (s), 139.18 (s), 140.72 (s), 145.98 (s, CAr—N), 147.80 (s, CAr—N), 156.96 (s, CAr—O). The signal assignment to the naphthyl or phenylene units is based solely on the significant intensity differences of the carbon signals.

| Elemental analysis: | ber. [%]: | C 86.16 H 5.56 N 3.86 O 4.41 |
|---|---|---|
| | exp. [%]: | C 86.28 H 5.58 N 3.86 O 4.58 |

2.2.8 Characterisation of N4,N4"-di([1,1'-biphenyl]-4-yl)-N4,N4"-bis(4-phenoxyphenyl)-[1,1':4',1"-terphenyl]-4,4"-diamine (13)

TLC (silica gel, DCM/n-hexane=1:1): Rf=0.43
CV: HOMO vs. Fc (DCM): 0.39 V (reversible)
LUMO vs. Fc (THF): −2.94 V (reversible)
DSC: melting point: no melting peak observed, sublimated material
glass transition temperature Tg: 107° C. (onset), heating rate 10 K/min, sublimated material
1H-NMR (CD2Cl2 referenced to 5.31 ppm, 500.13 MHz): δ [ppm]=6.98 ("d" with fine splitting, J=9.0 Hz, 4H, phenylene), 7.05 ("dd", J=8.5 Hz, 1.0 Hz, 4H, o-Ph), 7.11 ("t" with fine splitting, J=7.5 Hz, 2H, p-Ph), 7.17 ("d" with fine splitting, J=9.0 Hz, 4H, phenylene), 7.18 ("d", with fine splitting, J=8.0 Hz, 8H, phenylene), 7.31 ("t" with fine splitting, J=7.5 Hz, 2H, p-Ph), 7.36 ("t" with fine splitting, J=8.0 Hz, 4H, m-Ph), 7.42 ("t", J=7.5 Hz, 4H, m-Ph), 7.52 ("d" with fine splitting, J=8.5 Hz, 4H, phenylene), 7.57 ("d" with fine splitting, J=9.0 Hz, 4H, phenylene), 7.59 ("dd", J=8.5 Hz, 1.0 Hz, 4H, o-Ph), 7.66 (s, 4H, terphenyl of middle ring).

13C-NMR (CD2Cl2 referenced to 53.73 ppm, 125.76 MHz): δ [ppm]=118.82 (d), 120.32 (d), 123.44 (d, p-Ph), 123.86 (d), 123.92 (d), 126.84 (d), 127.15 (d), 127.84 (d), 128.06 (d), 129.08 (d), 130.06 (d), 134.70 (s), 135.36 (s), 139.21 (s), 140.82 (s), 143.20 (s), 147.41 (s, CAr—N), 147.46 (s, CAr—N), 153.57 (s, CAr—O), 157.85 (s, CAr—O). It was not possible to find two carbon signals due to signal overlap. At least one of these signals is overlapped based on the significantly higher signal intensity of the signal at 127.15 ppm.

| Elemental analysis: | ber. [%]: | C 87.97 H 5.37 N 3.11 O 3.55 |
| | exp. [%]: | C 88.01 H 5.46 N 3.15 O not meas. |
| Conductivity | (10 mol. %): | 2.70E−04 S/cm (d1) |

2.2.9 Characterisation of N4,N4''-di([1,1'-biphenyl]-4-yl)-N4,N4''-di(naphthalen-1-yl)-[1,1':4',1''-terphenyl]-4,4''-diamine (8)

TLC (silica gel, DCM/n-hexane=1:1): Rf=0.60
CV: HOMO vs. Fc (DCM): 0.42 V (reversible)
LUMO vs. Fc (THF): −2.94 V (reversible)
DSC: melting point: no melting peak observed, even with cyclical measurement, sublimated material
glass transition temperature Tg: 138° C. (onset), heating rate 10 K/min, sublimated material
1H-NMR (CD2Cl2 referenced to 5.31 ppm, 500.13 MHz): δ [ppm]=7.12 (2×"d" overlapped, J=9.0 Hz, 8H, phenylene), 7.28 ("t" with fine splitting, J=7.5 Hz, 2H, p-Ph), 7.40 ("t", J=7.5 Hz, 4H, m-Ph), 7.39-7.42 (m, 4H), 7.46-7.53 (in, 12H), 7.56 ("dd", J=8.5 Hz, 1.0 Hz, 4H, o-Ph), 7.61 (s, 4H, terphenyl of middle ring), 7.84 ("d", J=8.0 Hz, 2H, naphthyl), 7.94 ("d", J=8.5 Hz, 2H, naphthyl), 8.00 ("d", J=8.5 Hz, 2H, naphthyl).
13C-NMR (CD2Cl2 referenced to 53.73 ppm, 125.76 MHz): δ [ppm]=122.27 (d, phenylene), 122.30 (d, phenylene), 124.35 (d, naphthyl), 126.58 (d, naphthyl or p-Ph), 126.77 (d, phenylene), 126.83 (d, naphthyl or p-Ph), 127.05 (d, phenylene), 127.10 (d, naphthyl or p-Ph), 127.72 (d, phenylene), 127.76 (d, naphthyl or p-Ph), 127.93 (d, phenylene), 128.81 (d, naphthyl or p-Ph), 129.04 (d, phenylene), 131.59 (s), 134.06 (s), 134.66 (s), 135.74 (s), 139.10 (s), 140.81 (s), 143.44 (s), 147.89 (s, CAr—N), 147.90 (s, CAr—N). It was not possible to find two signals due to signal overlaps.

| Elemental analysis: | ber. [%]: | C 91.14 H 5.43 N 3.43 |
| | exp. [%]: | C 91.32 H 5.55 N 3.43 |
| Conductivity | (10 mol. %): | 7.31E−05 S/cm (d1) |

2.2.10 Characterisation of N4,N4''-Di([1,1'-biphenyl]-4-yl)-N4,N4''-di(naphthalen-2-yl)-[1,1':4',1''-terphenyl]-4,4''-diamine (9)

TLC (silica gel, DCM/n-hexane=1:1): Rf=0.64
CV: HOMO vs. Fc (DCM): 0.43 V (reversible)
LUMO vs. Fe (THF): −2.85 V (reversible)
DSC: melting point: no melting peak observed, sublimated material
glass transition temperature Tg: 134° C. (onset), heating rate 10 K/min, sublimated material
1H-NMR (CD2Cl2 referenced to 5.31 ppm, 500.13 MHz): δ [ppm]=7.237 ("d" with fine splitting, J=8.5 Hz, 4H, phenylene), 7.241 ("d" with fine splitting, J=8.5 Hz, 4H, phenylene), 7.32 ("t" with fine splitting, J=7.5 Hz, 2H, p-Ph), 7.36 ("dd", J=9.0 Hz, 2.5 Hz, 2H, naphthyl), 7.37 ("ddd", J=8.0 Hz, 7.0 Hz, 1.0 Hz, 2H, naphthyl H-6 or H-7), 7.41 ("ddd", =8.0 Hz, 7.0 Hz, 1.0 Hz, 2H, naphthyl H-6 or H-7), 7.44 ("d" with fine splitting, J=7.5 Hz, 4H, phenylene), 7.53 ("d", J=2.0 Hz, 2H, naphthyl H-1), 7.55 ("d" with fine splitting, J=8.5 Hz, 4H, phenylene), 7.60 ("d" with fine splitting, J=9.0 Hz, 4H, phenylene), 7.62 ("t" with fine splitting, J=7.0 Hz, 4H, m-Ph), 7.64 ("d", J=8.0 Hz, broad peaks, 2H, naphthyl), 7.68 (s, 4H, terphenyl of middle ring), 7.78 ("d", J=9.0 Hz, 2H, naphthyl), 7.79 ("d", J=8.0 Hz, broad peaks, 2H, naphthyl).
13C-NMR (CD2Cl2 referenced to 53.73 ppm, 125.76 MHz): δ [ppm]=121.05 (d, naphthyl or p-Ph), 124.73 (d, phenylene), 124.79 (d, phenylene), 124.84 (d, naphthyl or p-Ph), 124.97 (d, naphthyl or p-Ph), 126.66 (d, naphthyl or p-Ph), 126.88 (d, phenylene), 127.19 (d, naphthyl or p-Ph), 127.22 (phenylene), 127.73 (d, naphthyl or p-Ph), 127.83 (d, naphthyl or p-Ph), 127.94 (d, phenylene), 128.14 (d, phenylene), 129.09 (d, phenylene), 129.28, 130.59 (s), 135.93 (s), 140.78 (s), 145.46 (s), 147.27 (s, CAr—N), 147.34 (s, CAr—N). Some signals could not be found due to the low substance concentration in the NMR solvent due to the limited solubility thereof, even with longer measurement times.

| Elemental analysis: | ber. [%]: | C 91.14 H 5.43 N 3.43 |
| | exp. [%]: | C 90.21 H 5.62 N 3.47 |
| Conductivity | (10 mol. %): | 1.92E−04 S/cm (d1) |

2.2.11 Characterisation of N4,N4''-bis(4-(tert-butyl)phenyl)-N4,N4''-di(naphthalen-2-yl)-[1,1':4',1''-terphenyl]-4,4''-diamine (11)

TLC (silica gel, DCM/n-hexane=1:2): Rf=0.58
DSC: melting point: no melting peak observed, sublimated material
glass transition temperature Tg: 133° C. (onset), already discernible prior to shock cooling, heating rate 10 K/min, sublimated material
1H-NMR (CD2Cl2 referenced to 5.31 ppm, 500.13 MHz): δ [ppm]=1.33 (s, 18H, Me), 7.10 ("d" with fine splitting, J=8.5 Hz, 4H, phenylene), 7.17 ("d" with fine splitting, J=8.5 Hz, 41-1, phenylene), 7.30 ("dd", J=9.0 Hz, 2.0 Hz, 2H, naphthyl), 7.33 ("d" with fine splitting, J=8.5 Hz, 4H, phenylene), 7.34 ("ddd", J=8.0 Hz, 7.0 Hz, 1.5 Hz, 2H, naphthyl H-6 or H-7), 7.39 ("ddd", J=8.0 Hz, 7.0 Hz, 1.5 Hz, 2H, naphthyl H-6 or H-7), 7.45 ("d", J=2.5 Hz, 2H, naphthyl H-1), 7.55 ("d" with fine splitting, J=8.5 Hz, 4H, phenylene), 7.60 ("d", J=8.0 Hz, broadened signal, 2H, naphthyl), 7.66 (s, 4H, terphenyl of middle ring), 7.74 ("d", J=9.0 Hz, 2H, naphthyl), 7.76 ("d", J=8.5 Hz, broadened signal, 2H, naphthyl).
13C-NMR (CD2Cl2 referenced to 53.73 ppm, 125.76 MHz): δ [ppm]=31.47 (q, Me), 34.57 (s, CMe3), 120.19 (d, naphthyl), 124.12 (d, phenylene), 124.60 (d, naphthyl), 124.69 (d, naphthyl), 124.82 (d, phenylene), 126.56 (d, naphthyl), 126.59 (d, phenylene), 127.08 (d, naphthyl), 127.13 (d, phenylene), 127.77 (d, phenylene), 127.79 (d, naphthyl), 129.07 (d, naphthyl), 130.32 (s), 134.69 (s), 134.81 (s), 139.24 (s), 145.09 (s), 145.78 (s), 146.87 (s, CAr—N), 147.66 (s, CAr—N).

| Elemental analysis: | ber. [%]: | C 89.65 H 6.75 N 3.61 |
| | exp. [%]: | C 89.63 H 6.64 N 3.66 |
| Conductivity | (10 mol. %): | 6.92E−04 S/cm (d1) |

2.2.12 Characterisation of N4,N4''-di(naphthalen-2-yl)-N4,N4''-bis(4-phenoxyphenyl)-[1,1':4',1''-terphenyl]-4,4''-diamine (12)

TLC (silica gel, DCM/n-hexane=1:1): Rf=0.51
DSC: melting point: no melting peak observed, sublimated material
glass transition temperature Tg: 100° C. (onset), heating rate 10 K/min, sublimated material 1H-NMR (CD2Cl2 referenced to 5.31 ppm, 500.13 MHz): δ [ppm]=6.98 ("d" with fine splitting, J=9.0 Hz, 4H, phenylene), 7.06 ("d" with fine splitting, J=8.0 Hz, 4H, o-Ph), 7.10 ("t", J=7.5 Hz, 2H, p-Ph), 7.17 ("d" with fine splitting, J=9.0 Hz, 4H, phenylene), 7.19 ("d" with fine splitting, J=8.5 Hz, 4H, phenylene), 7.33 ("dd", J=8.5 Hz, 2.0 Hz, 2H, naphthyl), 7.34-7.37 (m, 6H), 7.40 ("ddd", J=8.0 Hz, 7.0 Hz, 1.5 Hz, 2H, naphthyl H-6 or H-7), 7.46 ("d", J=2.5 Hz, 2H, naphthyl H-1), 7.57 ("d" with fine splitting, J=9.0 Hz, 4H, phenylene), 7.62 ("d", J=8.0 Hz, 2H, naphthyl), 7.66 (s, 4H, terphenyl of middle ring), 7.75 ("d", J=8.5 Hz, 2I-1, naphthyl), 7.77 ("d", J=7.5 Hz, 2H, naphthyl).

13C-NMR (CD2Cl2 referenced to 53.73 ppm, 125.76 MHz): δ [ppm]=118.82 (d, phenylene or o-Ph or m-Ph), 120.00 (d, naphthyl or p-Ph), 120.29 (d, phenylene or o-Ph or m-Ph), 123.43 (d, naphthyl or p-Ph), 123.89 (d, phenylene or o-Ph or m-Ph), 124.32 (d, naphthyl or p-Ph), 124.76 (d, naphthyl or p-Ph), 126.63 (d, naphthyl or p-Ph), 127.09 (d, phenylene or o-Ph or m-Ph), 127.14 (d, phenylene or o-Ph or m-Ph), 127.80 (d, naphthyl or p-Ph), 127.84 (d, phenylene or o-Ph or m-Ph), 129.17 (d, naphthyl or p-Ph), 130.05 (d, phenylene or o-Ph or m-Ph), 130.31 (s), 134.75 (s), 134.79 (s), 139.23 (s), 143.32 (s, CAr—N), 145.72 (s, CAr—N), 147.60 (s, CAr—N), 153.56 (s, CAr—O), 157.83 (s, CAr—O). One of the naphthyl-CH signals or p-Ph carbon is overlapped by other signals.

| Elemental analysis: | ber. [%]: | C 87.71 H 5.22 N 3.30 O 3.77 |
| --- | --- | --- |
| | exp. [%]: | C 87.73 H 5.30 N 3.32 O not meas. |
| Conductivity | (10 mol. %): | 4.42E−04 S/cm (d1) |

2.2.13 Characterisation of N4,N4''-di([1,1'-biphenyl]-4-yl)-N4,N4''-bis(4-(tert-butyl)phenyl)-[1,1':4',1''-terphenyl]-4,4''-diamine (25)

TLC (silica gel, DCM/n-hexane=1:1): Rf=0.76
DSC: melting point: 202° C., sublimated material
glass transition temperature Tg: 138° C. (onset), heating rate 10 K/min, sublimated material 1H-NMR (CD2Cl2 referenced to 5.31 ppm, 500.13 MHz): δ [ppm]=1.33 (s, 18H, Me), 7.10 ("d" with fine splitting, J=9.0 Hz, 4H, phenylene), 7.16 ("d" with fine splitting, J=8.5 Hz, 8H, phenylene), 7.30 ("t" with fine splitting, J=7.5 Hz, 2H, p-Ph), 7.34 ("d" with fine splitting, J=9.0 Hz, 4H, phenylene), 7.42 ("t" with fine splitting, J=7.5 Hz, 4H, m-Ph), 7.51 ("d" with fine splitting, J=8.5 Hz, 4H, phenylene), 7.55 ("d" with fine splitting, J=9.0 Hz, 4H, phenylene), 7.59 ("dd", J=8.0 Hz, 1.5 Hz, 4H, o-Ph), 7.65 (s, 4H, terphenyl of middle ring).

13C-NMR (CD2Cl2 referenced to 53.73 ppm, 125.76 MHz): δ [ppm]=31.47 (q, Me), 34.56 (s, CMe3), 124.05 (d), 124.11 (d), 124.92 (d), 126.59 (d), 126.82 (d), 127.12 (d), 127.75 (d), 127.97 (d), 129.05 (d), 134.63 (s), 135.27 (s), 139.22 (s), 144.96 (s), 146.91 (s), 147.48 (s, CAr—N), 147.52 (s, CAr—N). The p-phenyl carbon and a further aromatic s-carbon are overlapped by other signals.

| Elemental analysis: | ber. [%]: | C 89.81 H 6.81 N 3.38 |
| --- | --- | --- |
| | exp. [%]: | C 89.80 H 6.72 N 3.41 |
| Conductivities | (10 mol. %): | 1.04E−03 S/cm (d1); 4.15E−04 S/cm (d2); 3.37E−05 S/cm (d3). |

2.2.14 Characterisation of N4,N4''-Di([1,1'-biphenyl]-2-yl)-N4,N4''-di-p-tolyl-[1,1':4',1''-terphenyl]-4,4''-diamine (38)

TLC (silica gel, DCM/n-hexane=1:1): Rf=0.65
DSC: melting point: 280° C. (onset), sublimated material
glass transition temperature Tg: 90° C. (onset), heating rate 10 K/min, sublimated material 1H-NMR (CD2Cl2 referenced to 5.31 ppm, 500.13 MHz): δ [ppm]=2.22 (s, 6H, Me), 6.76 ("d" with fine splitting, J=8.5 Hz, 4H, para-phenylene), 6.85 ("d" with fine splitting, J=8.5 Hz, 4H, para-phenylene), 6.90 ("d", J=8.0 Hz, 4H), 7.09-7.15 (m, 6H), 7.22 ("dd", J=8.0 Hz, 1.5 Hz, 4H), 7.28-7.39 (m, 12H), 7.53 (s, 4H, terphenyl of middle ring).

13C-NMR (CD2Cl2 referenced to 53.73 ppm, 125.76 MHz): δ [ppm]=20.66 (q, Me), 121.39 (d, para-phenylene), 123.21 (d, para-phenylene), 126.19 (d, ortho-phenylene or p-Ph), 126.80 (d, para-phenylene), 126.98 (d, ortho-phenylene or p-Ph), 127.14 (d, para-phenylene), 128.06 (d, para-phenylene), 128.81 (d, para-phenylene), 129.07 (d, ortho-phenylene or p-Ph), 129.57 (d, para-phenylene), 129.84 (d, ortho-phenylene or p-Ph), 131.85 (s), 132.14 (d, ortho-phenylene or p-Ph), 132.79 (s), 139.05 (s), 140.12 (s), 140.80 (s), 144.91 (s, CAr—N), 145.02 (s, CAr—N), 147.76 (s, CAr—N).

| Elemental analysis: | ber. [%]: | C 90.29 H 5.95 N 3.76 |
| --- | --- | --- |
| | exp. [%]: | C 90.37 H 6.00 N 3.79 |
| Conductivities | (10 mol. %): | 3.28E−04 S/cm (d1); 1.63E−04 S/cm (d2); 3.64E−06 S/cm (d3). |

2.2.15 Characterisation of 2',5'-dimethyl-N4,N4''-di(naphthalen-2-yl)-N4,N4''-diphenyl-[1,1':4',1''-terphenyl]-4,4''-diamine (41)

TLC (silica gel, DCM/n-hexane=1:2): Rf=0.55
DSC: melting point: 242° C. (onset), sublimated material
glass transition temperature Tg: 102° C. (onset), heating rate 10 K/min, sublimated material 1H-NMR (CD2Cl2 referenced to 5.31 ppm, 500.13 MHz): δ [ppm]=2.34 (s, 6H, Me), 7.07 ("t" with fine splitting, J=7.5 Hz, 2H, p-Ph), 7.16 ("d" with fine splitting, J=8.5 Hz, 4H, phenylene unit of terphenyl core), 7.18 (s, 2H, CH terphenyl of middle ring), 7.19 ("d" with fine splitting, J=7.5 Hz, 4H, o-Ph), 7.28 ("d" with fine splitting, J=8.5 Hz, 4H, phenylene unit of terphenyl core), 7.31 ("t" with fine splitting, J=7.5 Hz, 4H, m-Ph), 7.33 ("d", J=9.0 Hz, 2H, naphthyl), 7.35 ("ddd", J=8.0 Hz, 7.0 Hz, 1.0 Hz, 2H, naphthyl H-6 or H-7), 7.40 ("ddd", J=8.0 Hz, 7.0 Hz, 1.0 Hz, 2H, naphthyl H-6 or H-7), 7.48 ("d", J=2.0 Hz, 2H, naphthyl H-1), 7.61 ("d", J=8.5 Hz, 2H, naphthyl), 7.76 ("d", J=8.5 Hz, 2H, naphthyl), 7.77 ("d", J=7.5 Hz, 2H, naphthyl).

13C-NMR (CD2Cl2 referenced to 53.73 ppm, 125.76 MHz): δ [ppm]=20.14 (q, Me), 120.51 (d), 123.42 (d), 123.89 (d, phenylene or o-Ph or m-Ph), 124.69 (d), 124.78 (d), 124.88 (d, phenylene or o-Ph or m-Ph), 126.58 (d), 127.12 (d), 127.80 (d), 129.14 (d), 129.64 (d, phenylene or o-Ph or m-Ph), 130.39 (d, phenylene or o-Ph or m-Ph), 132.15 (d), 132.93 (s), 134.80 (s), 136.49 (s), 140.42 (s), 145.79 (s, CAr—N), 146.76 (s, CAr—N), 148.07 (s, CAr—N). The absent quart. carbon signal is highly likely overlapped by the signal at 130.39 ppm, based on the signal intensity thereof.

| | | |
|---|---|---|
| Elemental analysis: | ber. [%]: | C 90.14 H 5.82 N 4.04 |
| | exp. [%]: | C 90.55 H 5.91 N 4.05 |
| Conductivity | (10 mol. %): | 1.36E−04 S/cm (d1). |

2.2.16 Characterisation of N4,N4"-di([1,1'-biphenyl]-4-yl)-N4,N4"-bis(2,4-dimethylphenyl)-[1,1':4',1"-terphenyl]-4,4"-diamine (17)

TLC (silica gel, DCM/n-hexane=1:2): Rf=0.36

DSC: melting point: no melting peak observed, sublimated material glass transition temperature Tg: 116° C. (onset), heating rate 10 K/min, sublimated material 1H-NMR (CD2Cl2 referenced to 5.31 ppm, 500.13 MHz): δ [ppm]=2.07 (s, 6H, ortho-Me), 2.36 (s, 6H, para-Me), 7.06 ("d" with fine splitting, J=9.0 Hz, 8H, phenylene), 7.07 (br. s, 4H, xylyl ring), 7.13 (br. s, 2H, xylyl ring), 7.29 ("tt", J=7.5 Hz, 1.0 Hz, 2H, p-Ph), 7.41 ("t" with fine splitting, J=7.5 Hz, 4H, m-Ph), 7.48 ("d" with fine splitting, J=8.5 Hz, 4H, phenylene), 7.52 ("d" with fine splitting, J=8.5 Hz, 4H, phenylene), 7.57 ("dd", J=8.0 Hz, 1.5 Hz, 4H, o-Ph), 7.63 (s, 4H, terphenyl of middle ring).

13C-NMR (CD2Cl2 referenced to 53.73 ppm, 125.76 MHz): δ [ppm]=18.44 (q, ortho-Me), 21.05 (q, para-Me), 121.74 (d, phenylene or o-Ph or m-Ph), 121.76 (d, phenylene or o-Ph or m-Ph), 126.72 (d, phenylene or o-Ph or m-Ph), 126.95 (d, xylyl or p-Ph), 126.99 (d, phenylene or o-Ph or m-Ph), 127.61 (d, phenylene or o-Ph or m-Ph), 127.82 (d, phenylene or o-Ph or m-Ph), 128.50 (d, xylyl or p-Ph), 129.03 (d, phenylene or o-Ph or m-Ph), 129.76 (d, xylyl or p-Ph), 132.71 (d, xylyl or p-Ph), 133.59 (s), 134.15 (s), 136.67 (s), 136.76 (s), 139.14 (s), 140.93 (s), 142.57 (s, CAr—N), 146.97 (s, CAr—N). The absent quart. carbon signal is highly likely overlapped by the signal at 146.97 ppm, based on the signal intensity thereof.

| | | |
|---|---|---|
| Elemental analysis: | ber. [%]: | C 90.12 H 6.26 N 3.62 |
| | exp. [%]: | C 90.20 H 6.38 N 3.65 |
| Conductivities | (10 mol. %): | 4.68E−04 S/cm (d1); 7.02E−05 S/cm (d2); 9.73E−06 S/cm (d3). |

2.2.17 Characterisation of N4,N4"-bis(2,4-dimethylphenyl)-N4,N4"-di(naphthalen-2-yl)-[1,1':4',1"-terphenyl]-4,4"-diamine (16)

TLC (silica gel, DCM/n-hexane=1:1): Rf=0.63
TLC (silica gel, ethyl acetate/n-hexane=1:10): Rf=0.52
DSC: melting point: no melting peak observed, sublimated material glass transition temperature Tg: 113° C. (onset), heating rate 10 K/min, sublimated material 1H-NMR (CD2Cl2 referenced to 5.31 ppm, 500.13 MHz): δ [ppm]=2.06 (s, 6H, ortho-Me), 2.37 (s, 6H, para-Me), 7.07 ("d" with fine splitting, J=8.0 Hz, 4H, phenylene), 7.08 (supposed s, 4H, xylyl-CH, naphthyl H-1), 7.14 (br. s, 2H, xylyl-CH), 7.27 (br. s, 2H, xylyl-CH), 7.28 ("d", J=9.0 Hz, 2H, naphthyl), 7.31 ("ddd", J=8.0 Hz, 7.0 Hz, 1.0 Hz, 2H, naphthyl H-6 or H-7), 7.37 ("ddd", J=8.0 Hz, 7.0 Hz, 1.0 Hz, 2H, naphthyl H-6 or H-7), 7.53 ("d" with fine splitting, J=8.5 Hz, 4H, phenylene), 7.56 ("d", J=8.0 Hz, 2H, naphthyl), 7.64 (s, 4H, terphenyl of middle ring), 7.71 ("d", J=8.5 Hz, 2H, naphthyl), 7.74 ("d", J=8.0 Hz, 2H, naphthyl).

13C-NMR (CD2Cl2 referenced to 53.73 ppm, 125.76 MHz): δ [ppm]=18.48 (q, ortho-Me), 21.06 (q, para-Me), 117.32 (d), 121.88 (d, terphenyl), 122.90 (d), 124.23 (d), 126.55 (d), 126.93 (d), 127.00 (d, terphenyl), 127.63 (d, terphenyl), 127.75 (d), 128.48 (d), 128.90 (d), 129.73 (d), 129.75 (s), 132.74 (d), 133.71 (s), 134.83 (s), 136.56 (s), 136.62 (s), 139.15 (s), 142.79 (s), 145.32 (s, CAr—N), 147.21 (s, CAr—N).

| | | |
|---|---|---|
| Elemental analysis: | ber. [%]: | C 89.96 H 6.15 N 3.89 |
| | exp. [%]: | C 90.27 H 6.32 N 3.98 |
| Conductivities | (10 mol. %): | 6.16E−04 S/cm (d1); 8.55E−05 S/cm (d2); 2.59E−05 S/cm (d3). |

2.2.18 Characterisation of N4,N4"-bis(4-isopropylphenyl)-N4,N4"-di(naphthalen-2-yl)-[1,1':4',1"-terphenyl]-4,4"-diamine (10)

TLC (silica gel, DCM/n-hexane=1:1): Rf=0.65

DSC: melting point: 258° C. (onset), sublimated material
glass transition temperature Tg: 110° C. (onset), heating rate 10 K/min, sublimated material 1H-NMR (CD2Cl2 referenced to 5.31 ppm, 500.13 MHz): δ [ppm]=1.26 (d, 3J=7.0 Hz, 12H, Me), 2.91 ("quint", 3J=7.0 Hz, 2H, CHMe2), 7.10 ("d" with fine splitting, J=8.5 Hz, 4H, phenylene), 7.17 ("d" with fine splitting, J=9.0 Hz, 4H, phenylene), 7.18 ("d" with fine splitting, J=9.0 Hz, 4H, phenylene), 7.30 ("dd", J=9.0 Hz, 2.0 Hz, 2H, naphthyl), 7.34 ("ddd", 8.0 Hz, 7.0 Hz, 1.0 Hz, 2H, naphthyl H-6 or H-7), 7.39 ("ddd", 8.0 Hz, 7.0 Hz, 1.5 Hz, 2H, naphthyl H-6 or H-7), 7.44 ("d", J=2.0 Hz, 2H, naphthyl H-1), 7.55 ("d" with fine splitting, J=8.5 Hz, 4H, phenylene), 7.60 ("d", J=8.0 Hz, 2H, naphthyl), 7.66 (s, 4H, terphenyl of middle ring), 7.74 ("d", J=9.0 Hz, 2H, naphthyl), 7.76 ("d", J=8.0 Hz, 2H, naphthyl).

13C-NMR (CD2Cl2 referenced to 53.73 ppm, 125.76 MHz): δ [ppm]=24.11 (q, Me), 33.88 (d, CHMe2), 120.09 (d, naphthyl), 124.04 (d, phenylene), 124.54 (d, naphthyl), 124.67 (d, naphthyl), 125.35 (d, phenylene), 126.56 (d, naphthyl), 127.07 (d, naphthyl), 127.12 (d, phenylene), 127.67 (d, phenylene), 127.76 (d, phenylene), 127.78 (d, naphthyl), 129.06 (d, naphthyl), 130.29 (s), 134.65 (s), 134.80 (s), 139.24 (s), 144.73 (s, CAr—N or CAr-iPr), 145.44 (s, CAr—N or CAr-iPr), 145.82 (s, CAr—N or CAr-iPr), 147.69 (s, CAr—N or CAr-iPr).

| | | |
|---|---|---|
| Elemental analysis: | ber. [%]: | C 89.80 H 6.46 N 3.74 |
| | exp. [%]: | C 89.97 H 6.47 N 3.83 |
| Conductivities | (10 mol. %): | 1.16E−03 S/cm (d1); 3.23E−04 S/cm (d2); 6.20E−05 S/cm (d3). |

2.2.19 Characterisation of N4,N4"-di(naphthalen-2-yl)-N4,N4"-di-m-tolyl-[1,1':4',1"-terphenyl]-4,4"-diamine (21)

TLC (silica gel, DCM/n-hexane=1:1): Rf=0.69

DSC: melting point: no melting peak observed, sublimated material glass transition temperature Tg: 101° C. (onset), heating rate 10 K/min, sublimated material 1H-NMR (CD2Cl2 referenced to 5.31 ppm, 500.13 MHz): δ [ppm]=2.29 (s, 6H, Me), 6.93 (broad "d", J=7.5 Hz, 2H, tolyl H-4 or H-6), 6.98 (broad "d" with "dd"-like splitting, J=8.0 Hz, 2H, tolyl H-4 or H-6), 7.03 (broad "s", 2H, tolyl H-2), 7.18 ("d" with characteristic fine splitting, J=8.5 Hz, 4H, terphenyl), 7.20 ("t", J=7.5 Hz, 2H, tolyl H-5), 7.32 ("dd", J=9.0 Hz, 2.0 Hz, 2H, naphthyl), 7.36 ("ddd", J=8.0 Hz, 7.0 Hz, 1.0 Hz, 2H, naphthyl H-6 or H-7), 7.40 ("ddd", J=8.0 Hz, 7.0 Hz, 1.0 Hz, 2H, naphthyl H-6 or H-7), 7.47 ("d", J=2.0 Hz, 2H, naphthyl H-1), 7.56 ("d" with characteristic fine splitting, J=8.5 Hz, 4H, terphenyl), 7.61 (broad "d", J=8.0 Hz, 2H, naphthyl), 7.66 (s, 4H, terphenyl of middle ring), 7.75 ("d", J=9.0 Hz, 2H, naphthyl), 7.78 (broad "d", J=7.5 Hz, 2H, naphthyl).

13C-NMR (CD2Cl2 referenced to 53.73 ppm, 125.76 MHz): δ [ppm]=21.45 (q, Me), 120.58 (d), 122.32 (d), 124.35 (d, terphenyl), 124.58 (d), 124.75 (d), 124.80 (d), 125.82 (d), 126.58 (d), 127.15 (d, terphenyl), 127.81 (d, terphenyl), 129.13 (d), 129.48 (d), 130.40 (s), 131.81 (s), 131.82 (s), 139.23 (s), 139.72 (s), 145.75 (s, CAr—N), 147.61 (s, CAr—N), 147.82 (s, CAr—N). Two carbon signals could not be found due to signal overlap. At least one of these signals is overlapped based on the significantly higher signal intensity of the signal at 127.15 ppm.

| Elemental analysis: | ber. [%]: | C 90.14 H 5.82 N 4.04 |
| --- | --- | --- |
| | exp. [%]: | C 90.12 H 5.78 N 3.96 |
| Conductivities | (10 mol. %): | 8.41E−05 S/cm (d1); 3.62E−05 S/cm (d2); 1.28E−05 S/cm (d3). |

2.2.20 Characterisation of N4,N4"-di([1,1'-biphenyl]-4-yl)-N4,N4"-dimesityl-[1,1':4',1"-terphenyl]-4,4"-diamine (20)

TLC (silica gel, DCM/n-hexane=1:1): Rf=0.57
DSC: melting point: no melting peak observed, sublimated material
glass transition temperature Tg: 141° C. (onset), heating rate 10 K/min, sublimated material
1H-NMR (CD2Cl2 referenced to 5.31 ppm, 500.13 MHz): δ [ppm]=2.05 (s, 12H, o-Me), 2.34 (s, 6H, p-Me), 7.00 (s, 4H, mesityl-H), 7.07 ("dd", actually 2×d overlapped, J=8.5 Hz, 1.0 Hz, 8H, phenylene), 7.28 ("t" with fine splitting, J=7.5 Hz, 2H, p-Ph), 7.40 ("t", J=7.5 Hz, 4H, m-Ph), 7.48 ("d" with fine splitting, J=9.0 Hz, 4H, phenylene), 7.52 ("d" with fine splitting, J=8.5 Hz, 4H, phenylene), 7.57 ("d" with fine splitting, J=7.5 Hz, 4H, o-Ph), 7.62 (s, 4H, terphenyl of middle ring).

13C-NMR (CD2Cl2 referenced to 53.73 ppm, 125.76 MHz): δ [ppm]=18.60 (q, o-Me), 21.11 (q, p-Me), 120.14 (d), 126.65 (d), 126.88 (d, p-Ph), 126.92 (d), 127.65 (d), 127.87 (d), 129.04 (d), 130.27 (d), 133.15 (s), 133.67 (s), 137.50 (s), 137.92 (s), 139.09 (s), 140.11 (s), 140.96 (s), 145.57 (s, CAr—N), 145.59 (s, CAr—N). The absent quart. carbon signal is highly likely overlapped by the signal at 137.92 ppm, based on the significantly greater signal intensity thereof compared with other quart. carbons. Also, one of the phenylene-CH signals is overlapped by other signals.

| Elemental analysis: | ber. [%]: | C 89.96 H 6.54 N 3.50 |
| --- | --- | --- |
| | exp. [%]: | C 90.03 H 6.55 N 3.48 |
| Conductivities | (10 mol. %): | 6.84E−04 S/cm (d1); 5.52E−05 S/cm (d2); 8.81E−06 S/cm (d3). |

2.2.21 Characterisation of N4,N4"-bis(3,5-bis(trifluoromethyl)phenyl)-N4,N4"-di(naphthalen-2-yl)-[1,1':4',1"-terphenyl]-4,4"-diamine (28)

TLC (silica gel, DCM/n-hexane=1:1): Rf=0.70
DSC: melting point: 242° C. (peak), sublimated material
glass transition temperature Tg: 140° C. (onset), heating rate 10 K/min, sublimated material 1H-NMR (CD2Cl2 referenced to 5.31 ppm, 500.13 MHz): δ [ppm]=7.26 ("d" with fine splitting, J=8.5 Hz, 4H, phenylene), 7.33 ("dd", J=9.0 Hz, 2.0 Hz, 2H, naphthyl), 7.44-7.49 (in, 6H, contained at 7.44 ppm, br. s, p-H CF3-ring), 7.53 (s, 4H, o-H CF3-ring), 7.59 ("d", J=2.5 Hz, 2H, naphthyl H-1), 7.66 ("d" with fine splitting, J=8.5 Hz, 4H, phenylene), 7.69 (m, 2H, naphthyl), 7.71 (s, 4H, terphenyl of middle ring), 7.84 (in, 2H, naphthyl), 7.87 ("d", J=8.5 Hz, 2H, naphthyl).

13C-NMR (CD2Cl2 referenced to 53.73 ppm, 125.76 MHz): δ [ppm]=114.82 (d, quint-splitting, actually qq, 3JCF=3.8 Hz, arom. CH between CF3 groups), 121.49 (d, br. q-splitting, 3JCF=3.3 Hz, o-H, CF3-ring), 123.197 (d, naphthyl), 123.72 (s, q-splitting, 1JCF=272.8 Hz, CF3), 124.89 (d, naphthyl), 125.85 (d, phenylene), 125.98 (d, naphthyl), 127.04 (d, naphthyl), 127.49 (d, terphenyl of middle ring), 127.57 (d, naphthyl), 128.01 (d, naphthyl), 128.60 (d, phenylene), 130.22 (d, naphthyl), 131.49 (s), 132.71 (s, q-splitting, 2JCF=33.0 Hz, CArCF3), 134.78 (s), 137.19 (s), 139.32 (s), 143.97 (s, CAr—N), 145.95 (s, CAr—N), 149.58 (s, CAr—N).

| Elemental analysis: | ber. [%]: | C 69.23 H 3.44 N 2.99 F 24.34 |
| --- | --- | --- |
| | exp. [%]: | C 69.08 H 3.49 N 2.93 F 23.90 |

2.2.22 Characterisation of N4,N4',N4",N4"-tetrakis(4-(tert-butyl)phenyl)-[1,1':4',1"-terphenyl]-4,4"-diamine (26)

TLC (silica gel, DCM/n-hexane=1:2): Rf=0.64
DSC: melting point: 336° C. (peak), sublimated material
glass transition temperature Tg: 149° C. (onset), heating rate 10 K/min, sublimated material
1H-NMR (CD2Cl2 referenced to 5.31 ppm, 500.13 MHz): δ [ppm]=1.31 (s, 36H, CMe3), 7.04 ("d" with characteristic fine splitting, J=8.5 Hz, 8H, C6H4tBu), 7.08 ("d" with characteristic fine splitting, J=8.5 Hz, 4H, terphenyl), 7.30 ("d" with characteristic fine splitting, J=8.5 Hz, 8H, C6H4tBu), 7.50 ("d" with characteristic fine splitting, J=8.5 Hz, 4H, terphenyl), 7.62 (s, 4H, terphenyl of middle ring).

13C-NMR (CD2Cl2 referenced to 53.73 ppm, 125.76 MHz): δ [ppm]=31.48 (q, Me), 34.51 (s, CMe3), 123.11 (d, terphenyl), 124.46 (d, phenylene C6H4tBu), 126.44 (d, phenylene C6H4tBu), 127.03 (d, terphenyl), 127.58 (d, terphenyl), 133.89 (s, terphenyl), 139.21 (s, terphenyl), 145.29 (s, phenylene C6H4tBu), 146.36 (s, phenylene C6H4tBu), 147.93 (s, terphenyl-CAr—N).

| Elemental analysis: | ber. [%]: | C 88.28 H 8.17 N 3.55 |
| --- | --- | --- |
| | exp. [%]: | C 88.28 H 8.11 N 3.47 |
| Conductivities | (10 mol. %): | 1.67E−04 S/cm (d1); 8.92E−05 S/cm (d2); 3.46E−06 S/cm (d3). |

2.2.23 Characterisation of N4,N4"-Di(naphthalen-1-yl)-N4,N4"-di-m-tolyl-[1,1':4',1"-terphenyl]-4,4"-diamine (22)

TLC (silica gel, DCM/n-hexane=1:1): Rf=0.68
DSC: melting point: 269° C. (peak), sublimated material
glass transition temperature Tg: 122° C. (onset), heating rate 10 K/min, sublimated material
1H-NMR (CD2Cl2 referenced to 5.31 ppm, 500.13 MHz): δ [ppm]=2.22 (s, 6H, Me), 6.80 (broad "d", J=7.5 Hz, 2H, tolyl H-4 or H-6), 6.86 (broad "dd", J=8.0 Hz, 2.0 Hz, 2H, tolyl H-4 or H-6), 6.94 (broad "s", 2H, tolyl H-2), 7.01

("d" with characteristic fine splitting, J=9.0 Hz, 4H, terphenyl), 7.10 ("t", J=8.0 Hz, 2H, naphthyl H-3 or tolyl H-5), 7.35 ("dd", J=7.5 Hz, 1.0 Hz, 2H, naphthyl), 7.38 ("ddd", J=8.0 Hz, 7.0 Hz, 1.5 Hz, 2H, naphthyl H-6 or H-7), 7.46 ("d" with characteristic fine splitting, J=9.0 Hz, 4H, terphenyl), 7.47 ("ddd", J=8.0 Hz, 7.0 Hz, 1.0 Hz, 2H, naphthyl H-6 or H-7), 7.50 ("t", J=8.0 Hz, 2H, naphthyl H-3 or tolyl H-5), 7.58 (s, 4H, terphenyl of middle ring), 7.81 ("d", J=8.5 Hz, 2H, naphthyl), 7.19 ("d", J=8.5 Hz, 2H, naphthyl), 7.96 ("d", J=8.5 Hz, 2H, naphthyl).

13C-NMR (CD2Cl2 referenced to 53.73 ppm, 125.76 MHz): δ [ppm]=21.47 (q, Me), 119.88 (d), 121.71 (d, terphenyl), 123.32 (d), 123.37 (d), 124.39 (d), 126.46 (d), 126.65 (d), 126.70 (d), 126.83 (d), 126.95 (d, terphenyl), 127.56 (d, terphenyl), 127.64 (d), 128.72 (d), 129.21 (d), 131.65 (s), 133.47 (s), 135.69 (s), 139.08 (s), 139.44 (s), 143.71 (s, CAr—N), 148.34 (s, CAr—N), 148.44 (s, CAr—N).

| Elemental analysis: | ber. [%]: | C 90.14 H 5.82 N 4.04 |
| --- | --- | --- |
| | exp. [%]: | C 89.91 H 5.86 N 4.06 |
| Conductivities | (10 mol. %): | 1.22E−04 S/cm (d1); 5.53E−05 S/cm (d2); 9.69E−06 S/cm (d3). |

2.2.24 Compound (40)

Conductivities (10 mol. %): 1.57E-04 S/cm (d1); 4.09E-05 S/cm (d2); 5.73E-07 S/cm (d3).

2.2.25 Characterisation of N4,N4"-di([1,1'-biphenyl]-4-yl)-N4,N4"-bis(4-(tert-butyl)phenyl)-2',5'-dimethyl-[1,1':4',1"-terphenyl]-4,4"-diamine (36)

TLC (silica gel, DCM/n-hexane=1:3): Rf=0.35

DSC: melting point: no melting point observed, sublimated material glass transition temperature Tg: 131° C. (onset), heating rate 10 K/min, sublimated material 1H-NMR (CD2Cl2 referenced to 5.31 ppm, 500.13 MHz): δ [ppm]=1.34 (s, 18H, tBu), 2.33 (s, 6H, Me), 7.12 ("d" with characteristic fine splitting, J=8.5 Hz, 4H, phenylene), 7.15 ("d" with characteristic fine splitting, J=8.5 Hz, 4H, phenylene), 7.17 (s, 2H, terphenyl of middle ring), 7.18 ("d" with characteristic fine splitting, J=9.0 Hz, 4H, phenylene), 7.27 ("d" with characteristic fine splitting, J=8.5 Hz, 4H, phenylene), 7.31 ("t" with discernible fine splitting, J=7.5 Hz, 21-1, p-Ph), 7.35 ("d" with characteristic fine splitting, J=8.5 Hz, 4H, phenylene), 7.42 ("t", J=7.5 Hz, 4H, m-Ph), 7.51 ("d" with characteristic fine splitting, J=8.5 Hz, 4H, phenylene), 7.59 ("d" with discernible fine splitting, J=7.5 Hz, 4H, o-Ph).

13C-NMR (CD2Cl2 referenced to 53.73 ppm, 125.76 MHz): δ [ppm]=20.16 (q, Me), 31.50 (q, tBu), 34.56 (s, tBu), 123.56 (d), 123.91 (d), 124.89 (d), 126.58 (d), 126.83 (d), 127.08 (d, p-Ph), 127.95 (d), 129.06 (d), 130.32 (d), 132.15 (d, CH terphenyl of middle ring), 132.92 (s), 135.08 (s), 136.16 (s), 140.46 (s), 140.93 (s), 145.13 (s, CAr—N or CAr-tBu), 146.79 (s, CAr—N or CAr-tBu), 146.80 (s, CAr—N or CAr-tBu), 147.68 (s, CAr—N or CAr-tBu).

| Elemental analysis: | ber. [%]: | C 89.68 H 7.06 N 3.27 |
| --- | --- | --- |
| | exp. [%]: | C 89.58 H 7.04 N 3.26 |
| Conductivity | (10 mol. %): | 5.71E−04 S/cm (d1) |

2.2.25 Characterisation of N4,N4"-bis(3,5-dimethylphenyl)-N4,N4"-di(naphthalen-2-yl)-[1,1':4',1"-terphenyl]-4,4"-diamine (48)

TLC (silica gel, DCM/n-hexane=1:1): Rf=0.70

CV: HOMO vs. Fe (DCM): 0.47 V (reversible)

LUMO vs. Fc (THF): −2.86 V (reversible)

DSC: melting point: no melting peak glass transition temperature Tg: 117° C. (onset), heating rate 10 K/min, sublimated material 1H-NMR (CD2Cl2 referenced to 5.31 ppm, 500.13 MHz): δ [ppm]=2.25 (s, 12H, Me), 6.77 (br. s, 2H, p-xylyl), 6.83 (br. s, 4H, o-xylyl), 7.17 ("d" with characteristic fine splitting, J=9.0 Hz, 4H, terphenyl CH), 7.31 ("dd", J=9.0 Hz, 2.0 Hz, 2H), 7.36 ("ddd", J=8.0 Hz, 6.5 Hz, 1.5 Hz, 2H, naphthyl H-6 or H-7), 7.40 ("ddd", J=8.0 Hz, 7.0 Hz, 1.5 Hz, 2H, naphthyl H-6 or H-7), 7.46 ("d", J=2.5 Hz, 2H, naphthyl H-1), 7.56 ("d" with characteristic fine splitting, J=8.5 Hz, 4H, terphenyl CH), 7.61 ("d", J=8.0 Hz, 2H, naphthyl), 7.66 (s, 4H, terphenyl middle ring), 7.75 ("d", J=9.0 Hz, 2H, naphthyl), 7.77 ("d", J=8.0 Hz, 2H, naphthyl).

13C-NMR (CD2Cl2 referenced to 53.73 ppm, 125.76 MHz): δ [ppm]=21.35 (q, Me), 120.48 (d, naphthyl or p-xylyl), 123.17 (d, terphenyl or o-xylyl), 124.24 (d, terphenyl or o-xylyl), 124.74 (d, naphthyl or p-xylyl), 124.78 (d, naphthyl or p-xylyl), 125.69 (d, naphthyl or p-xylyl), 126.56 (d, naphthyl or p-xylyl), 127.14 (d, terphenyl or o-xylyl), 127.77 (d, terphenyl or o-xylyl), 127.80 (d, naphthyl or p-xylyl), 129.07 (d, naphthyl or p-xylyl), 130.35 (s), 134.65 (s), 134.82 (s), 139.23 (s), 139.46 (most probably two overlaid signals due to signal intensity, although quite low field for missing d-carbon signal), 145.86 (s, CAr—N), 147.71 (s, CAr—N), 147.72 (s, CAr—N).

| Elemental analysis: | ber. [%]: | C 89.96, H 6.15, N 3.89. |
| --- | --- | --- |
| | exp. [%]: | C 90.27, H 6.11, N 3.84. (after sublimation) |
| Conductivity | (10 mol. %): | 7.24E−04 S/cm (d1) |

2.2.26 Characterisation of N4,N4"-di([1,1'-biphenyl]-4-yl)-N4,N4"-bis(3,5-dimethylphenyl)-[1,1':4',1"-terphenyl]-4,4"-diamine (49)

CV: HOMO vs. Fc (DCM): 0.41 V (reversible)

LUMO vs. Fc (THF): −3.07 V (irreversible)

DSC: melting point: no melting peak glass transition temperature Tg: 123° C. (onset), heating rate 10 K/min, sublimated material 1H-NMR (CD2Cl2 referenced to 5.31 ppm, 500.13 MHz): δ [ppm]=2.25 (s, 12H, Me), 6.76 (br. s, 2H, p-H xylyl moiety), 6.81 (s, 4H, o-H xylyl moiety), 7.15 ("d", J=8.0 Hz, 8H), 7.31 ("t", J=7.5 Hz, 2H, p-Ph), 7.42 ("t", J=7.5 Hz, 4H, m-Ph), 7.51 ("d" with further fine splitting, J=9.0 Hz, 4H), 7.55 ("d" with further fine splitting, J=8.5 Hz, 4H), 7.59 ("d", J=7.5 Hz, 4H, o-Ph), 7.66 (s, 4H, terphenyl middle ring).

13C-NMR (CD2Cl2 referenced to 53.73 ppm, 125.76 MHz): δ [ppm]=21.33 (q, Me), 123.19 (d), 124.24 (d), 124.28 (d), 125.69 (d), 126.83 (d), 127.13 (d), 127.75 (d), 127.97 (d), 129.07 (d), 134.64 (s), 135.27 (s), 139.24 (s), 139.46, 140.87 (s), 147.54 (s, CAr—N), 147.59 (s, CAr—N).

| Elemental analysis: | ber. [%]: | C 90.12, H 6.26, N 3.62. |
| | exp. [%]: | C 90.09, H 6.21, N 3.58. |
| | | (after sublimation) |
| Conductivity | (10 mol. %): | 4.21E−04 S/cm (d1) |

Electronic Component

With use of the organic compounds according to the invention for producing doped organic semiconducting materials, which in particular can be arranged in the form of layers or electric conduction paths, it is possible to produce a multiplicity of electronic components or devices containing same. In particular, the doped semiconductor layers can be used to produce organic diodes, in particular organic light-emitting diodes (OLEDs), organic solar cells, in particular those with high rectification ratio such as 103-107, preferably 104-107 or 105-107. The conductivity of the doped layers and/or the improvement of the charge carrier injection of contacts into the doped layer can be improved by the dopants according to the invention. In particular in the case of OLEDs, the component may have a pin structure or an inverted structure, but is not limited hereto. The use of the doped semiconductor layers according to the invention is not limited, however, to the above-mentioned advantageous exemplary embodiments. OLEDs free from ITO are also preferred. Furthermore, OLEDs having at least one organic electrode are also provided. Preferred organic electrode(s) are conductive layers that contain the following materials as main components: PEDOT-PSS, polyaniline, carbon nanotubes, graphite.

The typical structure of a standard OLED may appear as follows:
1. carrier, substrate, for example glass
2. electrode, hole-injecting (anode=positive pole), preferably transparent, for example indium-tin-oxide (ITO) or FTO (Graz. J. Phys. V. 35 no. 4 pp. 1016-1019 (2005))
3. hole-injection layer,
5. hole-side blocking layer in order to prevent exciton diffusion from the emitting layer and to prevent charge carrier leakage from the emitting layer
6. light-emitting layer or system of a number of layers contributing to light emission, for example CBP (carbazole derivative) with emitter admixture (for example phosphorescent triplet emitter iridium-tris-phenylpyridine Ir(ppy)3) or Alq3 (tris-quinolinato-aluminium) mixed with emitter molecules (for example fluorescent singlet emitter coumarin),
7. electron-side blocking layer in order to prevent exciton diffusion from the emitting layer and to prevent charge carrier leakage from the emitting layer, for example BCP (bathocuproine),
8. electron transport layer (ETL), for example BPhen, Alq3 (tris-quinolinato-aluminium),
10. electrode, usually a metal with low work function, electron-injecting (cathode=negative pole), for example aluminium.

Of course, layers can be omitted, or a layer (or a material) can take on a number of properties, for example layers 3-5 or layers 7 and 8 can be combined. Further layers can also be used. Stacked OLEDs are also provided.

This structure describes the non-inverted (anode on the substrate), substrate-side-emitting (bottom-emission) structure of an OLED. There are various concepts for describing OLEDs emitting away from the substrate (see references in DE102 15 210.1); this means inter alia that the substrate-side electrode (in the non-inverted case the anode) is then reflective (or transparent for a clear OLED) and the top electrode is (semi-)transparent. If the order of the layers is inverted (cathode on substrate), reference is made to inverted OLEDs (see references in DE101 35 513.0). Here too, performance losses are to be expected without special measures.

A preferred design of the structure of an OLED according to the invention is the inverted structure (wherein the cathode is on the substrate), and wherein the light is emitted through the substrate. Furthermore, the OLED is top-emitting in accordance with one embodiment.

The hole injection layer is preferably directly adjacent to the hole-side blocking layer, wherein the hole injection layer is doped.

In another embodiment of the invention, the hole injection layer and the hole-side blocking layer preferably contain the same matrix material.

In a particularly preferred embodiment of the invention, the hole-side blocking layer is at least 5 times, preferably at least 20 times, thicker than the hole injection layer, wherein the hole-side blocking layer is undoped and the hole injection layer is doped.

OLEDs were produced as follows:

A layer of compound (4) was doped with compound (d1). The doped layer was deposited by mixed evaporation of the material with structure (4) and of the dopant (d1) under high vacuum on a glass substrate coated with ITO. The concentration of the dopant in the matrix was 3.0 mol. %, layer thickness 50 nm. Without interruption of the vacuum, a red emitter layer (20 nm) of compound (40) was then doped with iridium(III)bis(2-methyldibenzo-[f,h]quinoxaline)(acetylacetonate) (076RE, from ADS), an undoped electron transport and hole blocking layer formed from 4-(naphthalen-1-yl)-2,7,9-triphenylpyrido[3,2-h]quinazoline (10 nm), and then a 4-(naphthalen-1-yl)-2,7,9-triphenylpyrido[3,2-h]quinazoline layer (50 nm, mol. %) doped with W2(hpp)4 (tetrakis (1,3,4,6,7,8-hexahydro-2H-pyrimido[1,2-a]pyrimidinato)ditungsten(II)). Al (100 nm) was used as cathode. The components thus processed were then encapsulated with respect to water with a cover glass (a corresponding getter was introduced beforehand). Compound (40) was used as emitter matrix in order to compare merely the variation of the transport layer. Nevertheless, the compounds according to the invention can also be used as emitter matrix.

The produced OLED has a voltage of 2.6 V at a current density of 10 mA/cm2, and a quantum efficiency here of 11%. The output at 10 mA/cm2 is 20.6 lm/W. A current density of 100 mA/cm2 can already be achieved at the low voltage of 3.0 V.

In a comparative test with an OLED produced with use of a relatively good compound (40) instead of (4), just 18.6 lm/W and a quantum efficiency of 9.9% can be achieved under the same measurement conditions. Similar comparative results are achieved with compound (3).

The typical structure of an organic solar cell may appear as follows:
1. carrier, substrate, for example glass
2. anode, preferably transparent, for example indium-tin-oxide (ITO)
3. hole injection layer,
5. hole-side intermediate layer, preferably blocking layer in order to prevent exciton diffusion from the absorption layer (optical active layer, also referred to as emitting layer) and to prevent charge carrier leakage from the emitting layer,
6. absorption layer, typically a highly light-absorbing layer formed from a heterojunction (two or more layers or mixed layer), for example mixed layer formed from $C_{60}$ and ZnPc, 7. electron transport layer,
10. cathode, for example aluminium.

Of course, layers can be omitted or a layer may take on a number of properties. Further layers can also be used. Stacked (tandem) solar cells are provided. Variants such as transparent solar cells, inverted structure or m-i-p solar cells are also possible.

A preferred design of the structure of a solar cell is the inverted structure (wherein the cathode is on the substrate), and wherein the light penetrates through the substrate.

A further preferred design of the structure of a solar cell is the inverted structure (wherein the cathode is on the substrate), and wherein the light penetrates through the anode.

Organic solar cells, also known as photovoltaic elements, were produced as follows:

A layer of fullerene C60 was doped with W2(hpp)4. The doped layer was deposited by mixed evaporation under high vacuum on a glass substrate coated with ITO. The concentration of the dopant in the matrix was 10 mol. %, layer thickness 10 nm. An undoped C60 layer 20 nm thick was then produced without interruption of the vacuum, followed by a mixed layer, molar 1:1, between C60 and ZnPc with a layer thickness of 30 nm. A 45 nm thick layer of compound (25) doped 3 mol. % with (d1) followed. 2 nm (di) was used as injection layer—this improves the contact with the silver electrode, wherein this layer can be omitted with other electrodes, such as Au. Ag (100 nm) was used as anode. The components thus processed were then encapsulated with respect to water using a cover glass—a corresponding getter was introduced beforehand.

Under standard-AM1.5-illumination, the following parameters were measured, Voc=0.50 V, Jsc=9.5 mA/cm2, FF=53%, and total efficiency of 2.5%.

The same structure was repeated with compound (20) instead of compound (25) with very similar results.

The organic layer arrangement of an OLED or a solar cell typically comprises a number of organic layers arranged one above the other. One or more pn junctions may also be provided within the organic layer arrangement, as is known for stacked OLEDs (see EP 1 478 025 A2), wherein such a pn junction is formed in one embodiment with the aid of a p-doped hole transport layer and an n-doped electric transport layer, which are formed in direct contact with one another. Such a pn junction constitutes a structure generating electric charges, in which electric charges are generated upon application of an electric potential, preferably in the boundary region between the two layers.

In solar cells, the pn junction is also used to connect stacked heterojunctions and to thus add up the voltage generated by this component (US2006027834A). The junctions have a function similar to tunnel transitions in stacked inorganic heterojunction solar cells although the physical mechanisms are probably not the same.

The transitions are also used to obtain an improved charge injection (extraction with solar cells) relative to the electrodes (EP1808910).

To improve the electronic properties in an organic electronic component, it was proposed in document WO 2005/109542 A1 to form a pn junction with a layer formed from an organic semiconductor material of the n-type and a layer formed of an organic material of the p-type, wherein the layer formed of the organic semiconductor material of the n-type is in contact with an electrode formed as an anode. In this way, an improved injection of charge carriers in the form of holes is achieved in the layer formed of the organic semiconductor material of the p-type.

In order to stabilize the pn junction, a layer of a material other than intermediate layer is used. Such stabilized pn-junctions are described for example in US2006040132A, where a metal is used as intermediate layer. OLEDs with this metal layer have a shorter service life due to the diffusion of the metal atoms.

Stable p-doped layers are produced with the materials according to the invention, which layers are provided in the pn junctions in order to produce stable organic semiconductor components.

Further embodiments for solar cells can be deduced from U.S. Pat. No. 7,675,057 B2.

The features disclosed in the description and in the claims may be essential both individually and in any combination for the implementation of the invention in various embodiments thereof.

The invention claimed is:

1. A compound of formula (I):

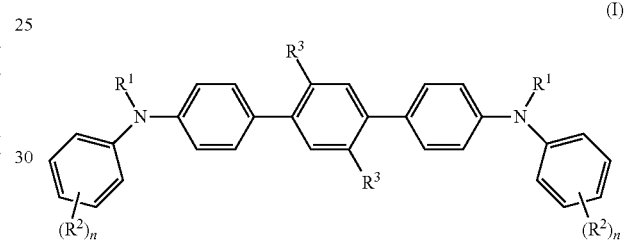

wherein $R^1$ is selected independently from naphthyl or biphenylyl;

$R^2$ is selected independently from methyl, isopropyl, tert-butyl, $C_1$-$C_5$ haloalkyl, or $C_6$-$C_{12}$ aryloxy;

$R^3$ is selected independently from H or $C_1$-$C_5$ alkyl;

n is independently selected from 1-3; and (i) when each $R^2$ is methyl, the compound of formula (I) is selected from

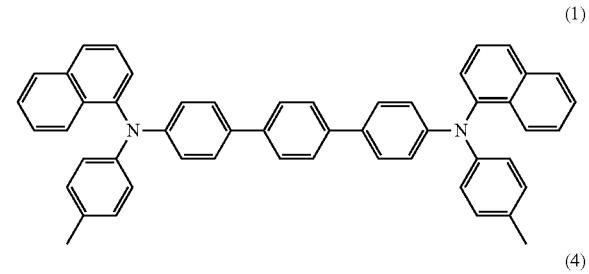

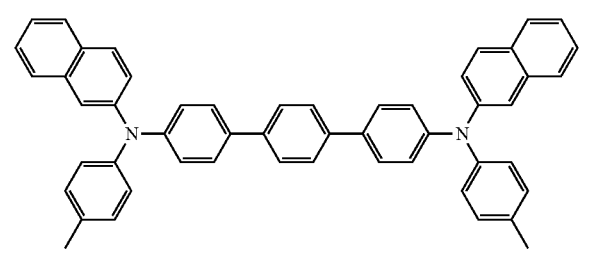

-continued
(15)
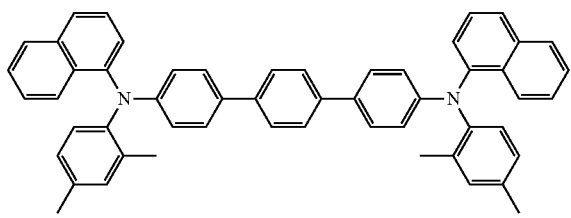
(16)
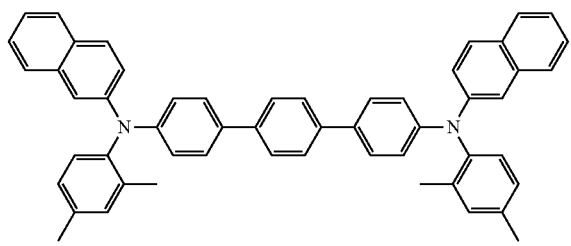
(17)
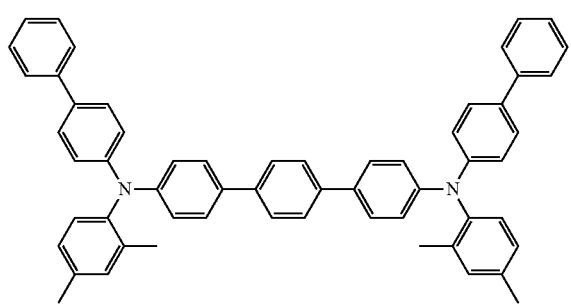
(18)
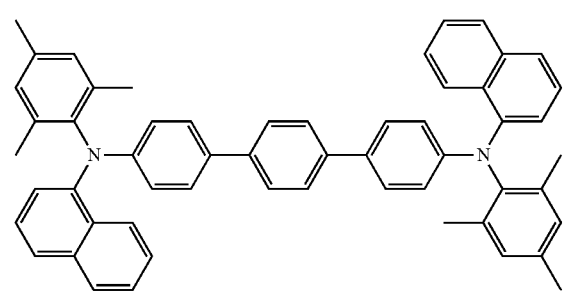
(19)
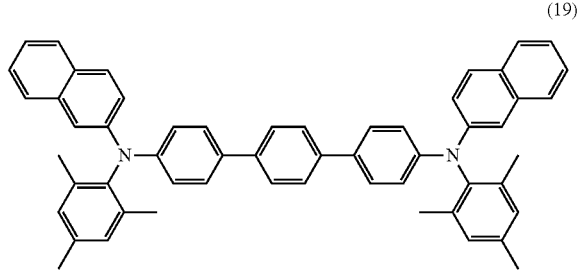
-continued
(20)
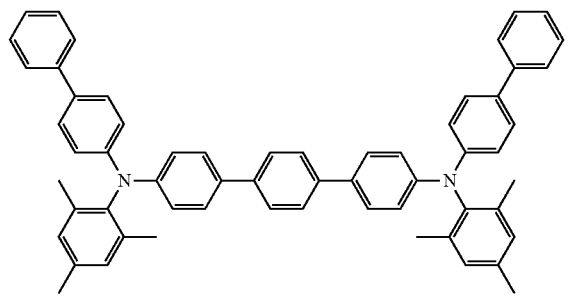
(34)
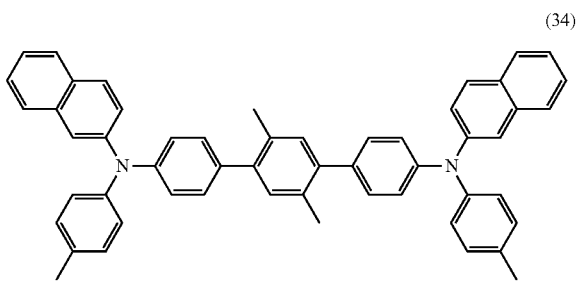
(35)
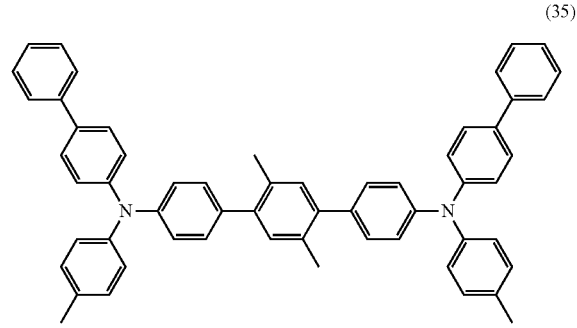
(37)
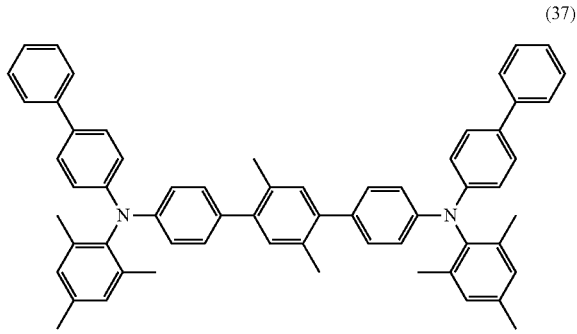
(38)
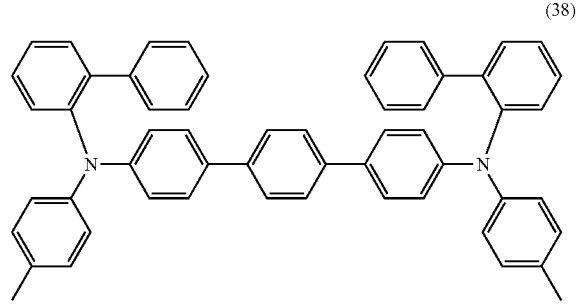

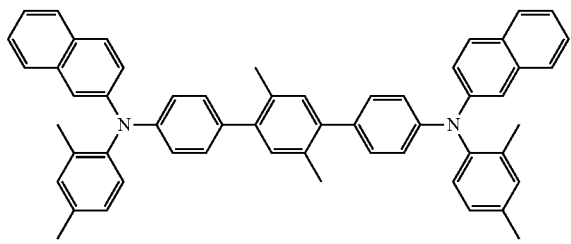
(42)
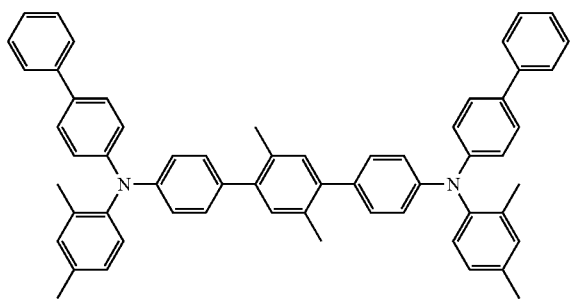
(44)
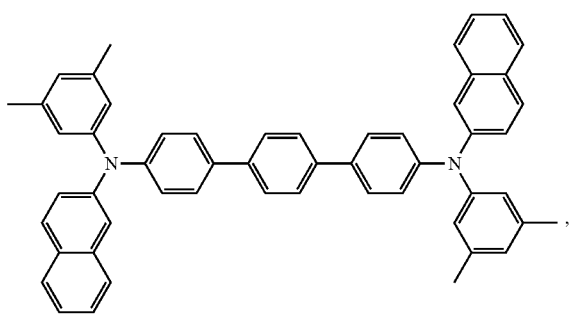
(48)
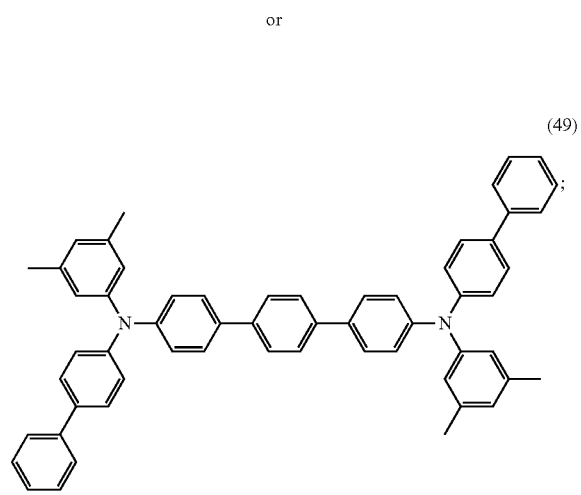
(49)
and
(ii) when at least one R² is tert-butyl or isopropyl, the compound of formula (I) is selected from
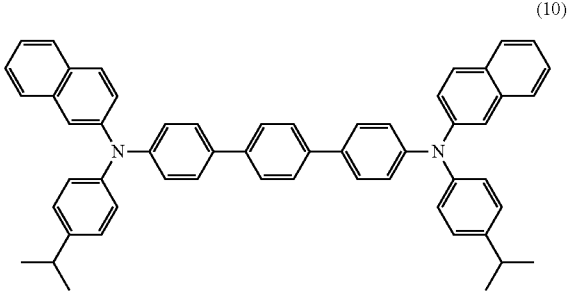
(10)
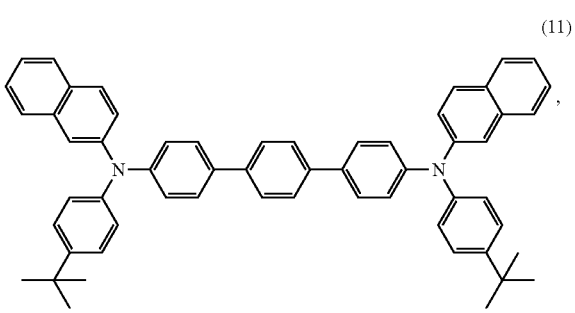
(11)
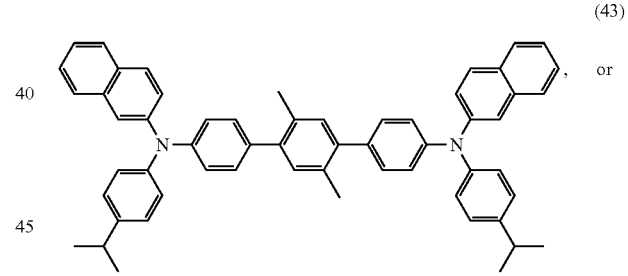
(43)
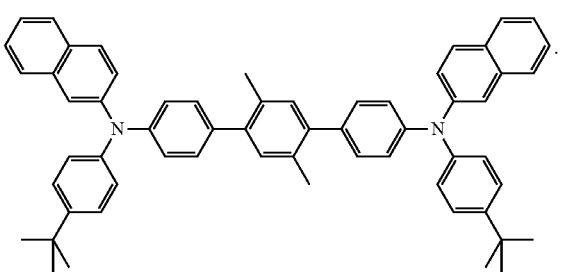
(45)
2. The compound according to claim 1, wherein the substitution by R² is in at least one of the ortho or para position of the phenyl ring.

3. The compound according to claim 1, wherein $R^2$ is $C_6$-$C_{12}$ aryloxy.

4. The compound according to claim 3, wherein $R^2$ is phenoxy.

5. The compound according to claim 1, wherein $R^1$ is β-naphthyl or 1,1'-biphenyl-4-yl.

6. The compound according to claim 1, wherein $R^3$ is H or methyl.

7. The compound according to claim 1, wherein the compound has a structure according to formula (III):

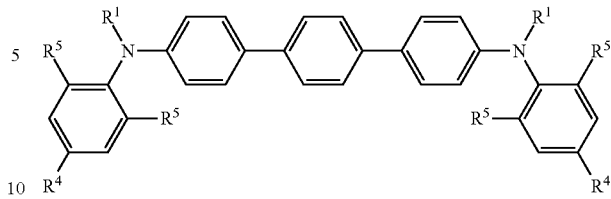

(III)

wherein $R^4$ and $R^5$ are selected independently from H or $R^2$, and at least one of $R^4$ or $R^5$ is not H.

8. The compound according to claim 1, wherein the compound is selected from one of the following formulas:

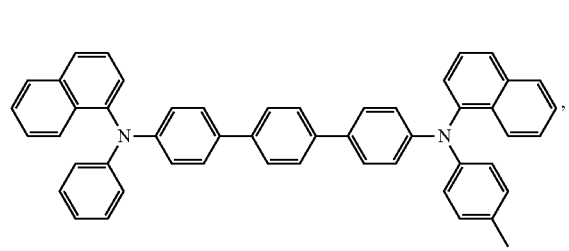

(1)

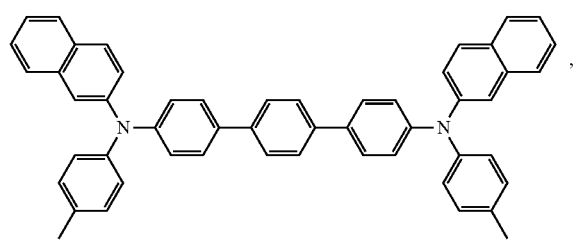

(4)

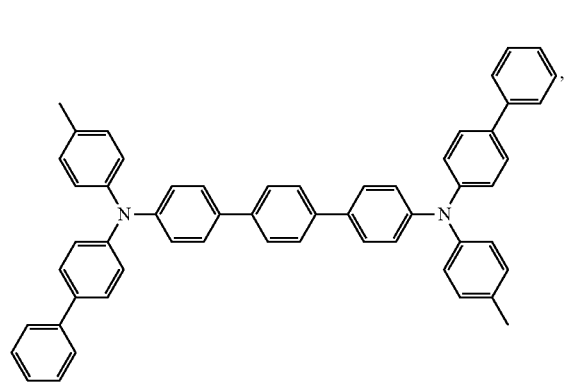

(6)

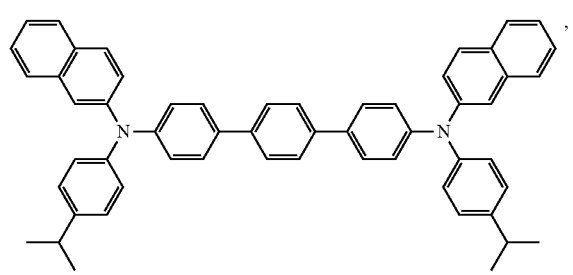

(10)

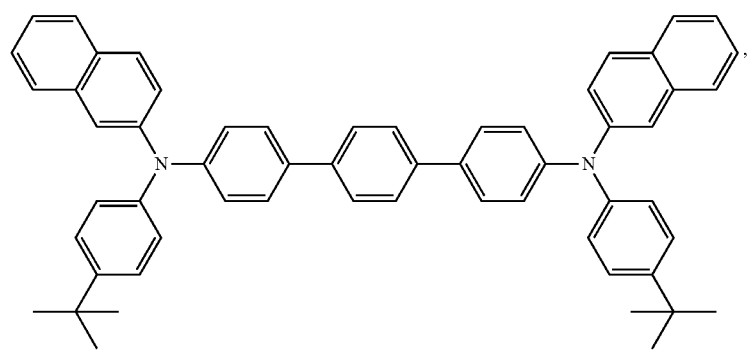

(11)

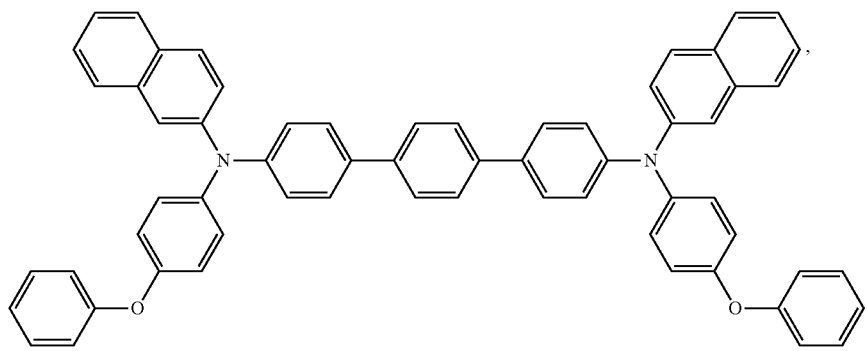
(12)
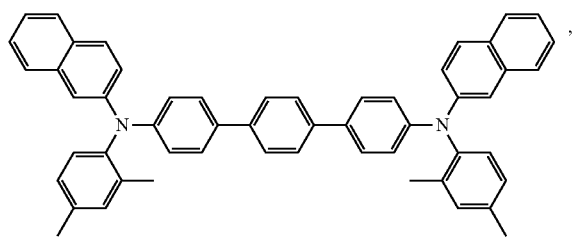
(16)
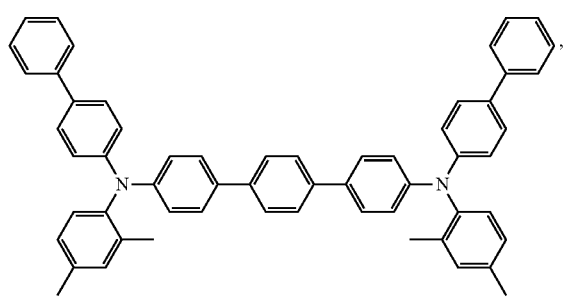
(17)
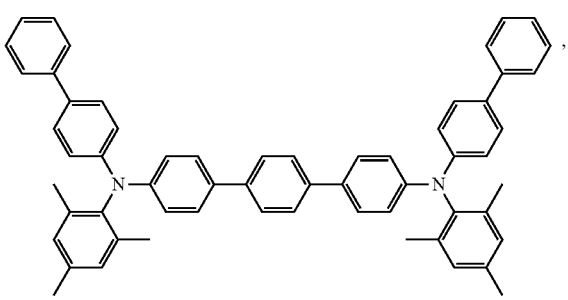
(20)
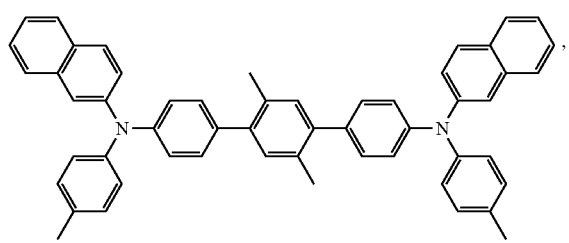
(34)
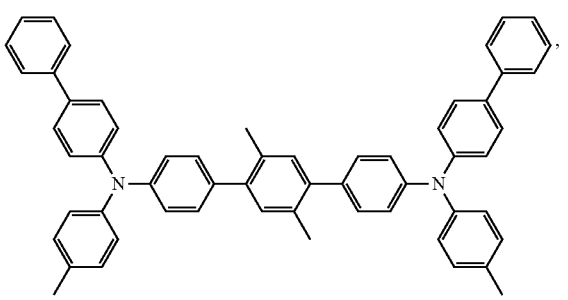
(35)
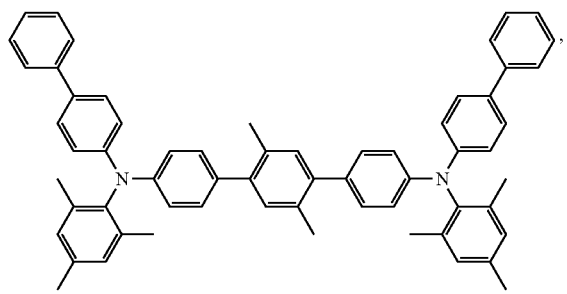
(37)
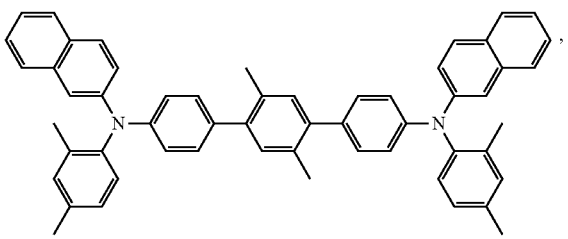
(42)

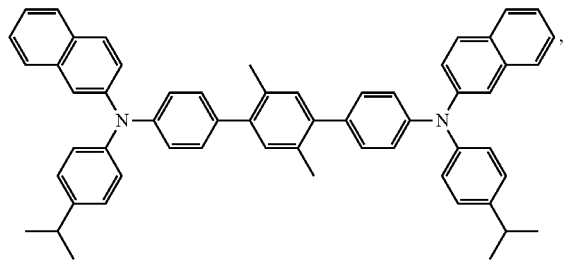

(43)

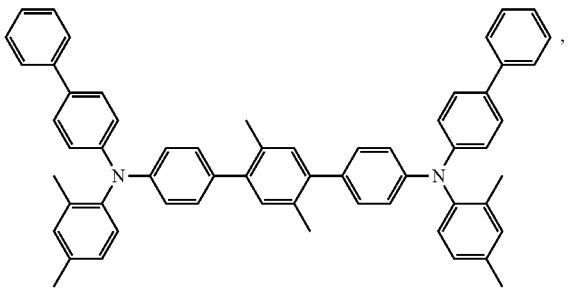

(44)

or

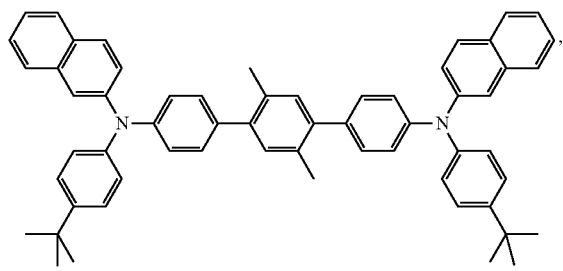

(45)

9. The compound according to claim 8, wherein the compound is selected from one of formulas (4), (6), (10), (20), (34), (36), or (37).

10. An organic semiconducting component comprising at least one layer, which contains a compound according to claim 1.

11. The organic semiconducting component according to claim 10, wherein the layer containing the compound according to claim 1 is doped.

12. The organic semiconducting component according to claim 10, wherein the layer containing the compound according to claim 1 comprises at least one doped region and at least one other region, wherein the other region is either doped to a lesser extent that than the doped region or undoped.

13. The organic semiconducting component according to claim 10, wherein the layer containing the compound according to claim 1 is a hole transport layer or emitter layer.

14. The organic semiconducting component according to claim 10, wherein the component is an organic light-emitting diode (OLED) or a photovoltaic component.

15. The compound according to claim 1, wherein the substituents represented by at least one of $R^1$, $R^2$, and $R^3$ are identical.

16. The organic semiconducting component according to claim 14, wherein the component is a solar cell.

* * * * *

UNITED STATES PATENT AND TRADEMARK OFFICE
CERTIFICATE OF CORRECTION

PATENT NO. : 9,748,493 B2
APPLICATION NO. : 14/384886
DATED : August 29, 2017
INVENTOR(S) : Mike Zoellner et al.

It is certified that error appears in the above-identified patent and that said Letters Patent is hereby corrected as shown below:

In the Claims

At Column 65, Line 14, delete "

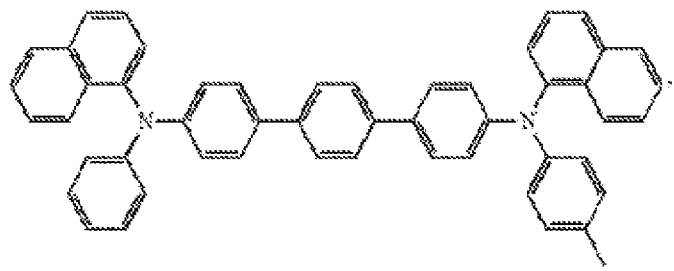

" and insert

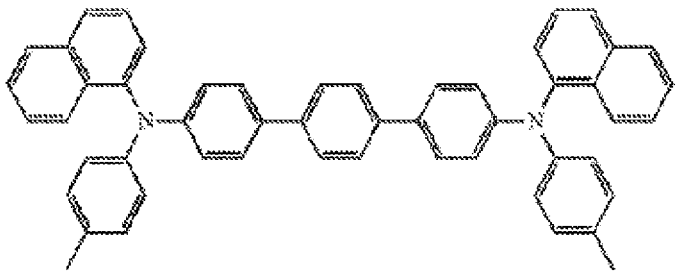

--; and

At Column 69, Line 31, delete "(36),".

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*